US010936064B2

(12) United States Patent
Lussier et al.

(10) Patent No.: US 10,936,064 B2
(45) Date of Patent: Mar. 2, 2021

(54) LIGHT FIELD DISPLAY, ADJUSTED PIXEL RENDERING METHOD THEREFOR, AND ADJUSTED VISION PERCEPTION SYSTEM AND METHOD USING SAME ADDRESSING ASTIGMATISM OR SIMILAR CONDITIONS

(71) Applicant: EVOLUTION OPTIKS LIMITED, Bridgetown (BB)

(72) Inventors: Guillaume Lussier, Montreal (CA); Yaiza Garcia, Beaconsfield (CA); Matej Goc, Kingston (CA); Jean-François Joly, Victoria (CA)

(73) Assignee: Evolution Optiks Limited, Bridgetown (BB)

( * ) Notice: Subject to any disclaimer, the term of this patent is extended or adjusted under 35 U.S.C. 154(b) by 0 days.

(21) Appl. No.: 17/038,515

(22) Filed: Sep. 30, 2020

(65) Prior Publication Data

US 2021/0011553 A1   Jan. 14, 2021

Related U.S. Application Data

(63) Continuation-in-part of application No. 16/854,787, filed on Apr. 21, 2020, now Pat. No. 10,860,099,
(Continued)

(30) Foreign Application Priority Data

Oct. 22, 2018   (CA) .................................. CA 3021636

(51) Int. Cl.
*G06F 3/01* (2006.01)
*G06F 3/0484* (2013.01)
(Continued)

(52) U.S. Cl.
CPC .......... *G06F 3/013* (2013.01); *G02B 27/0025* (2013.01); *G06F 3/04845* (2013.01); *G06K 9/00604* (2013.01); *G06T 3/40* (2013.01)

(58) Field of Classification Search
CPC . G06F 3/013; G06F 3/04845; G02B 27/0025; G06K 9/00604; G06T 3/40
See application file for complete search history.

(56) References Cited

U.S. PATENT DOCUMENTS

| | | |
|---|---|---|
| 5,959,664 A | 9/1999 | Woodgate |
| 6,192,341 B1 | 2/2001 | Becker et al. |

(Continued)

FOREIGN PATENT DOCUMENTS

| | | |
|---|---|---|
| AU | 2015100739 | 7/2015 |
| DE | 102004038822 A1 | 3/2006 |

(Continued)

OTHER PUBLICATIONS

"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.

(Continued)

*Primary Examiner* — Jack Dinh
(74) *Attorney, Agent, or Firm* — Knobbe, Martens, Olson & Bear, LLP

(57) ABSTRACT

Described are various embodiments of a light field display, adjusted pixel rendering method and computer-readable medium therefor, and vision correction system and method using same addressing astigmatism or similar conditions. In one embodiment, a computer-implemented method is provided to automatically adjust user perception of an input image to be rendered on a digital display via a set of pixels (Continued)

thereof, wherein the digital display has an array of light field shaping elements.

30 Claims, 48 Drawing Sheets

Related U.S. Application Data which is a continuation-in-part of application No. PCT/IB2019/058955, filed on Oct. 21, 2019, and a continuation-in-part of application No. 16/569,137, filed on Sep. 12, 2019, now Pat. No. 10,642,355, which is a continuation of application No. 16/510,673, filed on Jul. 12, 2019, now Pat. No. 10,474,235, which is a continuation of application No. 16/259,845, filed on Jan. 28, 2019, now Pat. No. 10,394,322, said application No. 16/854,787 is a continuation-in-part of application No. 16/810,143, filed on Mar. 5, 2020, now Pat. No. 10,761,604, which is a continuation-in-part of application No. 16/551,572, filed on Aug. 26, 2019, now Pat. No. 10,636,116.

(60) Provisional application No. 62/929,639, filed on Nov. 1, 2019.

(51) Int. Cl.
    *G06T 3/40* (2006.01)
    *G06K 9/00* (2006.01)
    *G02B 27/00* (2006.01)

(56) References Cited

U.S. PATENT DOCUMENTS

| | | |
|---|---|---|
| 6,386,707 B1 | 5/2002 | Pellicano |
| 6,536,907 B1 | 3/2003 | Towner et al. |
| 6,543,898 B1 | 4/2003 | Griffin et al. |
| 6,784,905 B2 | 8/2004 | Brown et al. |
| 6,809,704 B2 | 10/2004 | Kulas |
| 6,876,758 B1 | 4/2005 | Polat et al. |
| 6,953,249 B1 | 10/2005 | Maguire, Jr. |
| 7,062,547 B2 | 6/2006 | Brown et al. |
| 7,517,086 B1 | 4/2009 | Kürkure |
| 7,866,817 B2 | 1/2011 | Polat |
| 7,891,813 B2 | 2/2011 | Ogilvie |
| 7,973,850 B2 | 7/2011 | Ishiga |
| 8,089,512 B2 | 1/2012 | Okabe et al. |
| 8,098,440 B2 | 1/2012 | Jethmalani et al. |
| 8,164,598 B2 | 4/2012 | Kimpe |
| 8,231,220 B2 | 7/2012 | Baranton |
| 8,322,857 B2 | 12/2012 | Barbur et al. |
| 8,540,375 B2 | 9/2013 | Destain |
| 8,717,254 B1 | 5/2014 | Nave et al. |
| 8,783,871 B2 | 7/2014 | Pamplona et al. |
| 8,798,317 B2 | 8/2014 | Wu |
| 8,823,742 B2 | 9/2014 | Kweon |
| 8,967,809 B2 | 3/2015 | Kirschen et al. |
| 9,010,929 B2 | 4/2015 | Lewis |
| 9,041,833 B2 | 5/2015 | Hatakeyama |
| 9,052,502 B2 | 6/2015 | Caldeira et al. |
| 9,066,683 B2 | 6/2015 | Zhou |
| 9,104,233 B2 | 8/2015 | Alberth |
| 9,159,299 B2 | 10/2015 | Lee |
| 9,177,355 B1 | 11/2015 | Buchheit |
| 9,183,806 B2 | 11/2015 | Felt |
| 9,492,074 B1 | 11/2016 | Lee et al. |
| 9,844,323 B2 | 12/2017 | Pamplona et al. |
| 9,895,057 B2 | 2/2018 | Tumlinson |
| 10,058,241 B2 | 8/2018 | Patella et al. |
| 10,085,631 B2 | 10/2018 | Shimizu et al. |
| 10,182,717 B2 | 1/2019 | Lindig et al. |
| 10,206,566 B2 | 2/2019 | Skolianos et al. |
| 10,247,941 B2 | 4/2019 | Fürsich |
| 10,335,027 B2 | 7/2019 | Pamplona et al. |
| 10,345,590 B2 | 7/2019 | Samec et al. |
| 10,394,322 B1 | 8/2019 | Gotsch |
| 10,420,467 B2 | 9/2019 | Krall et al. |
| 2006/0119705 A1 | 6/2006 | Liao |
| 2008/0309764 A1 | 12/2008 | Kubota et al. |
| 2009/0290132 A1 | 11/2009 | Shevlin |
| 2011/0019056 A1 | 1/2011 | Hirsch et al. |
| 2011/0122144 A1 | 5/2011 | Gabay |
| 2011/0157180 A1 | 6/2011 | Burger et al. |
| 2012/0113389 A1 | 5/2012 | Mukai et al. |
| 2012/0206445 A1 | 8/2012 | Chiba |
| 2012/0254779 A1 | 10/2012 | Ollivierre et al. |
| 2012/0262477 A1 | 10/2012 | Buchheit |
| 2013/0027384 A1 | 1/2013 | Ferris |
| 2013/0096820 A1 | 4/2013 | Agnew |
| 2013/0120390 A1 | 5/2013 | Marchand et al. |
| 2013/0222652 A1 | 8/2013 | Akeley et al. |
| 2014/0055692 A1 | 2/2014 | Kroll et al. |
| 2014/0063332 A1 | 3/2014 | Miyawaki |
| 2014/0118354 A1 | 5/2014 | Pais et al. |
| 2014/0137054 A1 | 5/2014 | Gandhi et al. |
| 2014/0200079 A1 | 7/2014 | Bathiche et al. |
| 2014/0267284 A1 | 9/2014 | Blanche et al. |
| 2014/0282285 A1 | 9/2014 | Sadhvani et al. |
| 2014/0327750 A1 | 11/2014 | Malachowsky et al. |
| 2014/0327771 A1 | 11/2014 | Malachowsky et al. |
| 2015/0049390 A1 | 2/2015 | Lanman et al. |
| 2015/0185501 A1 | 7/2015 | Bakaraju et al. |
| 2015/0234187 A1 | 8/2015 | Lee |
| 2015/0234188 A1 | 8/2015 | Lee |
| 2015/0336511 A1 | 11/2015 | Ukeda |
| 2016/0042501 A1 | 2/2016 | Huang et al. |
| 2016/0103419 A1 | 4/2016 | Callagy et al. |
| 2016/0134815 A1 | 5/2016 | Ishiguro et al. |
| 2016/0306390 A1 | 10/2016 | Vertegaal et al. |
| 2017/0027435 A1 | 2/2017 | Boutinon et al. |
| 2017/0060399 A1 | 3/2017 | Hough et al. |
| 2017/0227781 A1 | 8/2017 | Banerjee et al. |
| 2017/0302913 A1 | 10/2017 | Tonar et al. |
| 2017/0307898 A1 | 10/2017 | Vdovin et al. |
| 2017/0353717 A1 | 12/2017 | Zhou et al. |
| 2017/0365189 A1 | 12/2017 | Halpin et al. |
| 2018/0136486 A1 | 5/2018 | Macnamara et al. |
| 2018/0252935 A1 | 9/2018 | Vertegaal et al. |
| 2018/0290593 A1 | 10/2018 | Cho |
| 2019/0125179 A1 | 5/2019 | Xu et al. |
| 2019/0246095 A1 | 8/2019 | Kishimoto |
| 2019/0246889 A1 | 8/2019 | Mahn et al. |

FOREIGN PATENT DOCUMENTS

| | | |
|---|---|---|
| EP | 2127949 A1 | 12/2009 |
| EP | 1509121 B1 | 9/2012 |
| FR | 3059537 B1 | 5/2019 |
| WO | 2011156721 A1 | 12/2011 |
| WO | 2013166570 A1 | 11/2013 |
| WO | 2014174168 A1 | 10/2014 |
| WO | 2014197338 A2 | 12/2014 |
| WO | 2017218539 A1 | 12/2017 |
| WO | 2018092989 A1 | 5/2018 |
| WO | 2018129310 A1 | 7/2018 |

OTHER PUBLICATIONS

"Eyeglasses-free Display: Towards Correcting Visual Aberrations with Computational Light Field Displays", by Huang et al., taken from http://web.media.mit.edu/~gordonw/VisionCorrectingDisplay/, publicshed Aug. 2, 2014, pp. 1-15.

Agus M. et al., "GPU Accelerated Direct Volume Rendering on an Interactive Light Field Display", Eurographics 2008, vol. 27, No. 2, 2008.

Burnett T., "FoVI3D Extreme Multi-view Rendering for Light-field Displays", GTC 2018 (GPU Technology Conference), Silicon Valley, 2018.

(56) References Cited

OTHER PUBLICATIONS

Fattal, D. et al., A Multi-Directional Backlight for a Wide-Angle, Glasses-Free Three-Dimensional Display, Nature, Mar. 21, 2013, pp. 348-351, vol. 495.
Halle M., "Autostereoscopic displays and computer graphics", Computer Graphics, ACM SIGGRAPH, 31(2), May 1997, pp. 58-62.
Huang, F.C. et al., "Eyeglasses-Free Display: Towards Correcting Visual Aberrations With Computational Light Field Displays,", ACM Transactions on Graphics (TOG)—Proceedings of ACM SIGGRAPH 2014, vol. 33, Issue 4, Article No. 59, Jul. 2014.
International Search Report for International Application No. PCT/CA2016/051006 dated Sep. 30, 2016 in 5 pages.
Mainone, Andrew, et al. "Focus 3D: Compressive accommodation display." ACM Trans. Graph. 32.5 (2013): 153-1.
Masia B. et al., "A survey on computational displays: Pushing the boundaries of optics, computation, and perception", Computer & Graphics, vol. 37, 2013, pp. 1012-1038.
Pamplona V. F. et al., "Tailored Displays to Compensate for Visual Aberrations," ACM Transactions on Graphics (TOG), Jul. 2012 Article No. 81, https://doi.org/10.1145/2185520.2185577.
Pamplona V. F., Thesis (Ph.D.)—Universidade Federal do Rio Grande do Sul. Programa de Pós-Graduação em Computação, Porto Alegre, BR-RS, 2012. Advisor: Manuel Menezes de Oliveira Neto.
Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.
Written Opinion of the International Searching Authority received in International Application No. PCT/CA2016/051006 dated Sep. 30, 2016 in 9 pages.

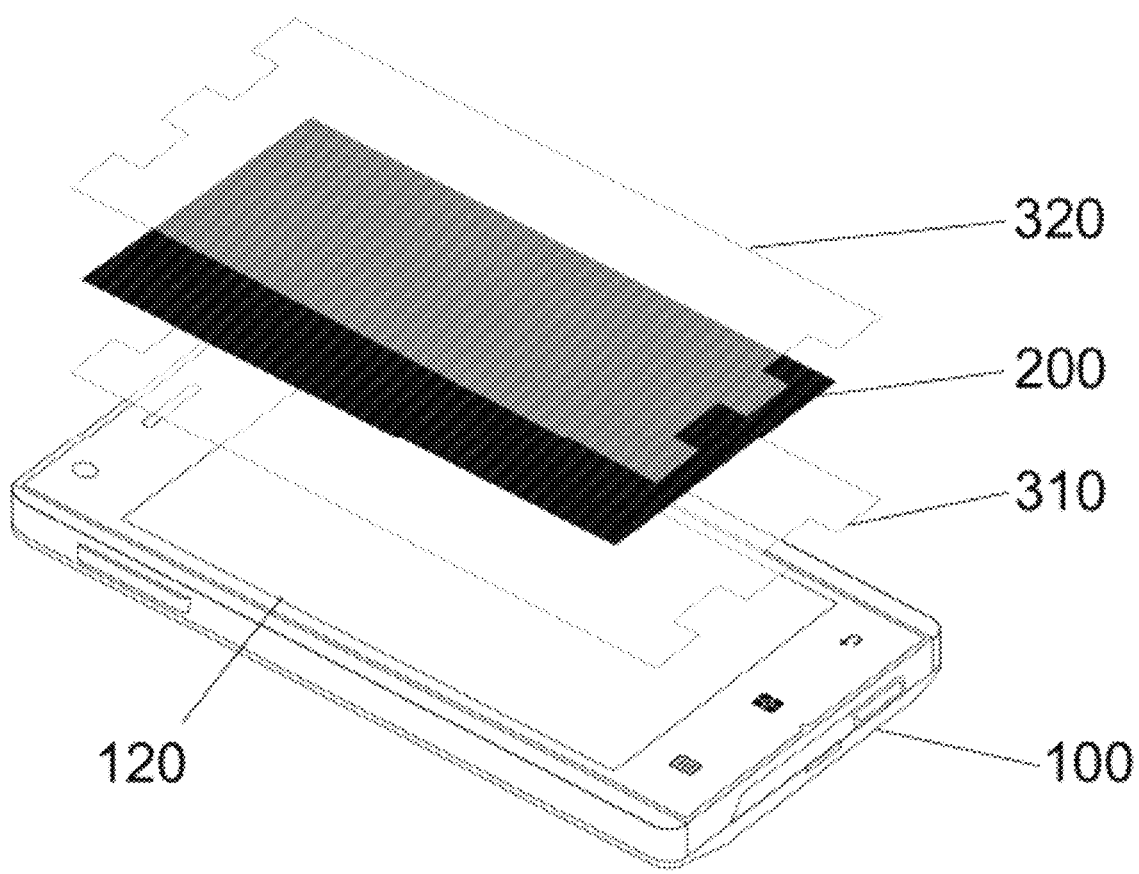
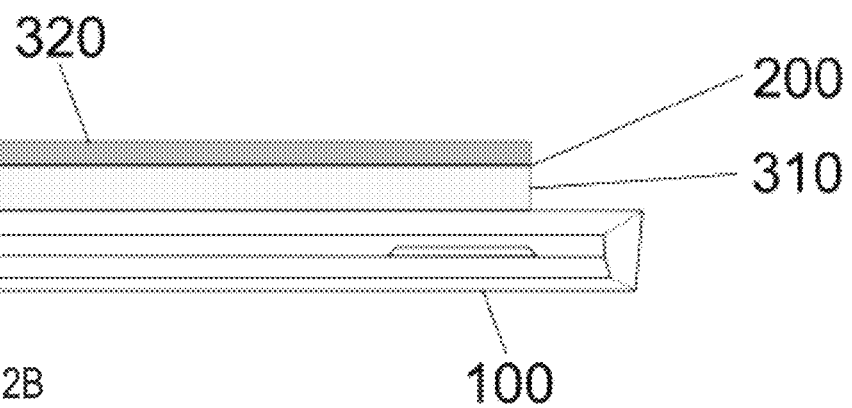

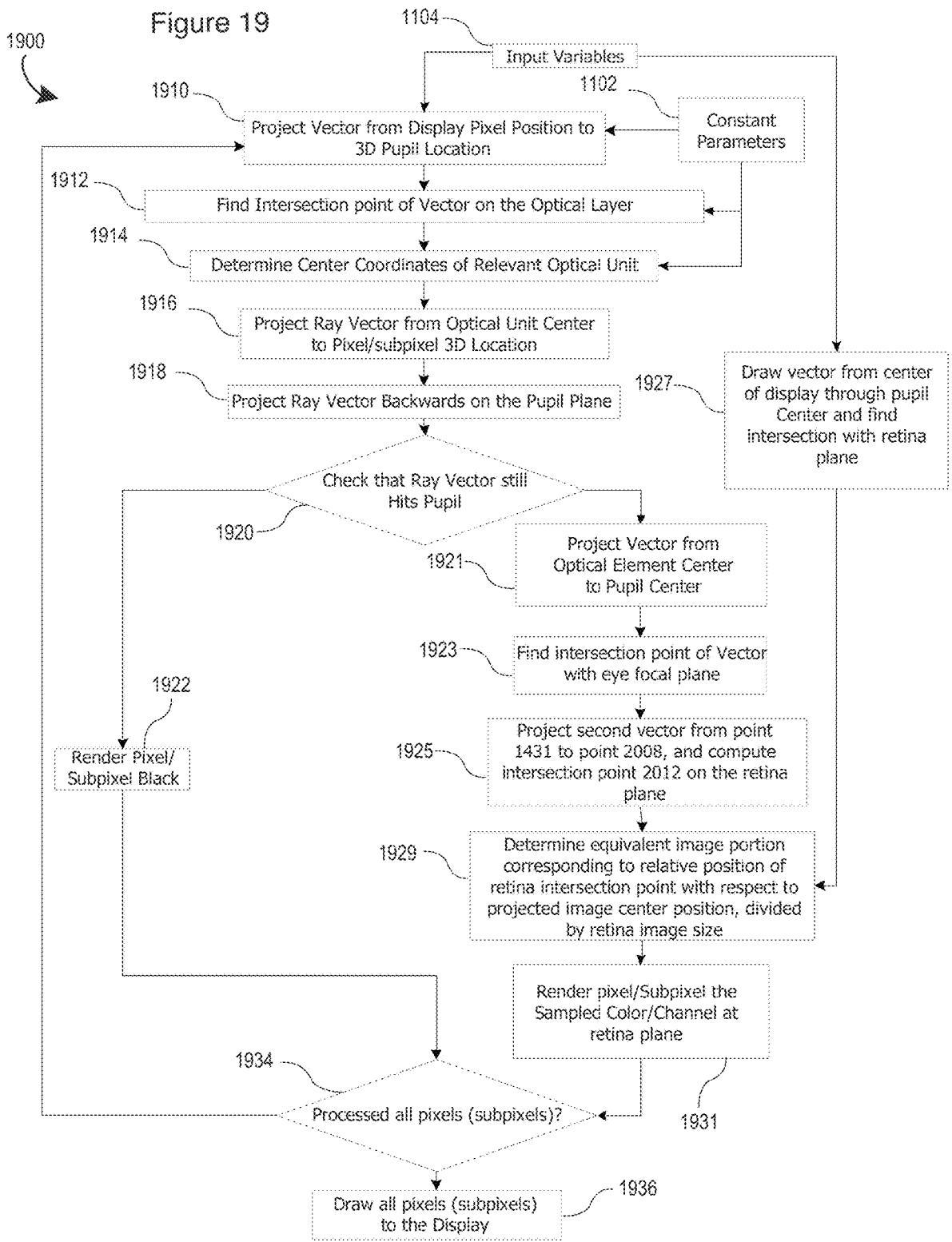

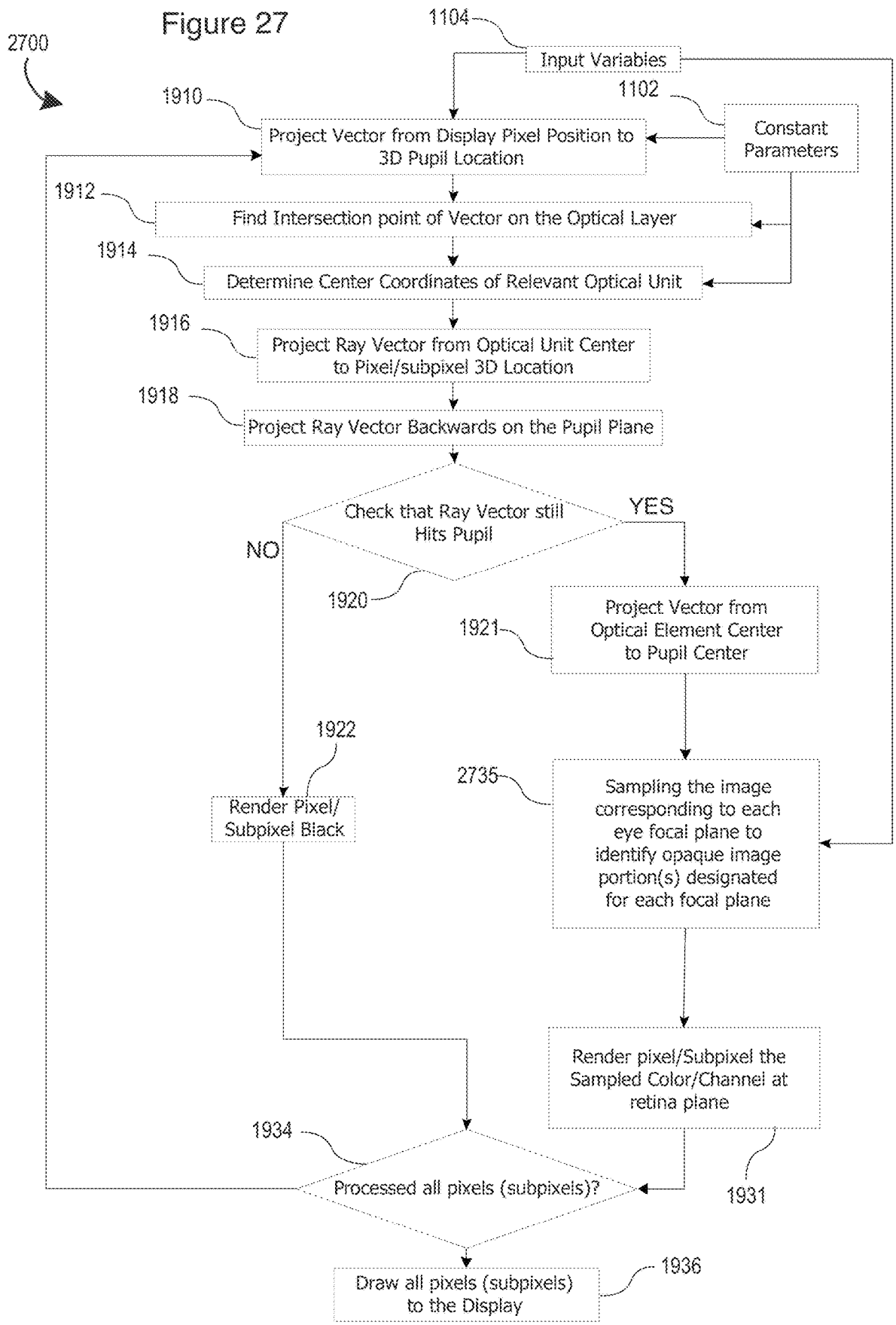

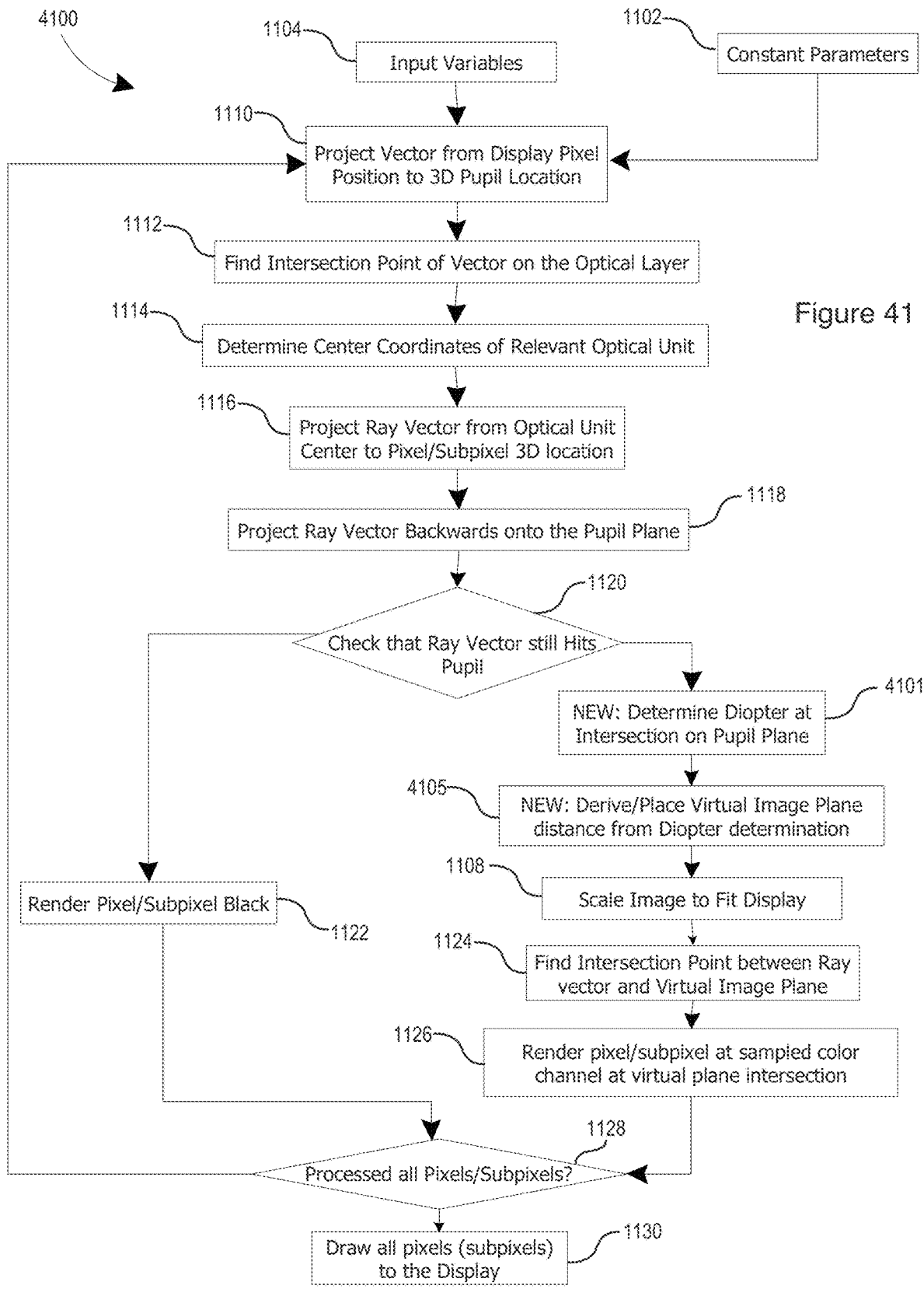

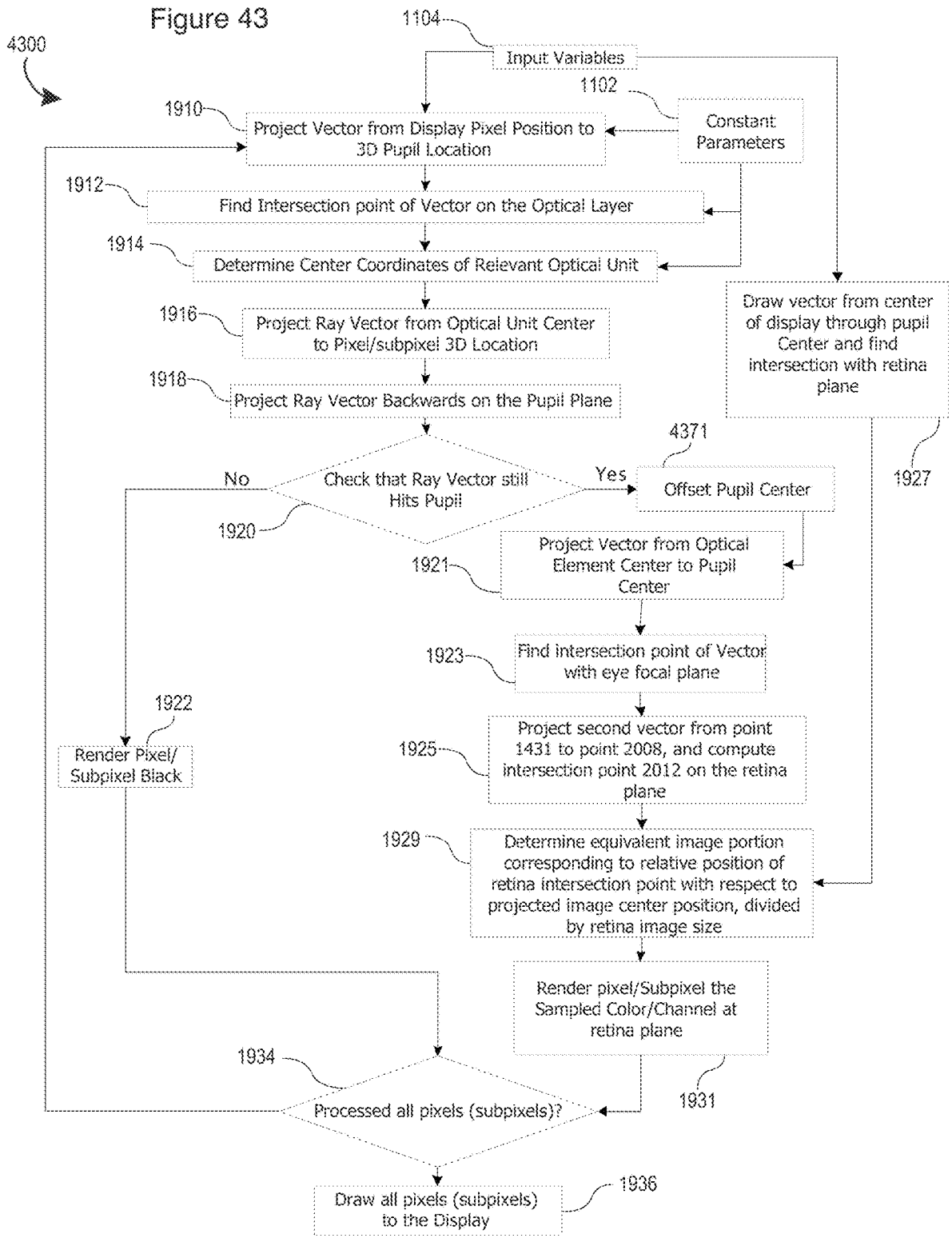

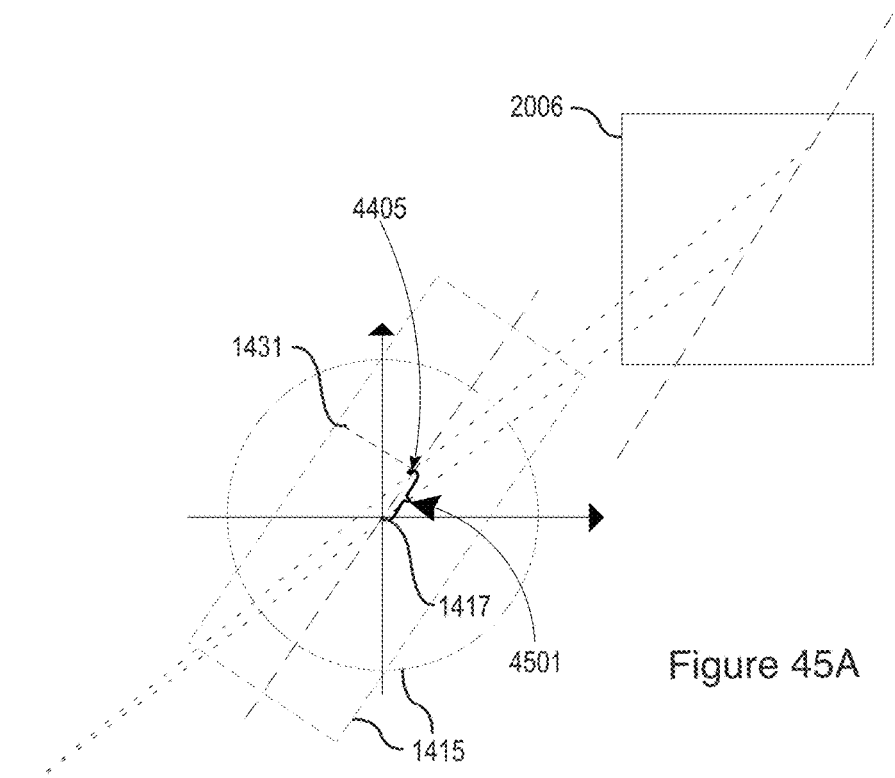
Figure 45A
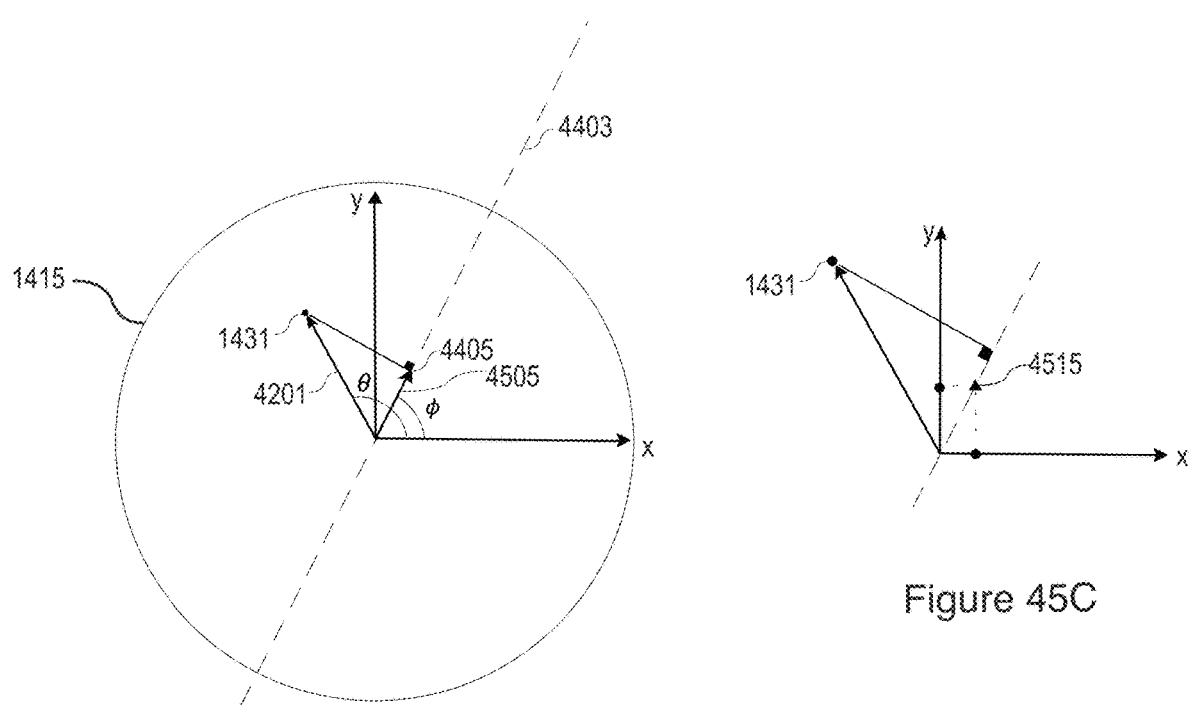
Figure 45B
Figure 45C

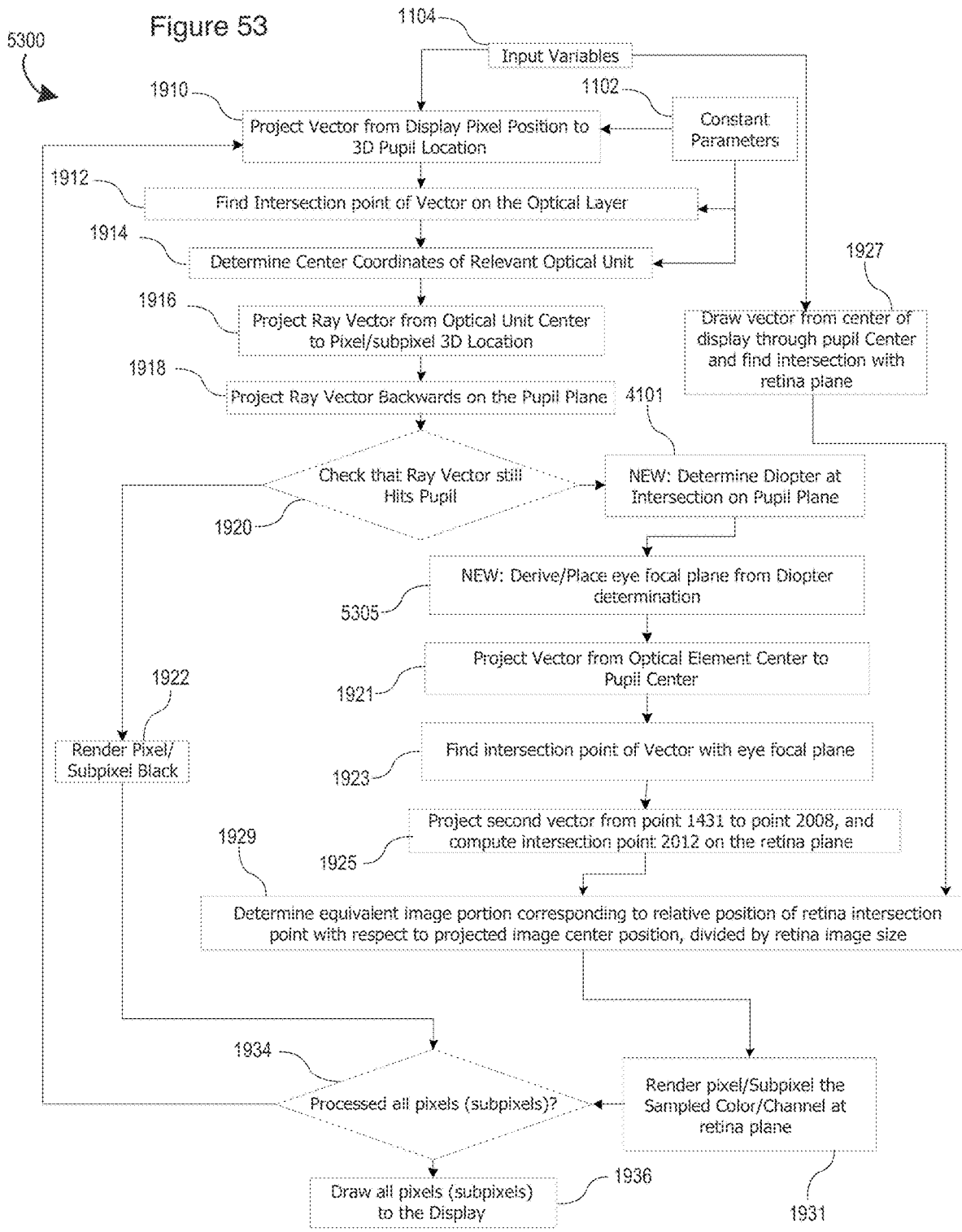

LIGHT FIELD DISPLAY, ADJUSTED PIXEL RENDERING METHOD THEREFOR, AND ADJUSTED VISION PERCEPTION SYSTEM AND METHOD USING SAME ADDRESSING ASTIGMATISM OR SIMILAR CONDITIONS

CROSS REFERENCE TO RELATED APPLICATIONS

This application is a continuation-in-part of U.S. patent application Ser. No. 16/854,787 filed Apr. 21, 2020, which is a continuation-in-part of U.S. patent application Ser. No. 16/810,143 filed Mar. 5, 2020, which is a continuation-in-part of U.S. patent application Ser. No. 16/551,572 filed Aug. 26, 2019, a continuation-in-part of International Application No. PCT/IB2019/058955 filed Oct. 21, 2019, and a continuation-in-part of U.S. patent application Ser. No. 16/569,137 filed Sep. 12, 2019, the latter of which is a continuation of U.S. patent application Ser. No. 16/510,673 filed Jul. 12, 2019, which is a continuation of U.S. patent application Ser. No. 16/259,845 filed Jan. 28, 2019 and which claims priority to Canadian Patent Application No. 3,021,636 filed Oct. 22, 2018; U.S. patent application Ser. No. 16/854,787 also claims priority to U.S. Provisional Patent Application No. 62/929,639 filed Nov. 1, 2019, the entire disclosure of each of which is hereby incorporated herein by reference.

FIELD OF THE DISCLOSURE

The present disclosure relates to digital displays, and in particular, to a light field display, and adjusted pixel rendering method and computer-readable medium therefor, and adjusted vision perception system and method using same.

BACKGROUND

Individuals routinely wear corrective lenses to accommodate for reduced vision acuity in consuming images and/or information rendered, for example, on digital displays provided, for example, in day-to-day electronic devices such as smartphones, smart watches, electronic readers, tablets, laptop computers and the like, but also provided as part of vehicular dashboard displays and entertainment systems, to name a few examples. The use of bifocals or progressive corrective lenses is also commonplace for individuals suffering from near and farsightedness.

The operating systems of current electronic devices having graphical displays offer certain "Accessibility" features built into the software of the device to attempt to provide users with reduced vision the ability to read and view content on the electronic device. Specifically, current accessibility options include the ability to invert images, increase the image size, adjust brightness and contrast settings, bold text, view the device display only in grey, and for those with legal blindness, the use of speech technology. These techniques focus on the limited ability of software to manipulate display images through conventional image manipulation, with limited success.

The use of 4D light field displays with lenslet arrays or parallax barriers to correct visual aberrations have since been proposed by Pamplona et al. (PAMPLONA, V., OLIVEIRA, M., ALIAGA, D., AND RASKAR, R. 2012. "Tailored displays to compensate for visual aberrations." ACM Trans. Graph. (SIGGRAPH) 31.). Unfortunately, conventional light field displays as used by Pamplona et al. are subject to a spatio-angular resolution trade-off; that is, an increased angular resolution decreases the spatial resolution. Hence, the viewer sees a sharp image but at the expense of a significantly lower resolution than that of the screen. To mitigate this effect, Huang et al. (see, HUANG, F.-C., AND BARSKY, B. 2011. A framework for aberration compensated displays. Tech. Rep. UCB/EEC S-2011-162, University of California, Berkeley, December; and HUANG, F.-C., LANMAN, D., BARSKY, B. A., AND RASKAR, R. 2012. Correcting for optical aberrations using multi layer displays. ACM Trans. Graph. (SiGGRAPH Asia) 31, 6, 185:1-185:12) proposed the use of multilayer display designs together with prefiltering. The combination of prefiltering and these particular optical setups, however, significantly reduces the contrast of the resulting image.

Finally, in U.S. Patent Application Publication No. 2016/0042501 and Fu-Chung Huang, Gordon Wetzstein, Brian A. Barsky, and Ramesh Raskar. "Eyeglasses-free Display: Towards Correcting Visual Aberrations with Computational Light Field Displays". ACM Transaction on Graphics, 33(4), August 2014, the entire contents of each of which are hereby incorporated herein by reference, the combination of viewer-adaptive pre-filtering with off-the-shelf parallax barriers has been proposed to increase contrast and resolution, at the expense however, of computation time and power.

This background information is provided to reveal information believed by the applicant to be of possible relevance. No admission is necessarily intended, nor should be construed, that any of the preceding information constitutes prior art.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the disclosure. This summary is not an extensive overview of the disclosure. It is not intended to restrict key or critical elements of the embodiments of the disclosure or to delineate their scope beyond that which is explicitly or implicitly described by the following description and claims.

A need exists for a light field display, adjusted pixel rendering method therefor, and adjusted vision perception system and method using same, that overcome some of the drawbacks of known techniques, for example that addresses astigmatism or similar conditions, or at least, provide a useful alternative thereto. Some aspects of disclosure provide embodiments of such systems, methods, and displays.

In accordance with one aspect, there is provided a device operable to dynamically adjust user perception of an input image, the device comprising: an array of digital display pixels; a corresponding array of light field shaping elements (LFSEs) shaping a light field emanating from said pixels; and a hardware processor operable on pixel data for the input image to output adjusted image pixel data to be rendered via said LFSEs to dynamically adjust perception of the input image as so rendered to at least partially accommodate a designated visual acuity accommodation defined by a designated variable optical vision parameter that varies across user pupil locations, by digitally: for each given pixel, defining a corresponding location on an adjusted image surface as a function of a direction of a given light field emanated by said given pixel given a corresponding LFSE and said designated variable optical vision parameter for a given pupil location intersected by said given light field; associating an adjusted image pixel value with said given pixel given said corresponding location on said adjusted image surface; and rendering each said given pixel according to said adjusted pixel value associated therewith, thereby perceptively rendering a perceptively adjusted version of the input image that at least partially accommodates said designated visual acuity accommodation.

In accordance with another aspect, there is provided a computer-implemented method, automatically implemented by one or more digital processors, to dynamically adjust user perception of an input image to be rendered by an array of digital display pixels via a corresponding array of light field shaping elements (LFSE) to at least partially accommodate a designated visual acuity accommodation defined by a designated variable optical vision parameter that varies across user pupil locations, the method comprising, for each given pixel: defining a corresponding location on an adjusted image surface as a function of a direction of a given light field emanated by said given pixel given a corresponding LFSE and said designated variable optical vision parameter for a given pupil location intersected by said given light field; associating an adjusted image pixel value with said given pixel given said corresponding location on said adjusted image surface; and rendering each said given pixel according to said adjusted pixel value associated therewith, thereby perceptively rendering a perceptively adjusted version of the input image that at least partially accommodates said designated visual acuity accommodation.

In accordance with another aspect, there is provided a non-transitory computer-readable medium comprising digital instructions to be implemented by one or more digital processors to automatically adjust perception of an input to be rendered via an array of digital display pixels and a corresponding array of light field shaping elements (LFSE) to at least partially accommodate a designated visual acuity accommodation defined by a designated variable optical vision parameter that varies across user pupil locations, by, for each given pixel, digitally: defining a corresponding location on an adjusted image surface as a function of a direction of a given light field emanated by said given pixel given a corresponding LFSE and said designated variable optical vision parameter for a given pupil location intersected by said given light field; and associating an adjusted image pixel value with said given pixel given said corresponding location on said adjusted image surface for perceptively rendering a perceptively adjusted version of the input image that at least partially accommodates said designated visual acuity accommodation.

In accordance with another aspect, there is provided a subjective eye test device comprising: an array of digital display pixels; a corresponding array of light field shaping elements (LFSEs) shaping a light field emanating from said pixels; and a hardware processor operable on pixel data for a defined optotype to output adjusted image pixel data to be rendered via said LFSEs to dynamically adjust perception of said defined optotype as so rendered to at least partially accommodate a designated visual acuity accommodation by, for each given pixel, digitally: projecting a given ray trace between said given pixel and a given pupil location on a user pupil given a direction of a light field emanated by said given pixel given a corresponding LFSE; identifying a designated optical vision parameter for said given pupil location given said designated visual acuity accommodation; defining an adjusted image location on an adjusted image surface corresponding with said given pixel as a function of said designated optical vision parameter for said given pupil location; associating an adjusted image pixel value designated for said adjusted image location with said given pixel; and rendering each said given pixel according to said adjusted pixel value associated therewith, thereby perceptively rendering a perceptively adjusted version of said defined optotype on said adjusted image surface that at least partially accommodates said designated visual acuity accommodation; and adjusting said designated optical vision parameter to accommodate for a distinct visual acuity accommodation until an optimal visual acuity accommodation is identified.

In one embodiment, for at least some said given pixel, said adjusted image surface comprises a respective virtual image plane virtually positioned relative to the digital display pixels at a designated distance from said user pupil and corresponding with a respective said designated optical vision parameter identified for said given pupil location, and wherein said hardware processor is further operable to digitally map the defined optotype on said respective virtual image plane and associate said adjusted image pixel value based on said mapping.

In one embodiment, the adjusted image location is defined by an intersection on said respective virtual image plane of a virtual image vector linking said given pixel and a center position of said corresponding LFSE.

In one embodiment, the designated distance is representative of a pupil-location-dependent minimum reading distance corresponding with said designated optical vision parameter for said give pupil location.

In one embodiment, the adjusted image surface comprises a user retinal plane; and wherein said defining said adjusted image location comprises digitally redirecting said given ray trace at said given pupil location according to said designated optical vision parameter so to intersect said retinal plane at said adjusted image location, wherein said hardware processor is further operable to digitally map the defined optotype on said user retinal plane and associate said adjusted image pixel value based on said mapping.

In one embodiment, the designated optical vision parameter comprises a cylindrical optical power value that varies as a function of said given pupil location relative to a designated cylinder axis defined for said designated visual acuity accommodation.

In one embodiment, the designated optical vision parameter is representative of a pupil-position-dependent total dioptric power defined for said given pupil location.

In one embodiment, each said designated visual acuity accommodation is defined by a designated optical vision parameter comprising a spherical power, a cylindrical power and an optical axis parameter, and wherein said adjusting comprises iteratively optimizing for each of said spherical power, said cylindrical power and said optical axis parameter sequentially.

In one embodiment, the adjusting comprises adjusting said spherical power parameter until an optimal spherical correction is subjectively identified, followed by iteratively optimizing said optical axis parameter until an optimal optical axis correction is subjectively identified, followed by iteratively optimizing said cylindrical power parameter until an optical cylindrical power correction is subjectively identified.

In one embodiment, the device is operable to dynamically adjust user perception of distinct image portions by: digitally processing each given image portion to be perceptively rendered according to distinct designated visual acuity accommodations; and comparatively adjusting said distinct designated visual acuity accommodations until said optimal visual acuity accommodation is identified.

In accordance with another aspect, there is provided a device operable to dynamically adjust user perception of an input image, the device comprising: an array of digital display pixels; a corresponding array of light field shaping elements (LFSEs) shaping a light field emanating from said pixels; and a hardware processor operable on pixel data for the input image to output adjusted image pixel data to be rendered via said LFSEs to dynamically adjust perception of the input image as so rendered to at least partially accommodate a designated visual acuity accommodation by, for each given pixel, digitally: projecting a given ray trace between said given pixel and a given pupil location on a user pupil given a direction of a light field emanated by said given pixel given a corresponding LFSE; identifying a designated optical vision parameter for said given pupil location given said designated visual acuity accommodation; defining an adjusted image location on an adjusted image surface corresponding with said given pixel as a function of said designated optical vision parameter for said given pupil location; associating an adjusted image pixel value designated for said adjusted image location with said given pixel; and rendering each said given pixel according to said adjusted pixel value associated therewith, thereby perceptively rendering a perceptively adjusted version of the input image on said adjusted image surface that at least partially accommodates said designated visual acuity accommodation.

In one embodiment, the designated visual acuity accommodation comprises a spherical optical power correction, a cylindrical optical power correction and a cylindrical axis correction, and wherein said designated optical vision parameter is respectively designated as a function of said designated visual acuity accommodation for each said given pupil location.

In one embodiment, for at least some said given pixel, said adjusted image surface comprises a respective virtual image plane virtually positioned relative to the digital display pixels at a designated distance from said user pupil and corresponding with a respective said designated optical vision parameter identified for said given pupil location, and wherein said hardware processor is further operable to digitally map the input image on said respective virtual image plane and associate said adjusted image pixel value based on said mapping.

In one embodiment, the adjusted image surface comprises a user retinal plane; and wherein said defining said adjusted image location comprises digitally redirecting said given ray trace at said given pupil location according to said designated optical vision parameter so to intersect said retinal plane at said adjusted image location, wherein said hardware processor is further operable to digitally map the input image on said user retinal plane and associate said adjusted image pixel value based on said mapping.

In one embodiment, the redirecting comprises: deriving from said given pupil location and said designated optical vision parameter defined therefor, an offset pupil location through which a corresponding ray trace is estimated to propagate substantially undeviated by an eye to a corresponding eye focal point on a user eye focal plane, wherein said offset pupil location is digitally calculated as a function of said spherical optical power parameter, said cylindrical optical power parameter and said cylindrical optical axis parameter; and redirecting said given ray trace toward said eye focal point so to intersect said user retinal plane at said adjusted image location.

In accordance with another aspect, there is provided a computer-implemented method, automatically implemented by one or more digital processors, to dynamically adjust user perception of an input image to be rendered by an array of digital display pixels via a corresponding array of light field shaping elements (LFSE) to at least partially accommodate a designated visual acuity accommodation, the method comprising, for each given pixel: projecting a given ray trace between said given pixel and a given pupil location on a user pupil given a direction of a light field emanated by said given pixel given a corresponding LFSE; identifying a designated optical vision parameter for said given pupil location given said designated visual acuity accommodation; defining an adjusted image location on an adjusted image surface corresponding with said given pixel as a function of said designated optical vision parameter for said given pupil location; associating an adjusted image pixel value designated for said adjusted image location with said given pixel; and rendering each said given pixel according to said adjusted pixel value associated therewith, thereby perceptively rendering a perceptively adjusted version of the input image on said adjusted image surface that at least partially accommodates said designated visual acuity accommodation.

In one embodiment, the designated visual acuity accommodation comprises a spherical optical power correction, a cylindrical optical power correction and a cylindrical axis correction, and wherein said designated optical vision parameter is respectively designated as a function of said designated visual acuity accommodation for each said given pupil location.

In one embodiment, for at least some said given pixel, said adjusted image surface comprises a respective virtual image plane virtually positioned relative to the digital display pixels at a designated distance from said user pupil and corresponding with a respective said designated optical vision parameter identified for said given pupil location, and wherein the method further comprises digitally mapping the input image on said respective virtual image plane and associating said adjusted image pixel value based on said mapping.

In one embodiment, the method further comprises digitally mapping the input image on said respective virtual image plane and associating said adjusted image pixel value based on said mapping, wherein a mapping area of at least some said respective virtual image plane is defined by a non-rectangular convex quadrilateral area.

In one embodiment, the adjusted image surface comprises a user retinal plane; and wherein said defining said adjusted image location comprises digitally redirecting said given ray trace at said given pupil location according to said designated optical vision parameter so to intersect said retinal plane at said adjusted image location, wherein the method further comprises digitally mapping the input image on said user retinal plane and associating said adjusted image pixel value based on said mapping.

In one embodiment, the redirecting comprises: deriving from said given pupil location and said designated optical vision parameter defined therefor, an offset pupil location through which a corresponding ray trace is estimated to propagate substantially undeviated to a corresponding eye focal point on a user eye focal plane, wherein said offset pupil location is digitally calculated as a function of said spherical optical power parameter, said cylindrical optical power parameter and said cylindrical optical axis parameter;

and redirecting said given ray trace toward said eye focal point so to intersect said user retinal plane at said adjusted image location.

In one embodiment, the method further comprises adjusting said designated optical vision parameter to accommodate for a distinct visual acuity accommodation until an optimal visual acuity accommodation is identified.

In one embodiment, the designated visual acuity accommodation is defined by a designated optical vision parameter comprising a spherical power, a cylindrical power and an optical axis parameter, and wherein said adjusting comprises iteratively optimizing for each of said spherical power, said cylindrical power and said optical axis parameter sequentially.

In one embodiment, the adjusting comprises adjusting said spherical power parameter until an optimal spherical correction is subjectively identified, followed by iteratively optimizing said optical axis parameter until an optimal optical axis correction is subjectively identified, followed by iteratively optimizing said cylindrical power parameter until an optical cylindrical power correction is subjectively identified.

In accordance with another aspect, there is provided a non-transitory computer-readable medium comprising digital instructions to be implemented by one or more digital processors to automatically adjust perception of an input to be rendered via an array of digital display pixels and a corresponding array of light field shaping elements (LFSE) to at least partially accommodate a designated visual acuity accommodation, by, for each given pixel, digitally: projecting a given ray trace between said given pixel and a given pupil location on a user pupil given a direction of a light field emanated by said given pixel given a corresponding LFSE; identifying a designated optical vision parameter for said given pupil location given said designated visual acuity accommodation; defining an adjusted image location on an adjusted image surface corresponding with said given pixel as a function of said designated optical vision parameter for said given pupil location; associating an adjusted image pixel value designated for said adjusted image location with said given pixel for perceptively rendering a perceptively adjusted version of the input on said adjusted image surface that at least partially accommodates said designated visual acuity accommodation.

In one embodiment, for at least some said given pixel, said adjusted image surface comprises a respective virtual image plane virtually positioned relative to the digital display pixels at a designated distance from said user pupil and corresponding with a respective said designated optical vision parameter identified for said given pupil location, and wherein the method further comprises digitally mapping the input on said respective virtual image plane and associating said adjusted image pixel value based on said mapping.

In one embodiment, a mapping area of at least some said respective virtual image plane is defined by a non-rectangular convex quadrilateral area.

In one embodiment, the adjusted image surface comprises a user retinal plane; and wherein said defining said adjusted image location comprises digitally redirecting said given ray trace at said given pupil location according to said designated optical vision parameter so to intersect said retinal plane at said adjusted image location, wherein the non-transitory computer-readable medium further comprises instructions for digitally mapping the input image on said user retinal plane and associating said adjusted image pixel value based on said mapping.

In one embodiment, the redirecting comprises: defining a corresponding ray trace from said given LFSE estimated to propagate substantially undeviated to a corresponding eye focal point on a user eye focal plane; and redirecting said given ray trace toward said eye focal point so to intersect said user retinal plane at said adjusted image location.

In one embodiment, the redirecting comprises: deriving from said given pupil location and said designated optical vision parameter defined therefor, an offset pupil location through which a corresponding ray trace is estimated to propagate substantially undeviated to a corresponding eye focal point on a user eye focal plane, wherein said offset pupil location is digitally calculated, at least in part, as a function of a cylindrical optical focusing parameter and a cylindrical optical axis parameter; and redirecting said given ray trace toward said eye focal point so to intersect said user retinal plane at said adjusted image location.

In accordance with another aspect, there is provided a computer-implemented method, automatically implemented by one or more digital processors, to adjust perception of an input to be rendered via a set of pixels and a corresponding array of light field shaping elements (LFSE), the method comprising: digitally mapping the input image on a designated adjusted image surface designated to provide a designated perception adjustment, wherein said adjusted image surface is at an angle relative to said set of pixels; for at least some of said pixels, digitally: projecting an adjusted ray trace linking a given pixel and a pupil location given a corresponding LFSE, to intersect said adjusted image surface at a given adjusted surface location given said angle; and associating an adjusted pixel value designated for said given adjusted surface location with said given pixel given said mapping for rendering a perceptively adjusted version of the input.

In one embodiment, the adjusted image surface comprises a virtual image plane virtually positioned relative to the pixels at a designated distance from said pupil location, and wherein a mapping area of said virtual image plane is defined by a non-rectangular convex quadrilateral area given said angle.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIGS. 2A and 2B are exploded and side views, respectively, of an assembly of a light field display for an electronic device, in accordance with one embodiment;

FIG. 19 is process flow diagram of an illustrative ray-tracing rendering process, in accordance with another embodiment;

FIG. 27 is a process flow diagram of an illustrative ray-tracing rendering process for rendering a light field originating from multiple distinct image planes, in accordance with one embodiment;

FIG. 41 is a process flow diagram of an illustrative ray-tracing rendering process for astigmatism compensation, in accordance with one embodiment;

FIG. 43 is a process flow diagram of an illustrative ray-tracing rendering process for astigmatism compensation, in accordance with one embodiment;

FIGS. 45A to 45C are schematic diagrams illustrating certain process steps of FIG. 43, in accordance with one embodiment;

FIG. 53 is a process flow diagram of another illustrative ray-tracing rendering process for astigmatism compensation, in accordance with one embodiment.

Figure 1:
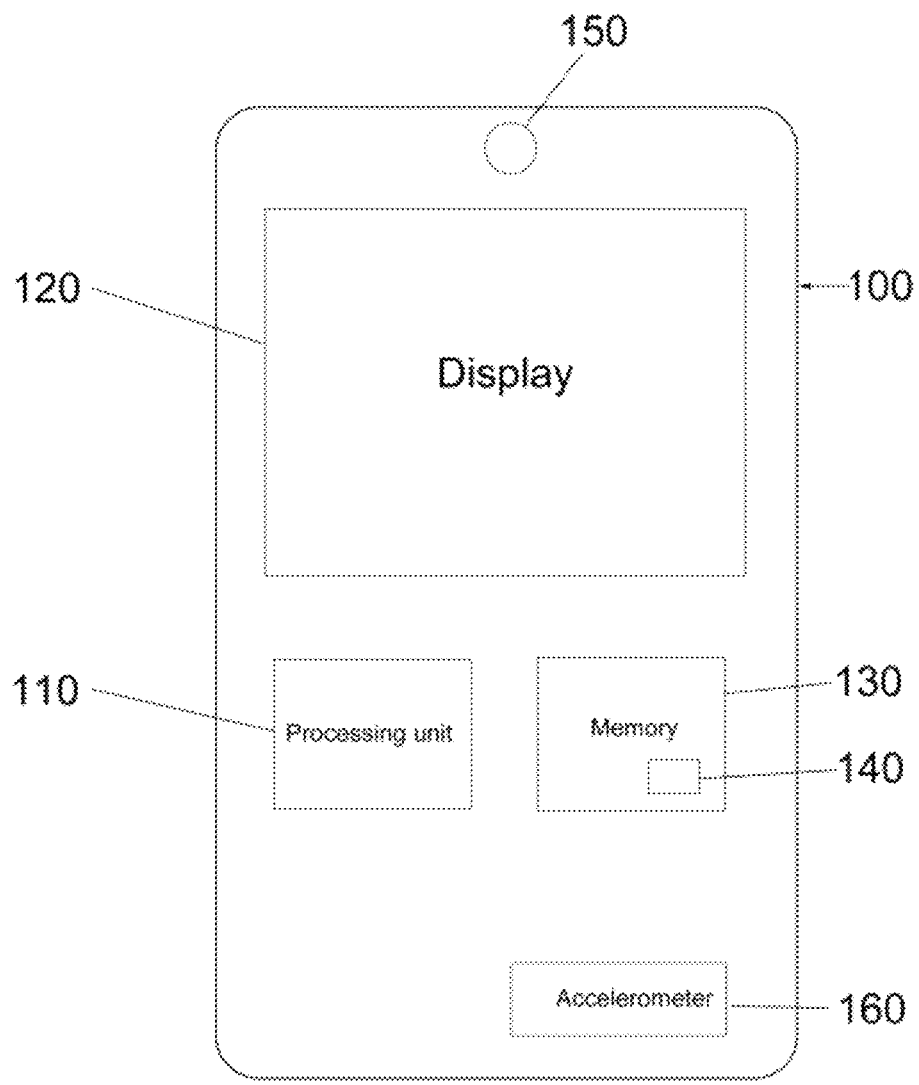
FIG. 1 is a diagrammatical view of an electronic device having a digital display, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The systems and methods described herein provide, in accordance with different embodiments, different examples of a light field display, adjusted pixel rendering method therefor, and adjusted vision perception system and method using same. For example, some of the herein-described embodiments provide improvements or alternatives to current light field display technologies, for instance, providing compensation for astigmatism or similar conditions. These and other such applications will be described in further detail below.

As noted above, the devices, displays and methods described herein may allow a user's perception of one or more input images (or input image portions), where each image or image portion is virtually located at a distinct image plane/depth location, to be adjusted or altered using the light field display.

Some of the herein described embodiments provide for digital display devices, or devices encompassing such displays, for use by users having reduced visual acuity, whereby images ultimately rendered by such devices can be dynamically processed to accommodate the user's reduced visual acuity so that they may consume rendered images without the use of corrective eyewear, as would otherwise be required. As noted above, embodiments are not to be limited as such as the notions and solutions described herein may also be applied to other technologies in which a user's perception of an input image to be displayed can be altered or adjusted via the light field display. Conversely, similar implementation of the herein described embodiments can allow for implementation of digitally adaptive vision tests such that individuals with such reduced visual acuity can be exposed to distinct perceptively adjusted versions of an input image(s) to subjectively ascertain a potentially required or preferred vision correction.

Generally, digital displays as considered herein will comprise a set of image rendering pixels and a corresponding set of light field shaping elements that at least partially govern a light field emanated thereby to produce a perceptively adjusted version of the input image, notably distinct perceptively adjusted portions of an input image or input scene, which may include distinct portions of a same image, a same 2.5D/3D scene, or distinct images (portions) associated with different image depths, effects and/or locations and assembled into a combined visual input. For simplicity, the following will generally consider distinctly addressed portions or segments as distinct portions of an input image, whether that input image comprises a singular image having distinctly characterized portions, a digital assembly of distinctly characterized images, overlays, backgrounds, foregrounds or the like, or any other such digital image combinations.

In some examples, light field shaping elements may take the form of a light field shaping layer or like array of optical elements to be disposed relative to the display pixels in at least partially governing the emanated light field. As described in further detail below, such light field shaping layer elements may take the form of a microlens and/or pinhole array, or other like arrays of optical elements, or again take the form of an underlying light shaping layer, such as an underlying array of optical gratings or like optical elements operable to produce a directional pixelated output.

Within the context of a light field shaping layer, as described in further detail below in accordance with some embodiments, the light field shaping layer can be disposed at a pre-set distance from the pixelated display so to controllably shape or influence a light field emanating therefrom. For instance, each light field shaping layer can be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping elements and/or layer (e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping element and/or layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer and/or elements, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Accordingly, a given device may be adapted to compensate for different visual acuity levels and thus accommodate different users and/or uses. For instance, a particular device may be configured to implement and/or render an interactive graphical user interface (GUI) that incorporates a dynamic vision correction scaling function that dynamically adjusts one or more designated vision correction parameter(s) in real-time in response to a designated user interaction therewith via the GUI. For example, a dynamic vision correction scaling function may comprise a graphically rendered scaling function controlled by a (continuous or discrete) user slide motion or like operation, whereby the GUI can be configured to capture and translate a user's given slide motion operation to a corresponding adjustment to the designated vision correction parameter(s) scalable with a degree of the user's given slide motion operation. These and other examples are described in Applicant's co-pending U.S. patent application Ser. No. 15/246,255, the entire contents of which are hereby incorporated herein by reference.

With reference to FIG. 1, and in accordance with one embodiment, a digital display device, generally referred to using the numeral 100, will now be described. In this example, the device 100 is generally depicted as a smartphone or the like, though other devices encompassing a graphical display may equally be considered, such as tablets, e-readers, watches, televisions, GPS devices, laptops, desktop computer monitors, televisions, smart televisions, handheld video game consoles and controllers, vehicular dashboard and/or entertainment displays, and the like.

In the illustrated embodiment, the device 100 comprises a processing unit 110, a digital display 120, and internal memory 130. Display 120 can be an LCD screen, a monitor, a plasma display panel, an LED or OLED screen, or any other type of digital display defined by a set of pixels for rendering a pixelated image or other like media or information. Internal memory 130 can be any form of electronic storage, including a disk drive, optical drive, read-only memory, random-access memory, or flash memory, to name a few examples. For illustrative purposes, memory 130 has stored in it vision correction application 140, though various methods and techniques may be implemented to provide computer-readable code and instructions for execution by the processing unit in order to process pixel data for an image to be rendered in producing corrected pixel data amenable to producing a corrected image accommodating the user's reduced visual acuity (e.g. stored and executable image correction application, tool, utility or engine, etc.).

Other components of the electronic device 100 may optionally include, but are not limited to, one or more rear and/or front-facing camera(s) 150, an accelerometer 160 and/or other device positioning/orientation devices capable of determining the tilt and/or orientation of electronic device 100, and the like.

For example, the electronic device 100, or related environment (e.g. within the context of a desktop workstation, vehicular console/dashboard, gaming or e-learning station, multimedia display room, etc.) may include further hardware, firmware and/or software components and/or modules to deliver complementary and/or cooperative features, functions and/or services. For example, in some embodiment, and as will be described in greater detail below, a pupil/eye tracking system may be integrally or cooperatively implemented to improve or enhance corrective image rending by tracking a location of the user's eye(s)/pupil(s) (e.g. both or one, e.g. dominant, eye(s)) and adjusting light field corrections accordingly. For instance, the device 100 may include, integrated therein or interfacing therewith, one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying a tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). In the context of a mobile device, such as a mobile phone, such eye/pupil tracking hardware/software may be integral to the device, for instance, operating in concert with integrated components such as one or more front facing camera(s), onboard IR/NIR light source(s) and the like. In other user environments, such as in a vehicular environment, eye/pupil tracking hardware may be further distributed within the environment, such as dash, console, ceiling, windshield, mirror or similarly-mounted camera(s), light sources, etc.

With reference to FIGS. 2A and 2B, the electronic device 100, such as that illustrated in FIG. 1, is further shown to include a light field shaping layer (LFSL) 200 overlaid atop a display 120 thereof and spaced therefrom via a transparent spacer 310 or other such means as may be readily apparent to the skilled artisan. An optional transparent screen protector 320 is also included atop the layer 200.

For the sake of illustration, the following embodiments will be described within the context of a light field shaping layer defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources (e.g. directional light sources and/or backlit to integrated optical grating array) or like component.

Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display, which will be referred to now as the 'virtual image'. As noted in the examples below, in some embodiments, light field rendering may be adjusted to effectively generate a virtual image on a virtual image plane that is set at a designated distance from an input user pupil location, for example, so to effective push back, or move forward, a perceived image relative to the display device in accommodating a user's reduced visual acuity (e.g. minimum or maximum viewing distance). In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 3A:
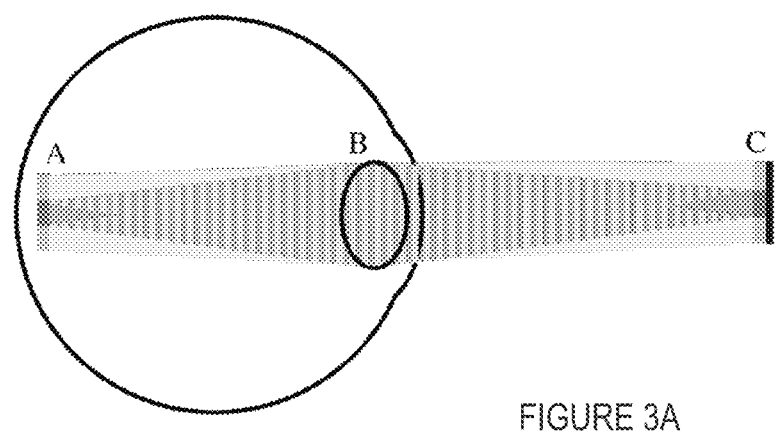
FIGS. 3A, 3B and 3C schematically illustrate normal vision, blurred vision, and corrected vision in accordance with one embodiment, respectively.
Figure 3B:
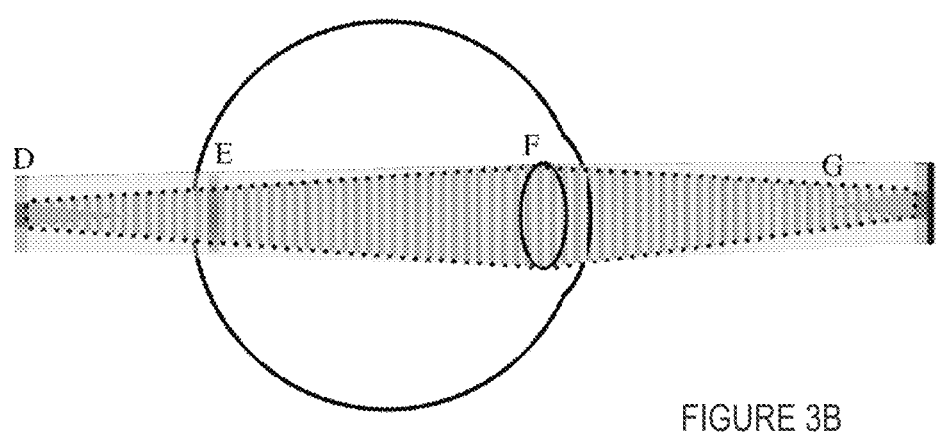

In one example, to apply this technology to vision correction, consider first the normal ability of the lens in an eye, as schematically illustrated in FIG. 3A, where, for normal vision, the image is to the right of the eye (C) and is projected through the lens (B) to the retina at the back of the eye (A). As comparatively shown in FIG. 3B, the poor lens shape and inability to accommodate (F) in presbyopia causes the image to be focused past the retina (D) forming a blurry image on the retina (E). The dotted lines outline the path of a beam of light (G). Naturally, other optical aberrations present in the eye will have different impacts on image formation on the retina. To address these aberrations, a light field display (K), in accordance with some embodiments, projects the correct sharp image (H) on the retina for an eye with a crystalline lens which otherwise could not accommodate sufficiently to produce a sharp image. The other two light field pixels (I) and (J) are drawn lightly, but would otherwise fill out the rest of the image.

Figure 3C:
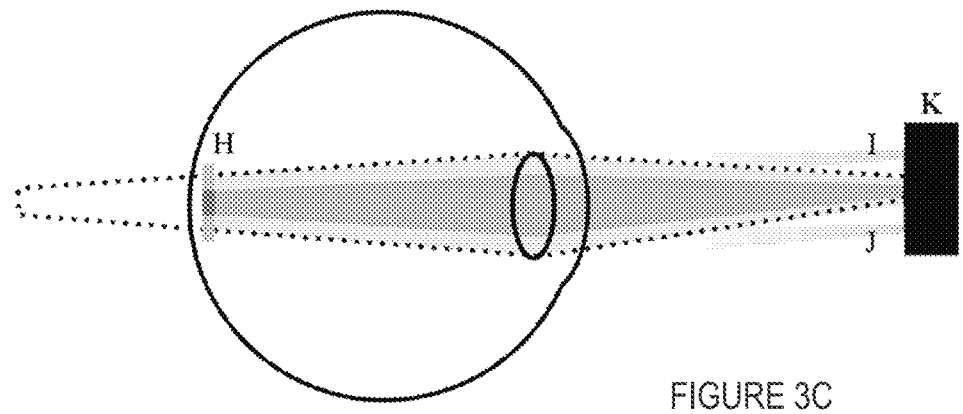

As will be appreciated by the skilled artisan, a light field as seen in FIG. 3C cannot be produced with a 'normal' two-dimensional display because the pixels' light field emits light isotropically. Instead it is necessary to exercise tight control on the angle and origin of the light emitted, for example, using a microlens array or other light field shaping layer such as a parallax barrier, or combination thereof.

Figure 4:
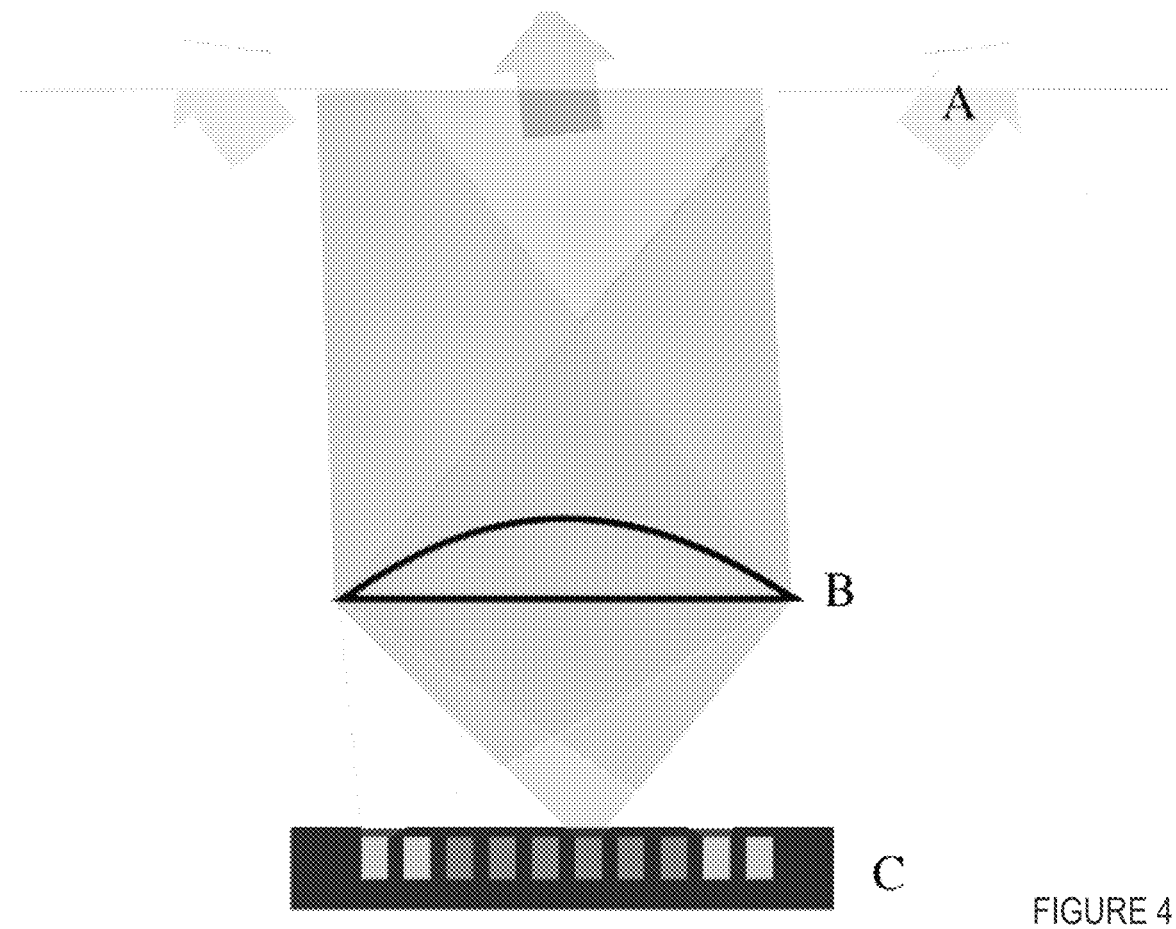
FIG. 4 is a schematic diagram of a single light field pixel defined by a convex lenslet or microlens overlaying an underlying pixel array and disposed at or near its focus to produce a substantially collimated beam, in accordance with one embodiment.

Following with the example of a microlens array, FIG. 4 schematically illustrates a single light field pixel defined by a convex microlens (B) disposed at its focus from a corresponding subset of pixels in an LCD display (C) to produce a substantially collimated beam of light emitted by these pixels, whereby the direction of the beam is controlled by the location of the pixel(s) relative to the microlens. The single light field pixel produces a beam similar to that shown in FIG. 3C where the outside rays are lighter and the majority inside rays are darker. The LCD display (C) emits light which hits the microlens (B) and it results in a beam of substantially collimated light (A).

Figure 5:
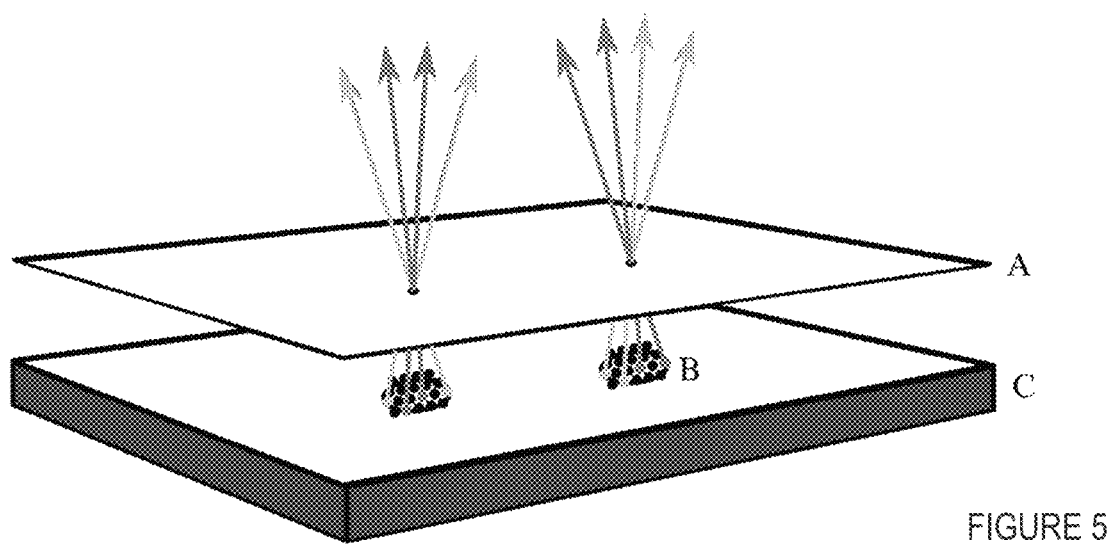
FIG. 5 is another schematic exploded view of an assembly of a light field display in which respective pixel subsets are aligned to emit light through a corresponding microlens or lenslet, in accordance with one embodiment.
Figure 6:
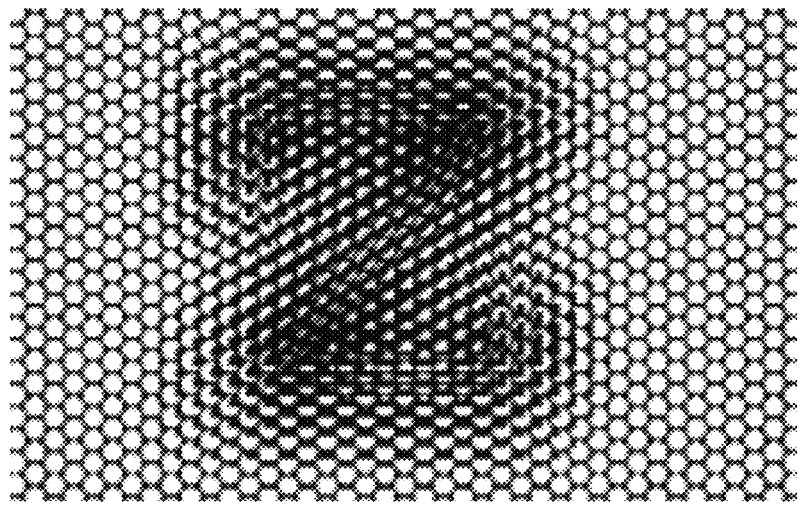
FIG. 6 is an exemplary diagram of a light field pattern that, when properly projected by a light field display, produces a corrected image exhibiting reduced blurring for a viewer having reduced visual acuity, in accordance with one embodiment.

Accordingly, upon predictably aligning a particular microlens array with a pixel array, a designated "circle" of pixels will correspond with each microlens and be responsible for delivering light to the pupil through that lens. FIG. 5 schematically illustrates an example of a light field display assembly in which a microlens array (A) sits above an LCD display on a cellphone (C) to have pixels (B) emit light through the microlens array. A ray-tracing algorithm can thus be used to produce a pattern to be displayed on the pixel array below the microlens in order to create the desired virtual image that will effectively correct for the viewer's reduced visual acuity. FIG. 6 provides an example of such a pattern for the letter "Z". Examples of such ray-tracing algorithms are discussed below.

As will be detailed further below, the separation between the microlens array and the pixel array as well as the pitch of the lenses can be selected as a function of various operating characteristics, such as the normal or average operating distance of the display, and/or normal or average operating ambient light levels.

Further, as producing a light field with angular resolution sufficient for accommodation correction over the full viewing 'zone' of a display would generally require an astronomically high pixel density, instead, a correct light field can be produced, in some embodiments, only at or around the location of the user's pupils. To do so, the light field display can be paired with pupil tracking technology to track a location of the user's eyes/pupils relative to the display. The display can then compensate for the user's eye location and produce the correct virtual image, for example, in real time.

In some embodiments, the light field display can render dynamic images at over 30 frames per second on the hardware in a smartphone.

In some embodiments, the light field display can display a virtual image at optical infinity, meaning that any level of accommodation-based presbyopia (e.g. first order) can be corrected for.

In some further embodiments, the light field display can both push the image back or forward, thus allowing for selective image corrections for both hyperopia (far-sightedness) and myopia (nearsightedness).

In order to demonstrate a working light field solution, and in accordance with one embodiment, the following test was set up. A camera was equipped with a simple lens, to simulate the lens in a human eye and the aperture was set to simulate a normal pupil diameter. The lens was focused to 50 cm away and a phone was mounted 25 cm away. This would approximate a user whose minimal seeing distance is 50 cm and is attempting to use a phone at 25 cm.

Figure 7A:
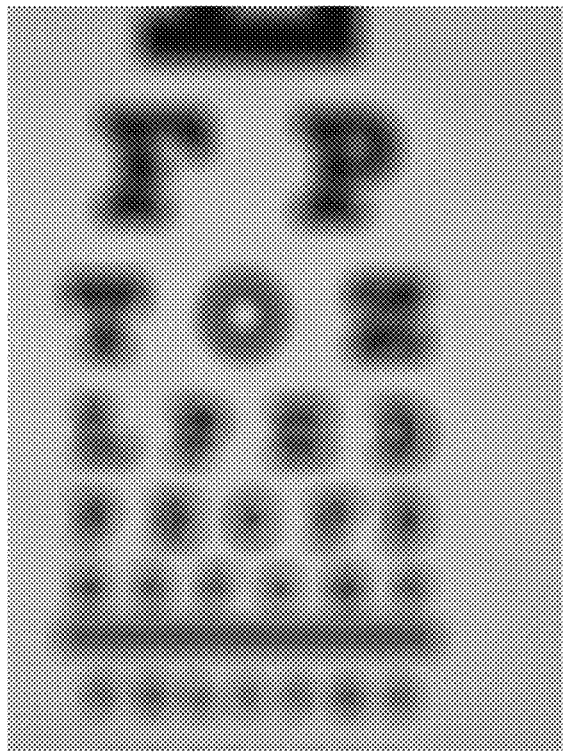
FIGS. 7A and 7B are photographs of a Snellen chart, as illustratively viewed by a viewer with reduced acuity without image correction (blurry image in FIG. 7A) and with image correction via a light field display (corrected image in FIG. 7B), in accordance with one embodiment.
Figure 7B:
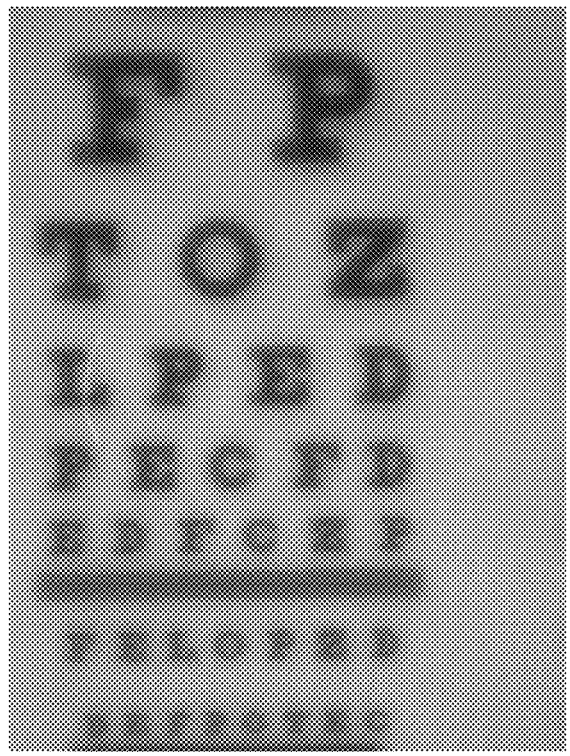

With reading glasses, +2.0 diopters would be necessary for the vision correction. A scaled Snellen chart was displayed on the cellphone and a picture was taken, as shown in FIG. 7A. Using the same cellphone, but with a light field assembly in front that uses that cellphone's pixel array, a virtual image compensating for the lens focus is displayed. A picture was again taken, as shown in FIG. 7B, showing a clear improvement.

Figure 9B:
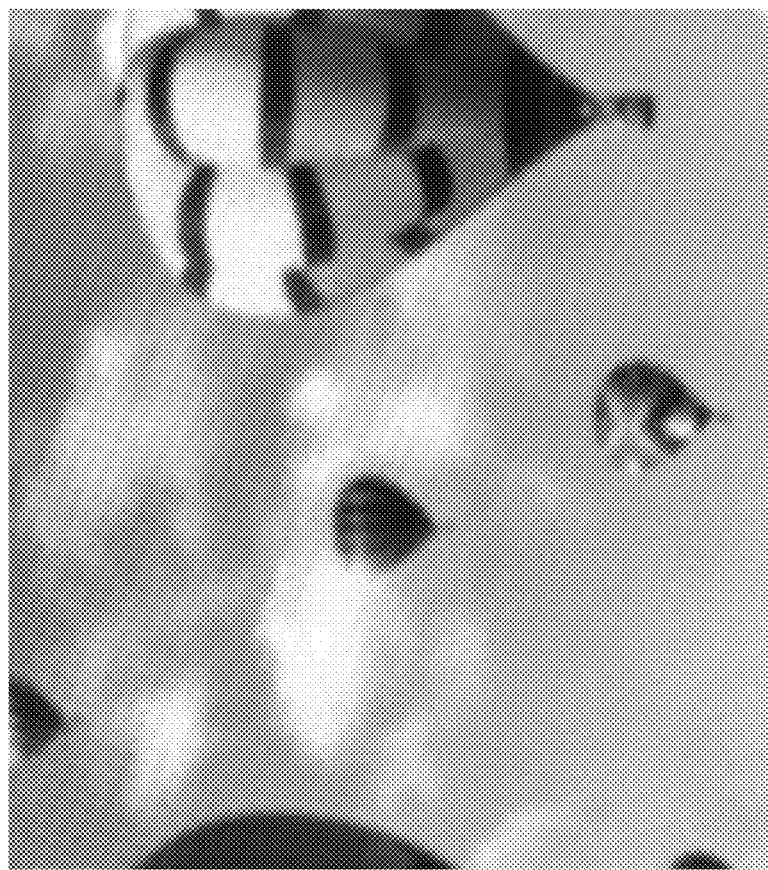
FIGS. 9A and 9B are photographs as illustratively viewed by a viewer with reduced visual acuity without image correction (blurry image in FIG. 9A) and with image correction via a light field display having an angularly mismatched lenslet array (corrected image in FIG. 9B), in accordance with one embodiment.
Figure 9A:
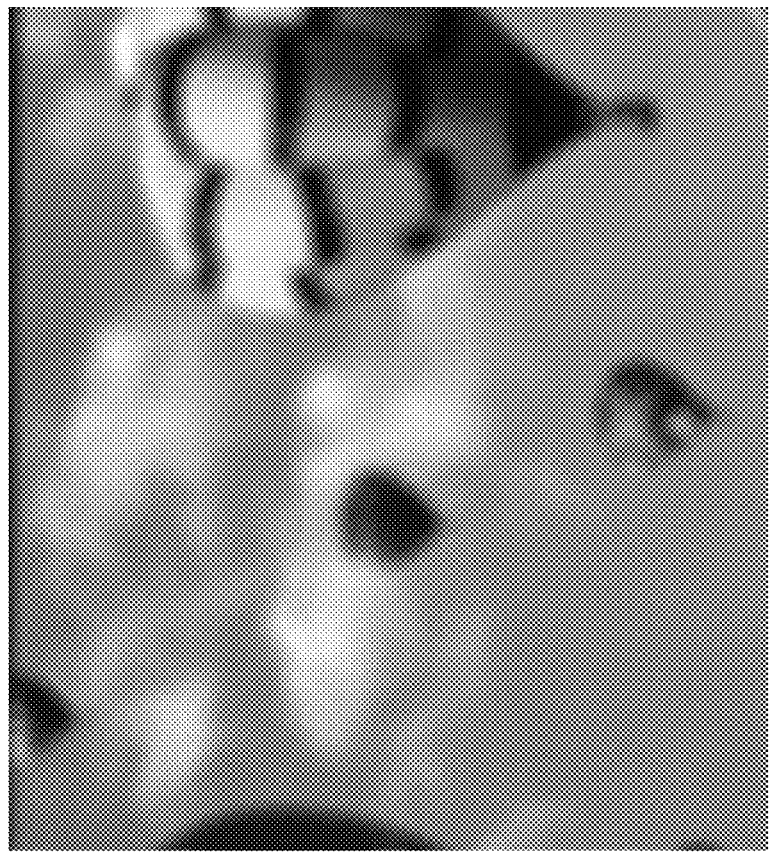

FIGS. 9A and 9B provide another example of results achieved using an exemplary embodiment, in which a colour image was displayed on the LCD display of a Sony™ Xperia™ XZ Premium phone (reported screen resolution of 3840×2160 pixels with 16:9 ratio and approximately 807 pixel-per-inch (ppi) density) without image correction (FIG. 9A) and with image correction through a square fused silica microlens array set at a 2 degree angle relative to the screen's square pixel array and defined by microlenses having a 7.0 mm focus and 200 µm pitch. In this example, the camera lens was again focused at 50 cm with the phone positioned 30 cm away. Another microlens array was used to produce similar results, and consisted of microlenses having a 10.0 mm focus and 150 µm pitch.

Figure 10A:
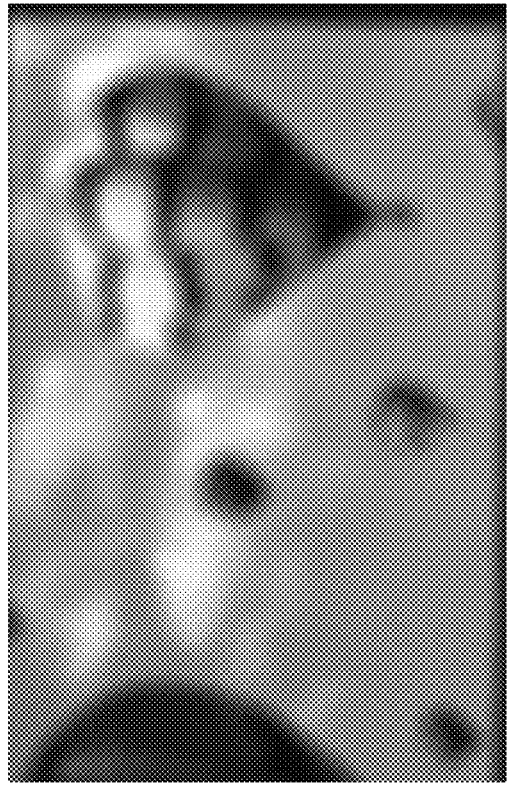
FIGS. 10A and 10B are photographs as illustratively viewed by a viewer with reduced visual acuity without image correction (blurry image in FIG. 10A) and with image correction via a light field display having an angularly mismatched lenslet array (corrected image in FIG. 10B), in accordance with one embodiment.
Figure 10B:
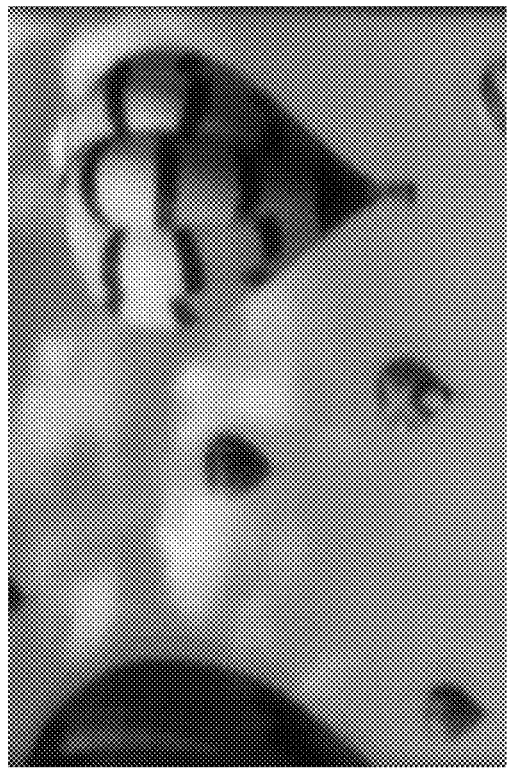

FIGS. 10A and 10B provide yet another example or results achieved using an exemplary embodiment, in which a colour image was displayed on the LCD display of the Sony™ Xperia™ XZ Premium phone without image correction (FIG. 10A) and with image correction through a square fused silica microlens array set at a 2 degree angle relative to the screen's square pixel array and defined by microlenses having a 10.0 mm focus and 150 µm pitch. In this example, the camera lens was focused at 66 cm with the phone positioned 40 cm away.

Accordingly, a display device as described above and further exemplified below, can be configured to render a corrected image via the light field shaping layer that accommodates for the user's visual acuity. By adjusting the image correction in accordance with the user's actual predefined, set or selected visual acuity level, different users and visual acuity may be accommodated using a same device configuration. That is, in one example, by adjusting corrective image pixel data to dynamically adjust a virtual image distance below/above the display as rendered via the light field shaping layer, different visual acuity levels may be accommodated.

As will be appreciated by the skilled artisan, different image processing techniques may be considered, such as those introduced above and taught by Pamplona and/or Huang, for example, which may also influence other light field parameters to achieve appropriate image correction, virtual image resolution, brightness and the like.

Figure 8:
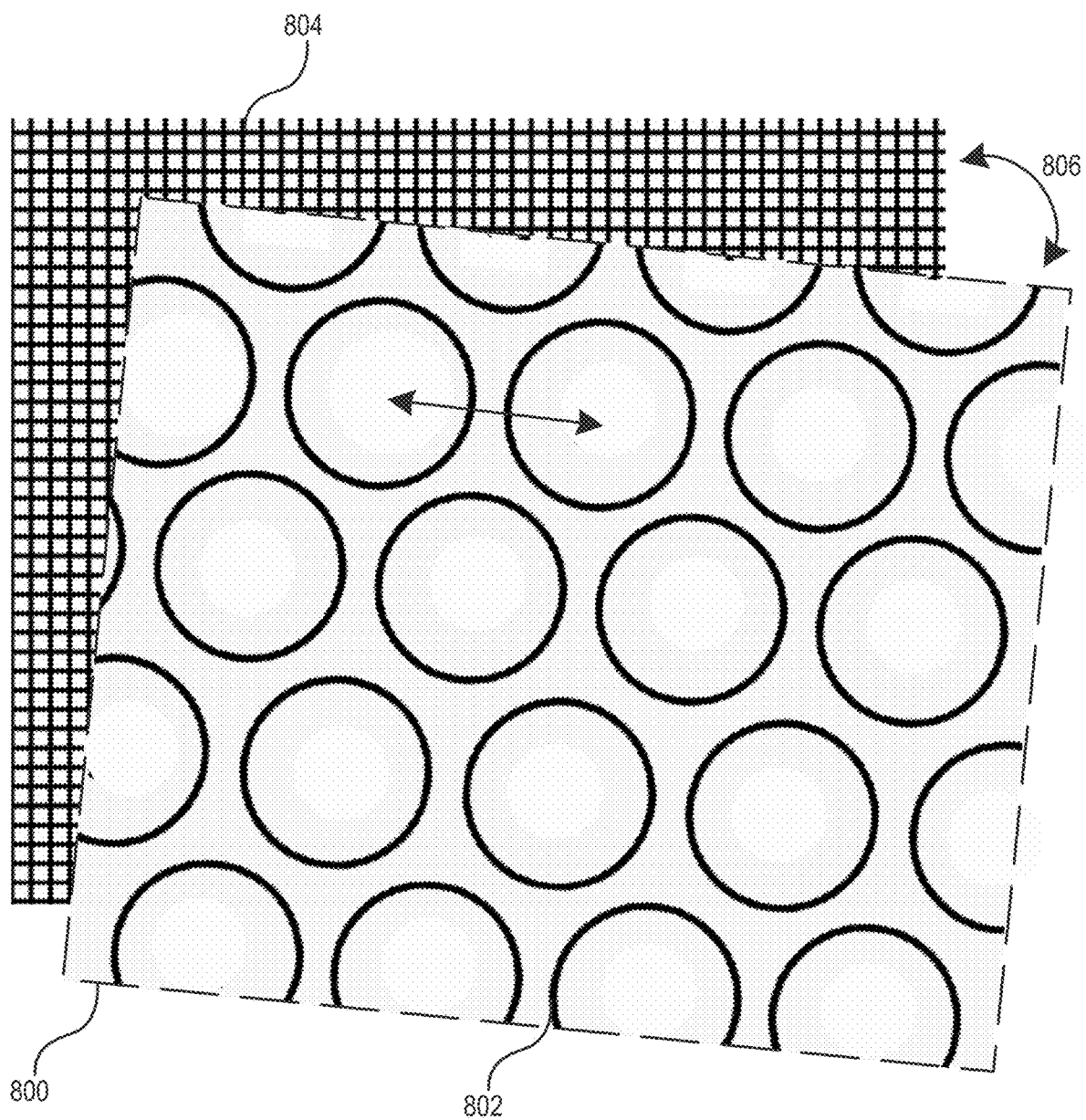
FIG. 8 is a schematic diagram of a portion of a hexagonal lenslet array disposed at an angle relative to an underlying pixel array, in accordance with one embodiment.

With reference to FIG. 8, and in accordance with one embodiment, a microlens array configuration will now be described, in accordance with another embodiment, to provide light field shaping elements in a corrective light field implementation. In this embodiment, the microlens array 800 is defined by a hexagonal array of microlenses 802 disposed so to overlay a corresponding square pixel array 804. In doing so, while each microlens 802 can be aligned with a designated subset of pixels to produce light field pixels as described above, the hexagonal-to-square array mismatch can alleviate certain periodic optical artifacts that may otherwise be manifested given the periodic nature of the optical elements and principles being relied upon to produce the desired optical image corrections. Conversely, a square microlens array may be favoured when operating a digital display comprising a hexagonal pixel array.

In some embodiments, as illustrated in FIG. 8, the microlens array 800 may further or alternatively overlaid at an angle 806 relative to the underlying pixel array, which can further or alternatively alleviate period optical artifacts.

In yet some further or alternative embodiments, a pitch ratio between the microlens array and pixel array may be deliberately selected to further or alternatively alleviate periodic optical artifacts. For example, a perfectly matched pitch ratio (i.e. an exact integer number of display pixels per microlens) is most likely to induce periodic optical artifacts, whereas a pitch ratio mismatch can help reduce such occurrences. Accordingly, in some embodiments, the pitch ratio will be selected to define an irrational number, or at least, an irregular ratio, so to minimize periodic optical artifacts. For instance, a structural periodicity can be defined so to reduce the number of periodic occurrences within the dimensions of the display screen at hand, e.g. ideally selected so to define a structural period that is greater than the size of the display screen being used.

While this example is provided within the context of a microlens array, similar structural design considerations may be applied within the context of a parallax barrier, diffractive barrier or combination thereof.

Figure 11:
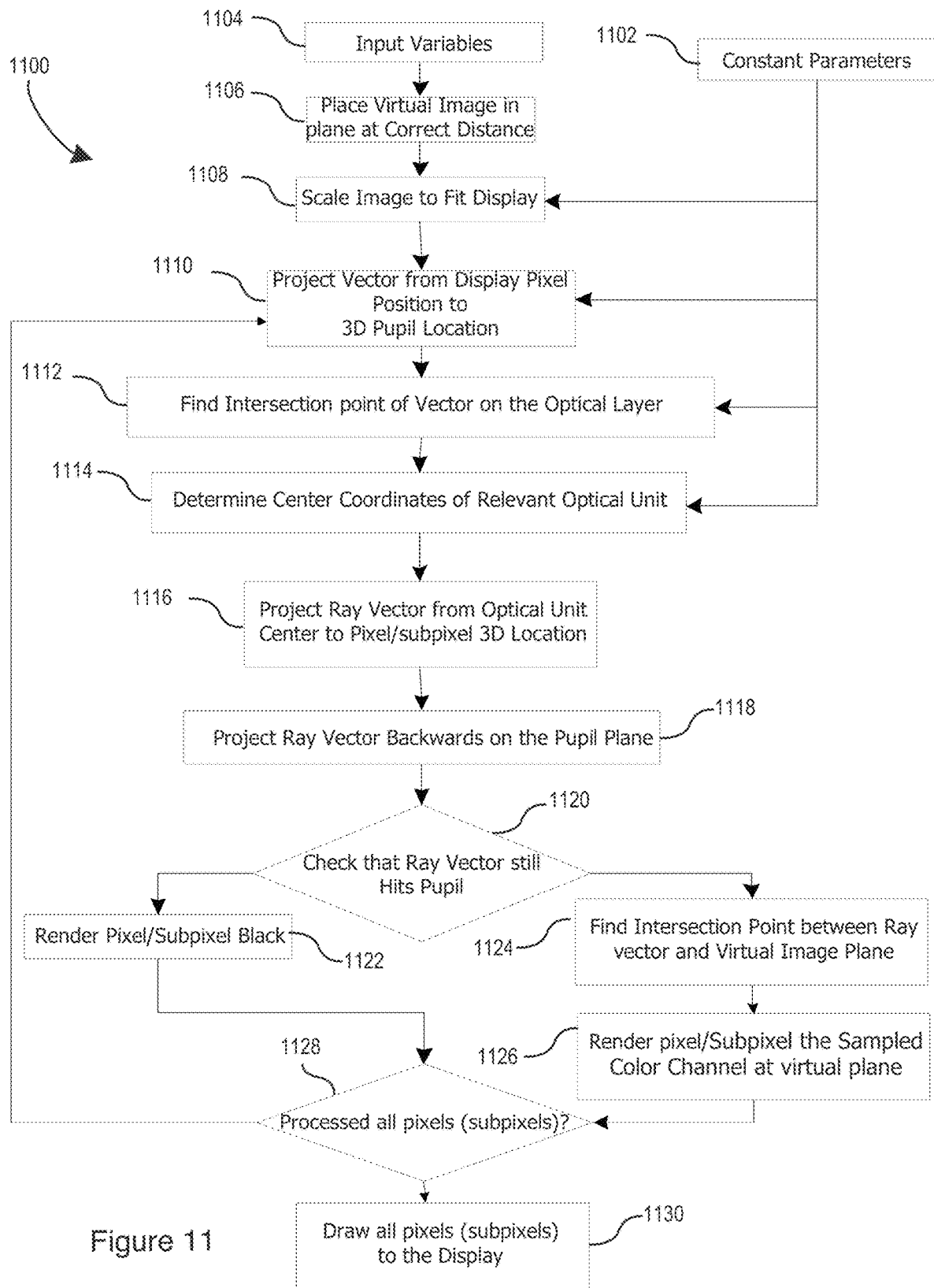
FIG. 11 is a process flow diagram of an illustrative ray-tracing rendering process, in accordance with one embodiment.
Figure 12:
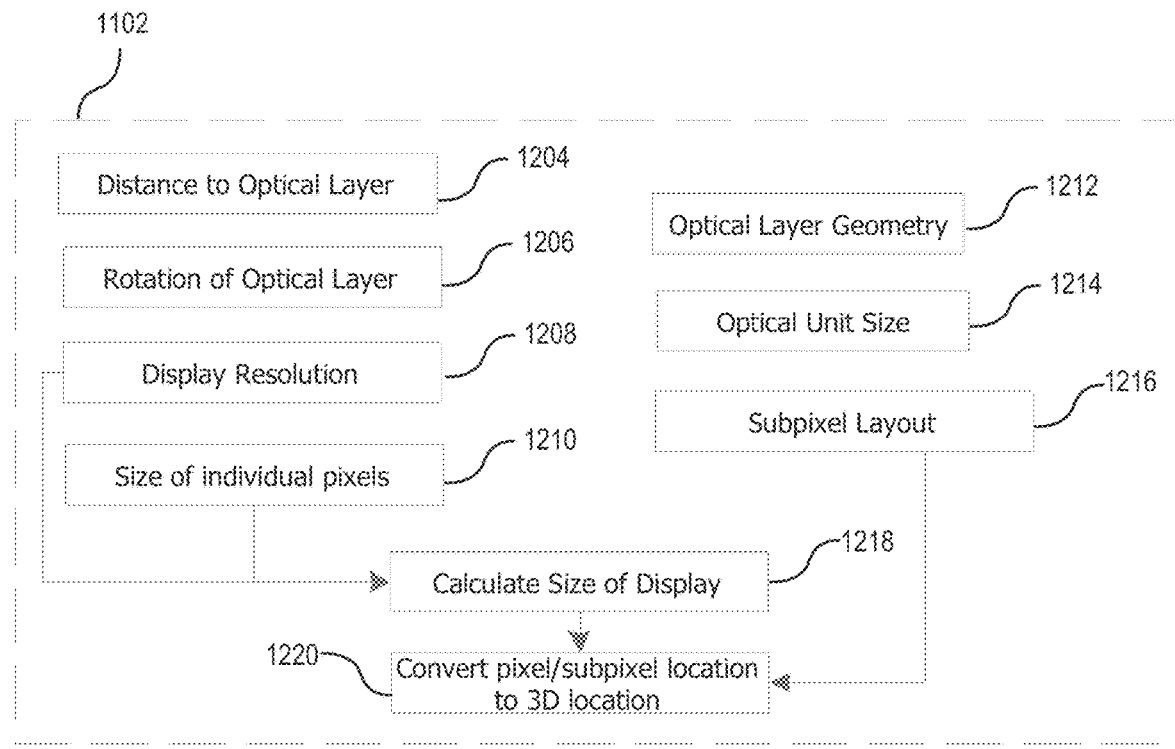
FIGS. 12 and 13 are process flow diagrams of exemplary input constant parameters and variables, respectively, for the ray-tracing rendering process of FIG. 11, in accordance with one embodiment.
Figure 13:
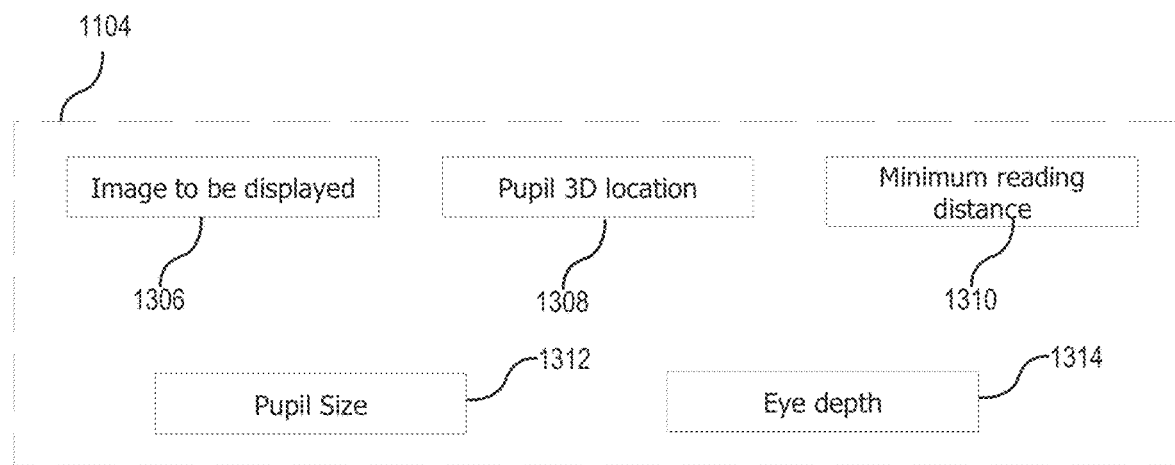

With reference to FIGS. 11 to 13, and in accordance with one embodiment, an exemplary computationally implemented ray-tracing method for rendering an adjusted image via an array of light field shaping elements, in this example provided by a light field shaping layer (LFSL) disposed relative to a set of underlying display pixels, that accommodates for the user's reduced visual acuity will now be described. In this example, for illustrative purposes, adjustment of a single image (i.e. the image as whole) is being implemented without consideration for distinct image portions. Further examples below will specifically address modification of the following example for adaptively adjusting distinct image portions.

In this exemplary embodiment, a set of constant parameters 1102 may be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user's viewing session.

As illustrated in FIG. 12, the list of constant parameters 1102 may include, without limitations, the distance 1204 between the display and the LFSL, the in-plane rotation angle 1206 between the display and LFSL frames of reference, the display resolution 1208, the size of each individual pixel 1210, the optical LFSL geometry 1212, the size of each optical element 1214 within the LFSL and optionally the subpixel layout 1216 of the display. Moreover, both the display resolution 1208 and the size of each individual pixel 1210 may be used to pre-determine both the absolute size of the display in real units (i.e. in mm) and the three-dimensional position of each pixel within the display. In some embodiments where the subpixel layout 1216 is available, the position within the display of each subpixel may also be pre-determined. These three-dimensional location/positions are usually calculated using a given frame of reference located somewhere within the plane of the display, for example a corner or the middle of the display, although other reference points may be chosen. Concerning the optical layer geometry 1212, different geometries may be considered, for example a hexagonal geometry such as the one shown in FIG. 8. Finally, by combining the distance 1204, the rotation angle 1206, and the geometry 1212 with the optical element size 1214, it is possible to similarly pre-determine the three-dimensional location/position of each optical element center with respect to the display's same frame of reference.

FIG. 13 meanwhile illustratively lists an exemplary set of input variables 1104 for method 1100, which may include any input data fed into method 1100 that may reasonably change during a user's single viewing session, and may thus include without limitation: the image(s) to be displayed 1306 (e.g. pixel data such as on/off, colour, brightness, etc.), the three-dimensional pupil location 1308 (e.g. in embodiments implementing active eye/pupil tracking methods) and/or pupil size 1312 and the minimum reading distance 1310 (e.g. one or more parameters representative of the user's reduced visual acuity or condition). In some embodiments, the eye depth 1314 may also be used. The image data 1306, for example, may be representative of one or more digital images to be displayed with the digital pixel display. This image may generally be encoded in any data format used to store digital images known in the art. In some embodiments, images 1306 to be displayed may change at a given framerate.

The pupil location 1308, in one embodiment, is the three-dimensional coordinates of at least one the user's pupils' center with respect to a given reference frame, for example a point on the device or display. This pupil location 1308 may be derived from any eye/pupil tracking method known in the art. In some embodiments, the pupil location 1308 may be determined prior to any new iteration of the rendering algorithm, or in other cases, at a lower framerate. In some embodiments, only the pupil location of a single user's eye may be determined, for example the user's dominant eye (i.e. the one that is primarily relied upon by the user). In some embodiments, this position, and particularly the pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1310 is defined as the minimal focus distance for reading that the user's eye(s) may be able to accommodate (i.e. able to view without discomfort). In some embodiments, different values of the minimum reading distance 1310 associated with different users may be entered, for example, as can other adaptive vision correction parameters be considered depending on the application at hand and vision correction being addressed. In some embodiments, minimum reading distance 1310 may be derived from an eye prescription (e.g. glasses prescription or contact prescription) or similar. It may, for example, correspond to the near point distance corresponding to the uncorrected user's eye, which can be calculated from the prescribed corrective lens power assuming that the targeted near point was at 25 cm.

Figure 14A:
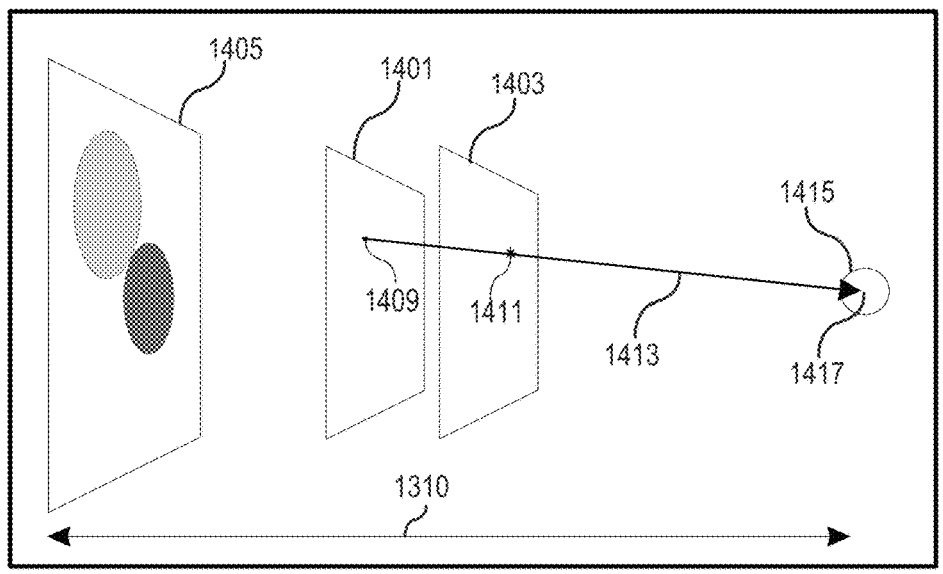
FIGS. 14A to 14C are schematic diagrams illustrating certain process steps of FIG. 11.
Figure 14B:
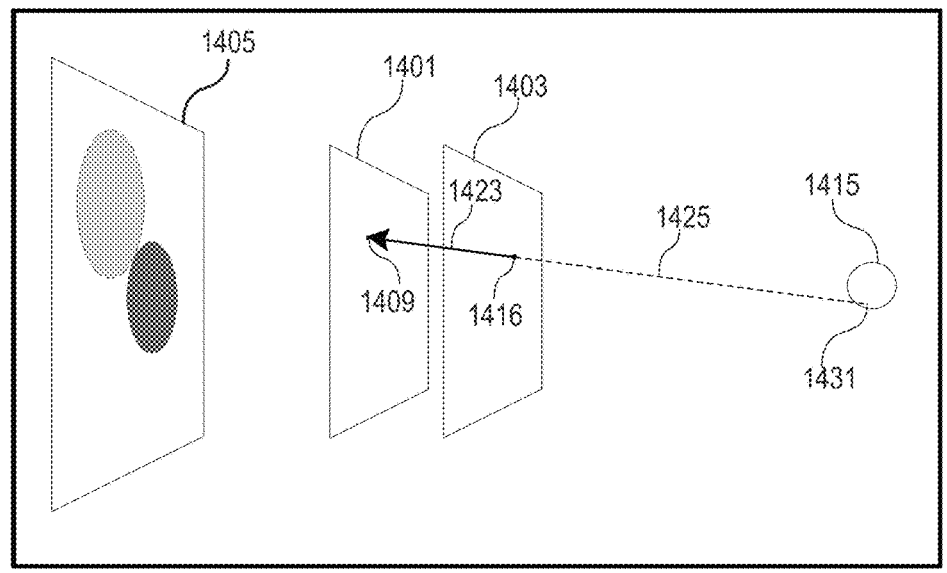
Figure 14C:
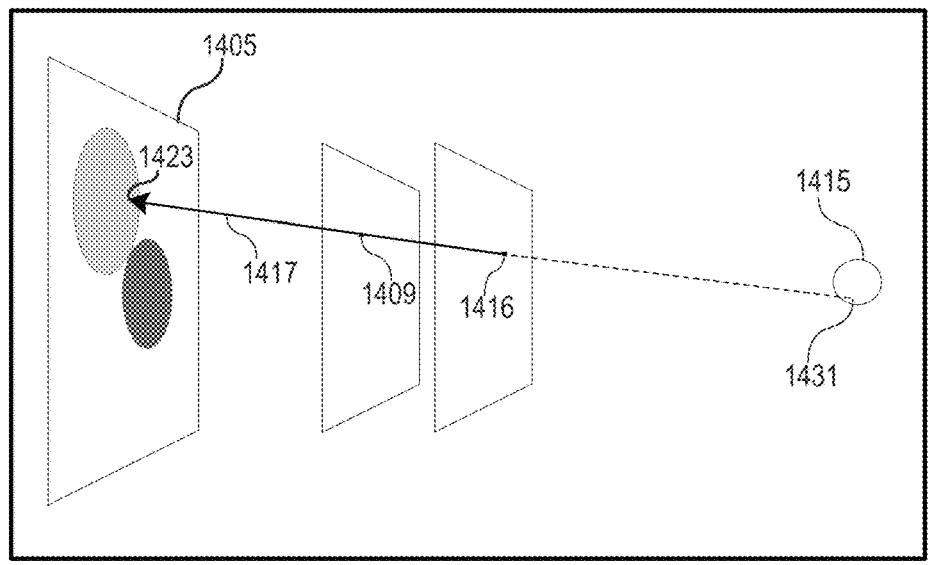

With added reference to FIGS. 14A to 14C, once parameters 1102 and variables 1104 have been set, the method of FIG. 11 then proceeds with step 1106, in which the minimum reading distance 1310 (and/or related parameters) is used to compute the position of a virtual (adjusted) image plane 1405 with respect to the device's display, followed by step 1108 wherein the size of image 1306 is scaled within the image plane 1405 to ensure that it correctly fills the pixel display 1401 when viewed by the distant user. This is illustrated in FIG. 14A, which shows a diagram of the relative positioning of the user's pupil 1415, the light field shaping layer 1403, the pixel display 1401 and the virtual image plane 1405. In this example, the size of image 1306 in image plane 1405 is increased to avoid having the image as perceived by the user appear smaller than the display's size.

An exemplary ray-tracing methodology is described in steps 1110 to 1128 of FIG. 11, at the end of which the output color of each pixel of pixel display 1401 is known so as to virtually reproduce the light field emanating from an image 1306 positioned at the virtual image plane 1405. In FIG. 11, these steps are illustrated in a loop over each pixel in pixel display 1401, so that each of steps 1110 to 1126 describes the computations done for each individual pixel. However, in some embodiments, these computations need not be executed sequentially, but rather, steps 1110 to 1128 may executed in parallel for each pixel or a subset of pixels at the same time. Indeed, as will be discussed below, this exemplary method is well suited to vectorization and implementation on highly parallel processing architectures such as GPUs.

As illustrated in FIG. 14A, in step 1110, for a given pixel 1409 in pixel display 1401, a trial vector 1413 is first generated from the pixel's position to the center position 1417 of pupil 1415. This is followed in step 1112 by calculating the intersection point 1411 of vector 1413 with the LF SL 1403.

The method then finds, in step 1114, the coordinates of the center 1416 of the LFSL optical element closest to intersection point 1411. This step may be computationally intensive and will be discussed in more depth below. Once the position of the center 1416 of the optical element is known, in step 1116, a normalized unit ray vector is generated from drawing and normalizing a vector 1423 drawn from center position 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. The direction of this ray vector will be used to find the portion of image 1306, and thus the associated color, represented by pixel 1409. But first, in step 1118, this ray vector is projected backwards to the plane of pupil 1415, and then in step 1120, the method verifies that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

If this deviation is deemed to be too large (i.e. light emanating from pixel 1409 channeled through optical element 1416 is not perceived by pupil 1415), then in step 1122, the method flags pixel 1409 as unnecessary and to simply be turned off or render a black color. Otherwise, as shown in FIG. 14C, in step 1124, the ray vector is projected once more towards virtual image plane 1405 to find the position of the intersection point 1423 on image 1306. Then in step 1126, pixel 1409 is flagged as having the color value associated with the portion of image 1306 at intersection point 1423.

In some embodiments, method 1100 is modified so that at step 1120, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1220 continues to step 1124. At step 1126, the pixel color value assigned to pixel 1409 is chosen to be somewhere between the full color value of the portion of image 1306 at intersection point 1423 or black, depending on the value of the interpolation function used at step 1120 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In some embodiments, steps 1118, 1120 and 1122 may be avoided completely, the method instead going directly from step 1116 to step 1124. In such an exemplary embodiment, no check is made that the ray vector hits the pupil or not, but instead the method assumes that it always does.

Once the output colors of all pixels have been determined, these are finally rendered in step 1130 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

With reference to FIGS. 19 and 20A to 20D, and in accordance with one embodiment, another exemplary computationally implemented ray-tracing method for rendering an adjusted image via the light field shaping layer (LFSL) that accommodates for the user's reduced visual acuity, for example, will now be described. Again, for illustrative purposes, in this example, adjustment of a single image (i.e. the image as whole) is being implemented without consideration for distinct image portions. Further examples below will specifically address modification of the following example for adaptively adjusting distinct image portions.

In this embodiment, the adjusted image portion associated with a given pixel/subpixel is computed (mapped) on the retina plane instead of the virtual image plane considered in the above example, again in order to provide the user with a designated image perception adjustment. Therefore, the currently discussed exemplary embodiment shares some steps with the method of FIG. 11. Indeed, a set of constant parameters 1102 may also be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user viewing session. The list of possible variables and constants is substantially the same as the one disclosed in FIGS. 12 and 13 and will thus not be replicated here.

Once parameters 1102 and variables 1104 have been set, this second exemplary ray-tracing methodology proceeds from steps 1910 to 1936, at the end of which the output color of each pixel of the pixel display is known so as to virtually reproduce the light field emanating from an image perceived to be positioned at the correct or adjusted image distance, in one example, so to allow the user to properly focus on this adjusted image (i.e. having a focused image projected on the user's retina) despite a quantified visual aberration. In FIG. 19, these steps are illustrated in a loop over each pixel in pixel display 1401, so that each of steps 1910 to 1934 describes the computations done for each individual pixel. However, in some embodiments, these computations need not be executed sequentially, but rather, steps 1910 to 1934 may be executed in parallel for each pixel or a subset of pixels at the same time. Indeed, as will be discussed below, this second exemplary method is also well suited to vectorization and implementation on highly parallel processing architectures such as GPUs.

Referencing once more FIG. 14A, in step 1910 (as in step 1110), for a given pixel in pixel display 1401, a trial vector 1413 is first generated from the pixel's position to pupil center 1417 of the user's pupil 1415. This is followed in step 1912 by calculating the intersection point of vector 1413 with optical layer 1403.

From there, in step 1914, the coordinates of the optical element center 1416 closest to intersection point 1411 are determined. This step may be computationally intensive and will be discussed in more depth below. As shown in FIG. 14B, once the position of the optical element center 1416 is known, in step 1916, a normalized unit ray vector is generated from drawing and normalizing a vector 1423 drawn from optical element center 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. In step 1918, this ray vector is projected backwards to pupil 1415, and then in step 1920, the method ensures that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

Now referring to FIGS. 20A to 20D, steps 1921 to 1929 of method 1900 will be described. Once optical element center 1416 of the relevant optical unit has been determined, at step 1921, a vector 2004 is drawn from optical element center 1416 to pupil center 1417. Then, in step 1923, vector 2004 is projected further behind the pupil plane onto eye focal plane 2006 (location where any light rays originating from optical layer 1403 would be focused by the eye) to locate focal point 2008. For a user with perfect vision, focal plane 2006 would be located at the same location as retina plane 2010, but in this example, focal plane 2006 is located behind retina plane 2010, which would be expected for a user with some form of farsightedness. The position of focal plane 2006 may be derived from the user's minimum reading distance 1310, for example, by deriving therefrom the focal length of the user's eye. Other manually input or computationally or dynamically adjustable means may also or alternatively be considered to quantify this parameter.

The skilled artisan will note that any light ray originating from optical element center 1416, no matter its orientation, will also be focused onto focal point 2008, to a first approximation. Therefore, the location 2012 on retina plane 2010 onto which light entering the pupil at intersection point 1431 will converge may be approximated by drawing a straight line between intersection point 1431 where ray vector 1425 hits the pupil 1415 and focal point 2008 on focal plane 2006. The intersection of this line with retina plane 2010 (retina image point 2012) is thus the location on the user's retina corresponding to the image portion that will be reproduced by corresponding pixel 1409 as perceived by the user. Therefore, by comparing the relative position of retina point 2012 with the overall position of the projected image on the retina plane 2010, the relevant adjusted image portion associated with pixel 1409 may be computed.

To do so, at step 1927, the corresponding projected image center position on retina plane 2010 is calculated. Vector 2016 is generated originating from the center position of display 1401 (display center position 2018) and passing through pupil center 1417. Vector 2016 is projected beyond the pupil plane onto retina plane 2010, wherein the associated intersection point gives the location of the corresponding retina image center 2020 on retina plane 2010. The skilled technician will understand that step 1927 could be performed at any moment prior to step 1929, once the relative pupil center location 1417 is known in input variables step 1904. Once image center 2020 is known, one can then find the corresponding image portion of the selected pixel/subpixel at step 1929 by calculating the x/y coordinates of retina image point 2012 relative to retina image center 2020 on the retina, scaled to the x/y retina image size 2031.

Figure 20A:
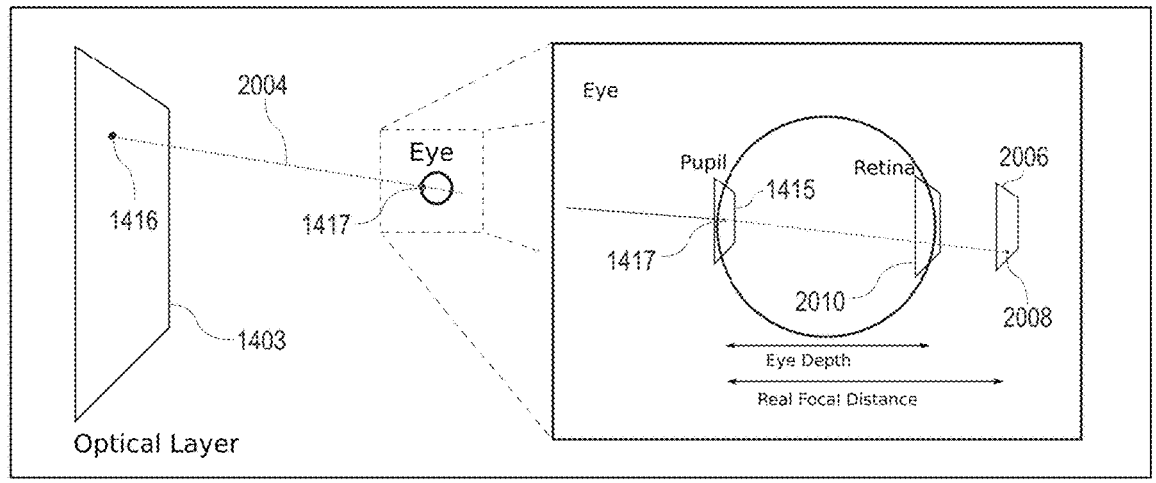
FIGS. 20A to 20D are schematic diagrams illustrating certain process steps of FIG. 19.
Figure 20B:
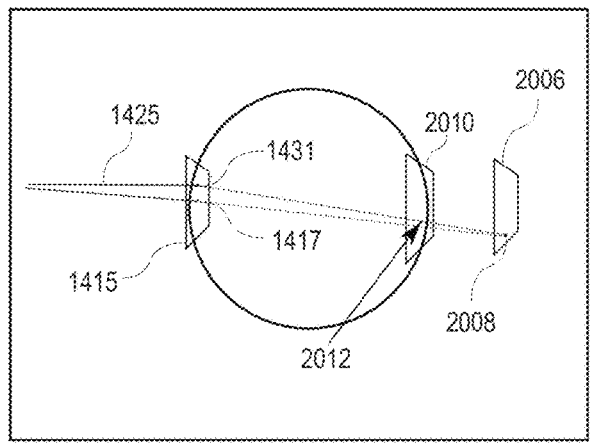
Figure 20C:
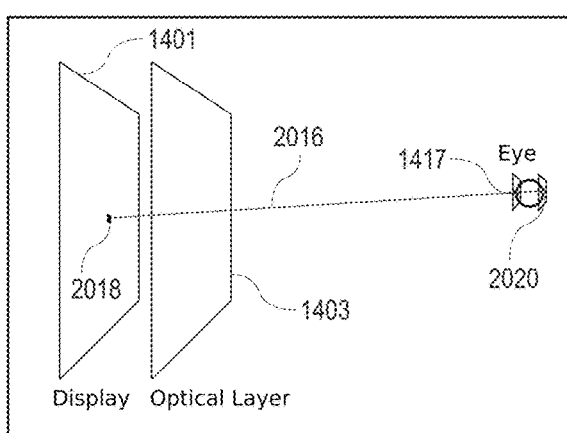
Figure 20D:
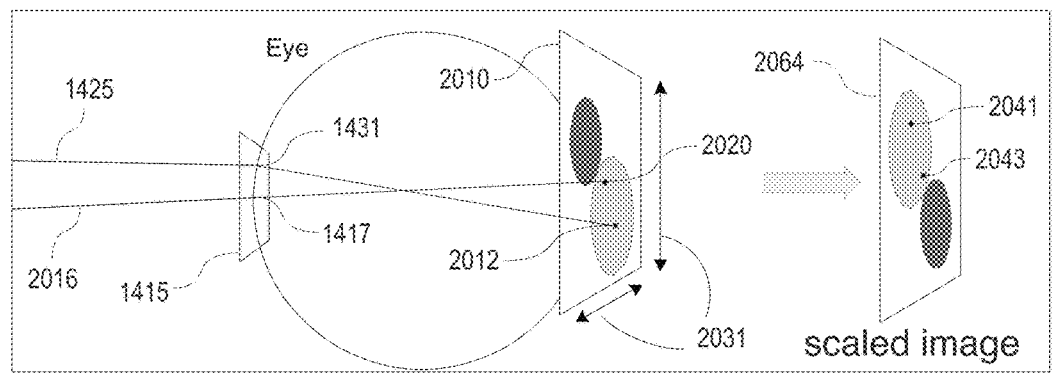

This retina image size 2031 may be computed by calculating the magnification of an individual pixel on retina plane 2010, for example, which may be approximately equal to the x or y dimension of an individual pixel multiplied by the eye depth 1314 and divided by the absolute value of the distance to the eye (i.e. the magnification of pixel image size from the eye lens). Similarly, for comparison purposes, the input image is also scaled by the image x/y dimensions to produce a corresponding scaled input image 2064. Both the scaled input image and scaled retina image should have a width and height between −0.5 to 0.5 units, enabling a direct comparison between a point on the scaled retina image 2010 and the corresponding scaled input image 2064, as shown in FIG. 20D.

From there, the image portion position 2041 relative to retina image center position 2043 in the scaled coordinates (scaled input image 2064) corresponds to the inverse (because the image on the retina is inverted) scaled coordinates of retina image point 2012 with respect to retina image center 2020. The associated color with image portion position 2041 is therefrom extracted and associated with pixel 1409.

In some embodiments, method 1900 may be modified so that at step 1920, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1920 continues to step 1124. At step 1931, the pixel color value assigned to pixel 1409 is chosen to be somewhere between the full color value of the portion of image 1306 at intersection point 1423 or black, depending on the value of the interpolation function used at step 1920 (1 or 0).

In yet other embodiments, pixels found to illuminate a designated area around the pupil may still be rendered, for example, to produce a buffer zone to accommodate small movements in pupil location, for example, or again, to address potential inaccuracies or misalignments.

Once the output colors of all pixels in the display have been determined (check at step 1934 is true), these are finally rendered in step 1936 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process of FIG. 19 can accommodate the formation of a virtual image effectively set at infinity without invoking such computational challenges. Likewise, while first order aberrations are illustratively described with reference to FIG. 19, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1110 to 1128 of FIG. 11 or steps 1920 to 1934 of FIG. 19) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

With reference to FIGS. 15 to 18C and in accordance with one exemplary embodiment, an exemplary process for computing the center position of an associated light field shaping element in the ray-tracing process of FIG. 11 (or FIG. 19) will now be described. The series of steps are specifically tailored to avoid code branching, so as to be increasingly efficient when run on GPUs (i.e. to avoid so called "warp divergence"). Indeed, with GPUs, because all the processors must execute identical instructions, divergent branching can result in reduced performance.

Figure 15:
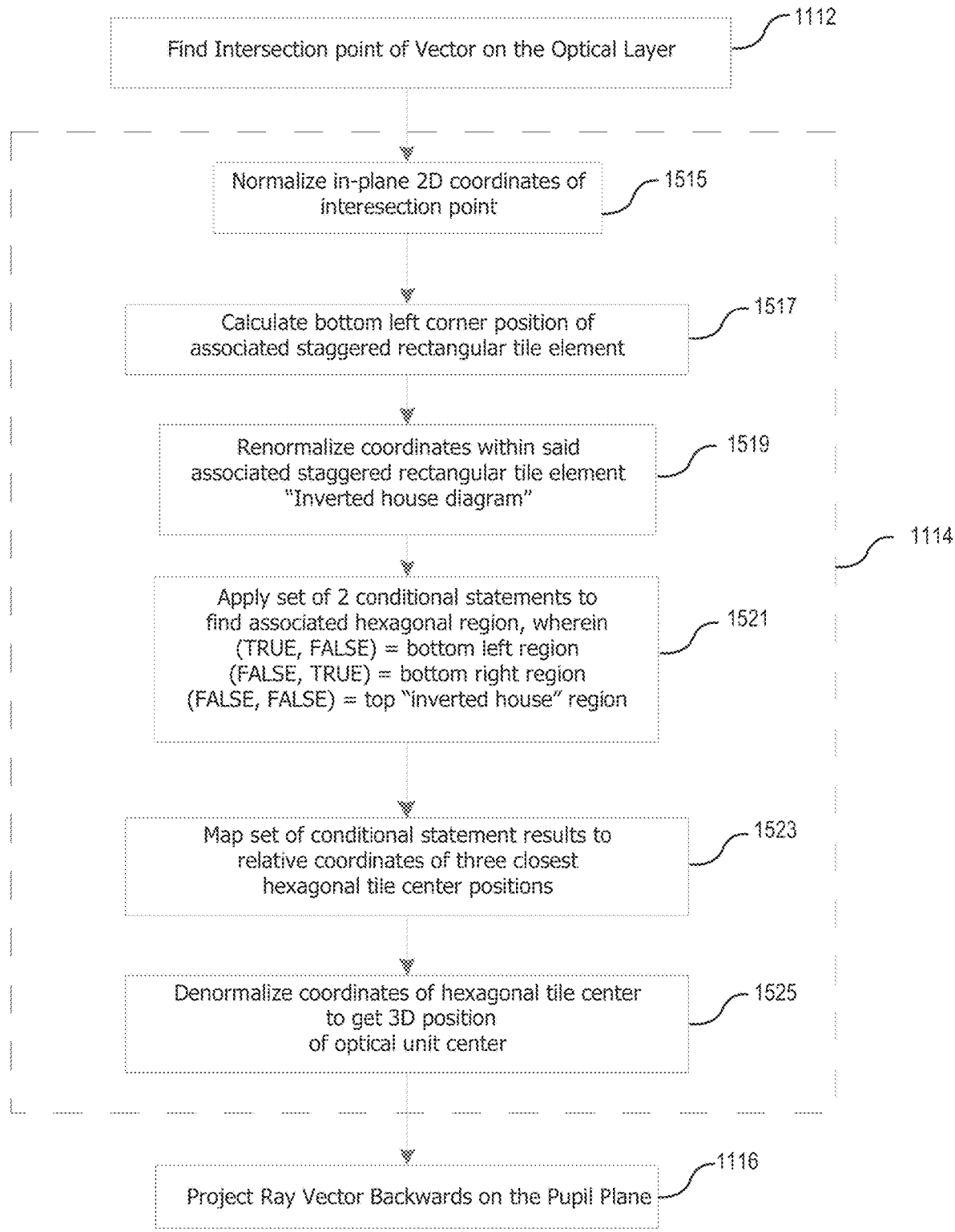
FIG. 15 is a process flow diagram of an exemplary process for computing the center position of an associated light field shaping unit in the ray-tracing rendering process of FIG. 11, in accordance with one embodiment.

With reference to FIG. 15, and in accordance with one embodiment, step 1114 of FIG. 11 is expanded to include steps 1515 to 1525. A similar discussion can readily be made in respect of step 1914 of FIG. 19, and thus need not be explicitly detailed herein. The method receives from step 1112 the 2D coordinates of the intersection point 1411 (illustrated in FIG. 14A) of the trial vector 1413 with optical layer 1403. As discussed with respect to the exemplary embodiment of FIG. 8, there may be a difference in orientation between the frames of reference of the optical layer (hexagonal array of microlenses 802 in FIG. 8, for example) and of the corresponding pixel display (square pixel array 804 in FIG. 8, for example). This is why, in step 1515, these input intersection coordinates, which are initially calculated from the display's frame of reference, may first be rotated to be expressed from the light field shaping layer's frame of reference and optionally normalized so that each individual light shaping element has a width and height of 1 unit. The following description will be equally applicable to any light field shaping layer having a hexagonal geometry like the exemplary embodiment of FIG. 8. Note however that the method steps 1515 to 1525 described herein may be equally applied to any kind of light field shaping layer sharing the same geometry (i.e. not only a microlens array, but pinhole arrays as well, etc.). Likewise, while the following example is specific to an exemplary hexagonal array of LFSL elements definable by a hexagonal tile array of regular hexagonal tiles, other geometries may also benefit from some or all of the features and/or advantages of the herein-described and illustrated embodiments. For example, different hexagonal LFSL element arrays, such as stretched/elongated, skewed and/or rotated arrays may be considered, as can other nestled array geometries in which adjacent rows and/or columns of the LFSL array at least partially "overlap" or inter-nest. For instance, as will be described further below, hexagonal arrays and like nestled array geometries will generally provide for a commensurately sized rectangular/square tile of an overlaid rectangular/square array or grid to naturally encompass distinct regions as defined by two or more adjacent underlying nestled array tiles, which can be used to advantage in the examples provided below. In yet other embodiments, the processes discussed herein may be applied to rectangular and/or square LFSL element arrays. Other LFSL element array geometries may also be considered, as will be appreciated by the skilled artisan upon reading of the following example, without departing from the general scope and nature of the present disclosure.

Figure 16A:
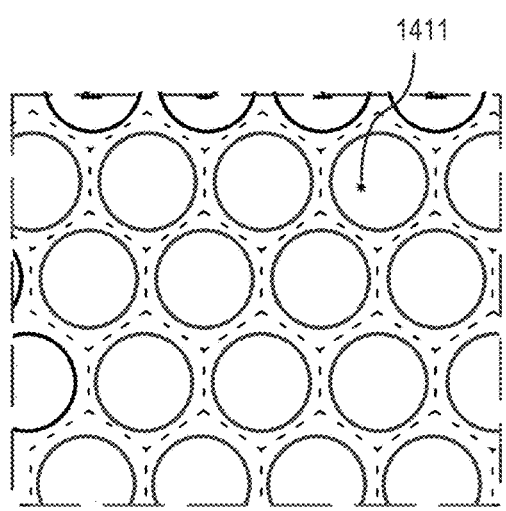
FIGS. 16A and 16B are schematic diagrams illustrating an exemplary hexagonal light field shaping layer with a corresponding hexagonal tile array, in accordance with one embodiment.
Figure 16B:
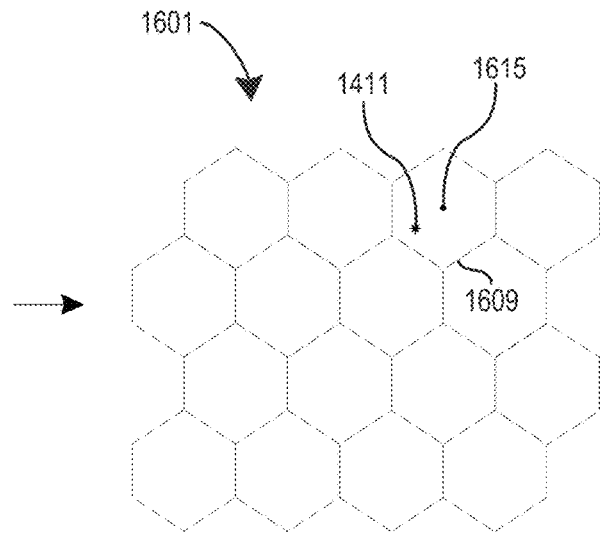

For hexagonal geometries, as illustrated in FIGS. 16A and 16B, the hexagonal symmetry of the light field shaping layer 1403 may be represented by drawing an array of hexagonal tiles 1601, each centered on their respective light field shaping element, so that the center of a hexagonal tile element is more or less exactly the same as the center position of its associated light field shaping element. Thus, the original problem is translated to a slightly similar one whereby one now needs to find the center position 1615 of the associated hexagonal tile 1609 closest to the intersection point 1411, as shown in FIG. 16B.

Figure 17A:
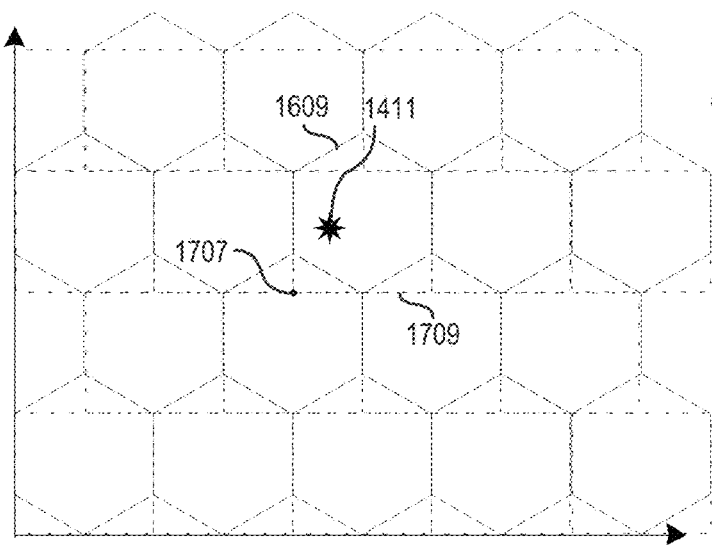
FIGS. 17A and 17B are schematic diagrams illustrating overlaying a staggered rectangular tile array over the hexagonal tile array of FIGS. 16A and 16B, in accordance with one embodiment.

To solve this problem, the array of hexagonal tiles 1601 may be superimposed on or by a second array of staggered rectangular tiles 1705, in such a way as to make an "inverted house" diagram within each rectangle, as clearly illustrated in FIG. 17A, namely defining three linearly segregated tile regions for each rectangular tile, one region predominantly associated with a main underlying hexagonal tile, and two other opposed triangular regions associated with adjacent underlying hexagonal tiles. In doing so, the nestled hexagonal tile geometry is translated to a rectangular tile geometry having distinct linearly segregated tile regions defined therein by the edges of underlying adjacently disposed hexagonal tiles. Again, while regular hexagons are used to represent the generally nestled hexagonal LFSL element array geometry, other nestled tile geometries may be used to represent different nestled element geometries. Likewise, while a nestled array is shown in this example, different staggered or aligned geometries may also be used, in some examples, in some respects, with reduced complexity, as further described below.

Furthermore, while this particular example encompasses the definition of linearly defined tile region boundaries, other boundary types may also be considered provided they are amenable to the definition of one or more conditional statements, as illustrated below, that can be used to output a corresponding set of binary or Boolean values that distinctly identify a location of a given point within one or another of these regions, for instance, without invoking, or by limiting, processing demands common to branching or looping decision logics/trees/statements/etc.

Figure 17B:
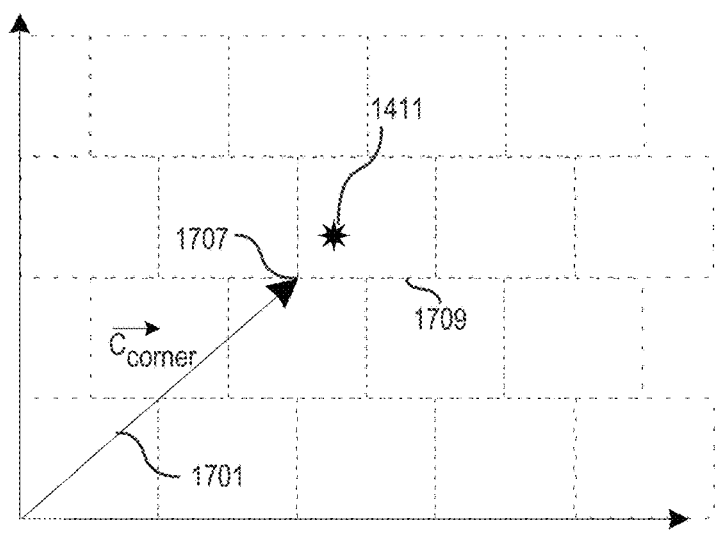

Following with hexagonal example, to locate the associated hexagon tile center 1615 closest to the intersection point 1411, in step 1517, the method first computes the 2D position of the bottom left corner 1707 of the associated (normalized) rectangular tile element 1709 containing intersection point 1411, as shown in FIG. 17B, which can be calculated without using any branching statements by the following two equations (here in normalized coordinates wherein each rectangle has a height and width of one unit):

$$\vec{t} = (\text{poor}(uv_y), 0)$$

$$\vec{C}_{Corner} = (\vec{uv} + \vec{t}) - \vec{t}$$

where $(\vec{uv})$ is the position vector of intersection point 1411 in the common frame of reference of the hexagonal and staggered rectangular tile arrays, and the floor( ) function returns the greatest integer less than or equal to each of the xy coordinates of $\vec{uv}$.

Figure 18A:
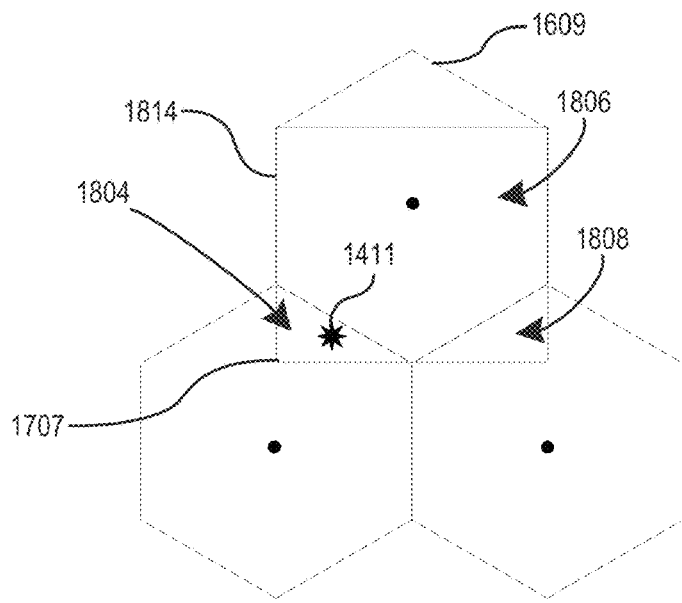
FIGS. 18A to 18C are schematic diagrams illustrating the associated regions of neighboring hexagonal tiles within a single rectangular tile, in accordance with one embodiment.
Figure 18B:
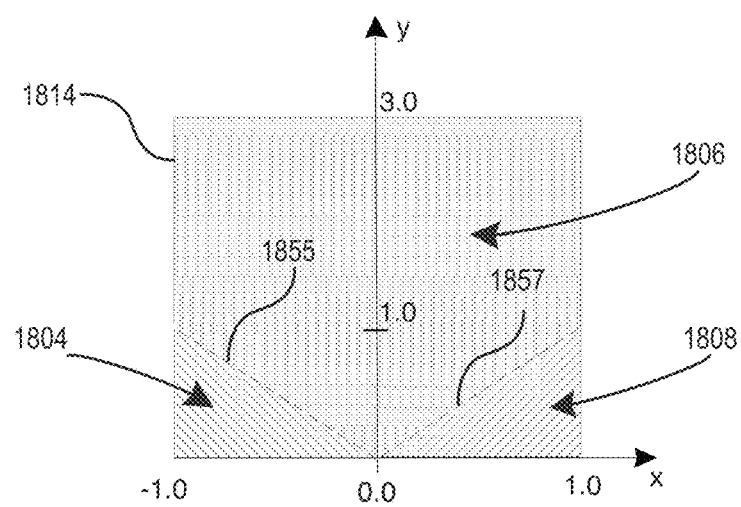
Figure 18C:
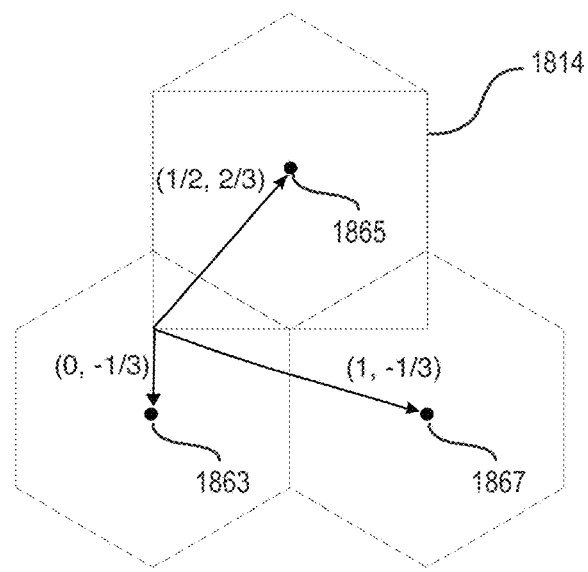

Once the position of lower left corner 1707, indicated by vector $\vec{C}_{corner}$ 1701, of the associated rectangular element 1814 containing the intersection point 1411 is known, three regions 1804, 1806 and 1807 within this rectangular element 1814 may be distinguished, as shown in FIGS. 18A to 18C. Each region is associated with a different hexagonal tile, as shown in FIG. 18A, namely, each region is delineated by the linear boundaries of adjacent underlying hexagonal tiles to define one region predominantly associated with a main hexagonal tile, and two opposed triangular tiles defined by adjacent hexagonal tiles on either side of this main tile. As will be appreciated by the skilled artisan, different hexagonal or nestled tile geometries will result in the delineation of different rectangular tile region shapes, as will different boundary profiles (straight vs. curved) will result in the definition of different boundary value statements, defined further below.

Continuing with the illustrated example, in step 1519, the coordinates within associated rectangular tile 1814 are again rescaled, as shown on the axis of FIG. 18B, so that the intersection point's location, within the associated rectangular tile, is now represented in the rescaled coordinates by a vector $\vec{d}$ where each of its x and y coordinates are given by:

$$d_x = 2*(uv_x - C_{corner_x}) - 1$$

$$d_y = 3*(uv_y - C_{corner_y}).$$

Thus, the possible x and y values of the position of intersection point 1411 within associated rectangular tile 1814 are now contained within −1<x<1 and 0<y<3. This will make the next step easier to compute.

To efficiently find the region encompassing a given intersection point in these rescaled coordinates, the fact that, within the rectangular element 1814, each region is separated by a diagonal line is used. For example, this is illustrated in FIG. 18B, wherein the lower left region 1804 is separated from the middle "inverted house" region 1806 and lower right region 1808 by a downward diagonal line 1855, which in the rescaled coordinates of FIG. 18B, follows the simple equation y=−x. Thus, all points where x<−y are located in the lower left region. Similarly, the lower right region 1808 is separated from the other two regions by a diagonal line 1857 described by the equation y<x. Therefore, in step 1521, the associated region containing the intersection point is evaluated by using these two simple conditional statements. The resulting set of two Boolean values will thus be specific to the region where the intersection point is located. For example, the checks (caseL=x<y, caseR=y<x) will result in the values (caseL=true, caseR=false), (caseL=false, caseR=true) and (caseL=false, caseR=false) for intersection points located in the lower left region 1804, lower right region 1808 and middle region 1806, respectively. One may then convert these Boolean values to floating points values, wherein usually in most programming languages true/false Boolean values are converted into 1.0/0.0 floating point values. Thus, one obtains the set (caseL, caseR) of values of (1.0, 0.0), (0.0, 1.0) or (0.0, 0.0) for each of the described regions above.

To finally obtain the relative coordinates of the hexagonal center associated with the identified region, in step 1523, the set of converted Boolean values may be used as an input to a single floating point vectorial function operable to map each set of these values to a set of xy coordinates of the associated element center. For example, in the described embodiment and as shown in FIG. 18C, one obtains the relative position vectors of each hexagonal center $\vec{r}$ with the vectorial function:

$$\vec{r}=(r_x,r_y)=(0.5+0.5*(\text{case}\vec{R}-\text{case}\vec{L}),\tfrac{2}{3}-(\text{case}R-\text{case}L))$$

thus, the inputs of (1.0, 0.0), (0.0, 1.0) or (0.0, 0.0) map to the positions (0.0, −⅓), (0.5, ⅔), and (1.0, −⅓), respectively, which corresponds to the shown hexagonal centers 1863, 1865 and 1867 shown in FIG. 18C, respectively, in the rescaled coordinates.

Now back to FIG. 15, we may proceed with the final step 1525 to translate the relative coordinates obtained above to absolute 3D coordinates with respect to the display or similar (i.e. in mm). First, the coordinates of the hexagonal tile center and the coordinates of the bottom left corner are added to get the position of the hexagonal tile center in the optical layer's frame of reference. As needed, the process may then scale back the values into absolute units (i.e. mm) and rotate the coordinates back to the original frame of reference with respect to the display to obtain the 3D positions (in mm) of the optical layer element's center with respect to the display's frame of reference, which is then fed into step 1116.

The skilled artisan will note that modifications to the above-described method may also be used. For example, the staggered grid shown in FIG. 17A may be translated higher by a value of ⅓ (in normalized units) so that within each rectangle the diagonals separating each region are located on the upper left and right corners instead. The same general principles described above still applies in this case, and the skilled technician will understand the minimal changes to the equations given above will be needed to proceed in such a fashion. Furthermore, as noted above, different LFSL element geometries can result in the delineation of different (normalized) rectangular tile regions, and thus, the formation of corresponding conditional boundary statements and resulting binary/Boolean region-identifying and center-locating coordinate systems/functions.

In yet other embodiments, wherein a rectangular and/or square microlens array is used instead of a nestled (hexagonal) array, a slightly different method may be used to identify the associated LFSL element (microlens) center (step 1114). Herein, the microlens array is represented by an array of rectangular and/or square tiles. The method, as previously described, goes through step 1515, where the x and y coordinates are rescaled (normalized) with respect to a microlens x and y dimension (henceforth giving each rectangular and/or square tile a width and height of 1 unit). However, at step 1517, the floor( ) function is used directly on each x and y coordinates of $\vec{u}v$ (the position vector of intersection point 1411) to find the coordinates of the bottom left corner associated with the corresponding square/rectangular tile. Therefrom, the relative coordinates of the tile center from the bottom left corner are added directly to obtain the final scaled position vector:

$$\vec{r}=(r_x,r_y)=(\text{floor}(uv_x)+0.5,\text{floor}(uv_y)+0.5)$$

Once this vector is known, the method goes directly to step 1525 where the coordinates are scaled back into absolute units (i.e. mm) and rotated back to the original frame of reference with respect to the display to obtain the 3D positions (in mm) of the optical layer element's center with respect to the display's frame of reference, which is then fed into step 1116.

The light field rendering methods described above (from FIGS. 11 to 20D) may also be applied, in some embodiments, at a subpixel level in order to achieve an improved light field image resolution. Indeed, a single pixel on a color subpixelated display is typically made of several color primaries, typically three colored elements—ordered (on various displays) either as blue, green and red (BGR) or as red, green and blue (RGB). Some displays have more than three primaries such as the combination of red, green, blue and yellow (RGBY) or red, green, blue and white (RGBW), or even red, green, blue, yellow and cyan (RGBYC). Subpixel rendering operates by using the subpixels as approximately equal brightness pixels perceived by the luminance channel. This allows the subpixels to serve as sampled image reconstruction points as opposed to using the combined subpixels as part of a "true" pixel. For the light field rendering methods as described above, this means that the center position of a given pixel (e.g. pixel 1401 in FIG. 14) is replaced by the center positions of each of its subpixel elements. Therefore, the number of color samples to be extracted is multiplied by the number of subpixels per pixel in the digital display. The methods may then follow the same steps as described above and extract the associated image portions of each subpixel individually (sequentially or in parallel).

Figure 21A:
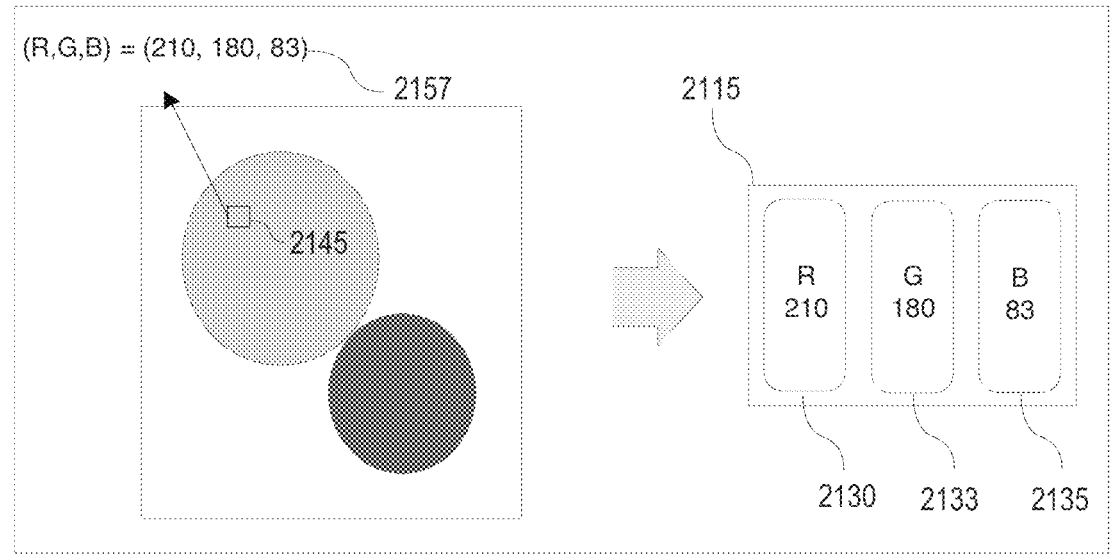
FIGS. 21A and 21B are schematic diagrams illustrating pixel and subpixel rendering, respectively, in accordance with some embodiments.
Figure 21B:
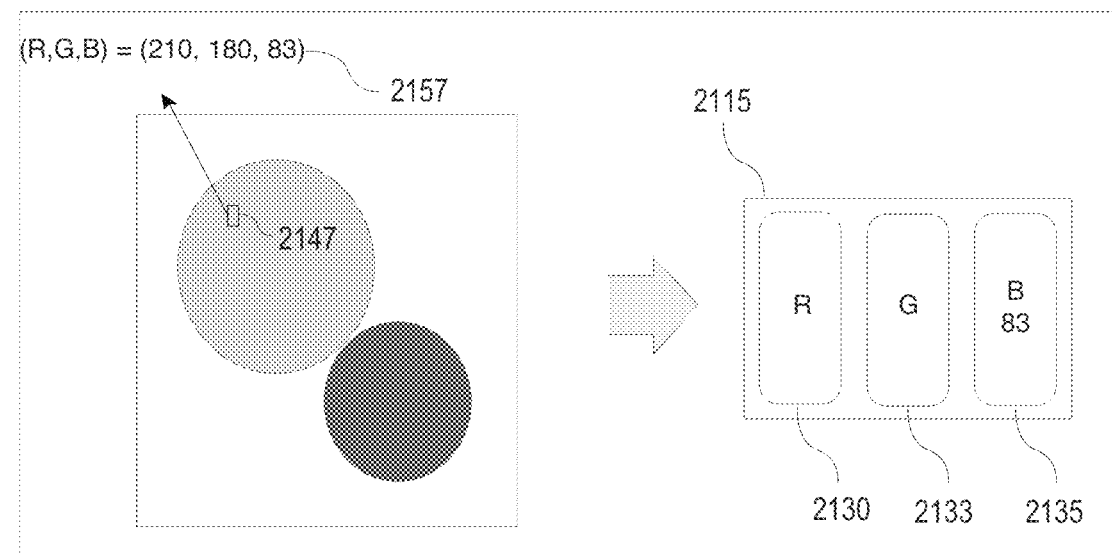

In FIG. 21A, an exemplary pixel 2115 is comprised of three RBG subpixels (2130 for red, 2133 for green and 2135 for blue). Other embodiments may deviate from this color partitioning, without limitation. When rendering per pixel, as described in FIG. 11 or in FIG. 19, the image portion 2145 associated with said pixel 2115 is sampled to extract the luminance value of each RGB color channels 2157, which are then all rendered by the pixel at the same time. In the case of subpixel rendering, as illustrated in FIG. 21B, the methods find the image portion 2147 associated with blue subpixel 2135. Therefore, only the subpixel channel intensity value of RGB color channels 2157 corresponding to the target subpixel 2135 is used when rendering (herein the blue subpixel color value, the other two values are discarded). In doing so, a higher adjusted image resolution may be achieved for instance, by adjusting adjusted image pixel colours on a subpixel basis, and also optionally discarding or reducing an impact of subpixels deemed not to intersect or to only marginally intersect with the user's pupil.

Figures 22A, 22B:
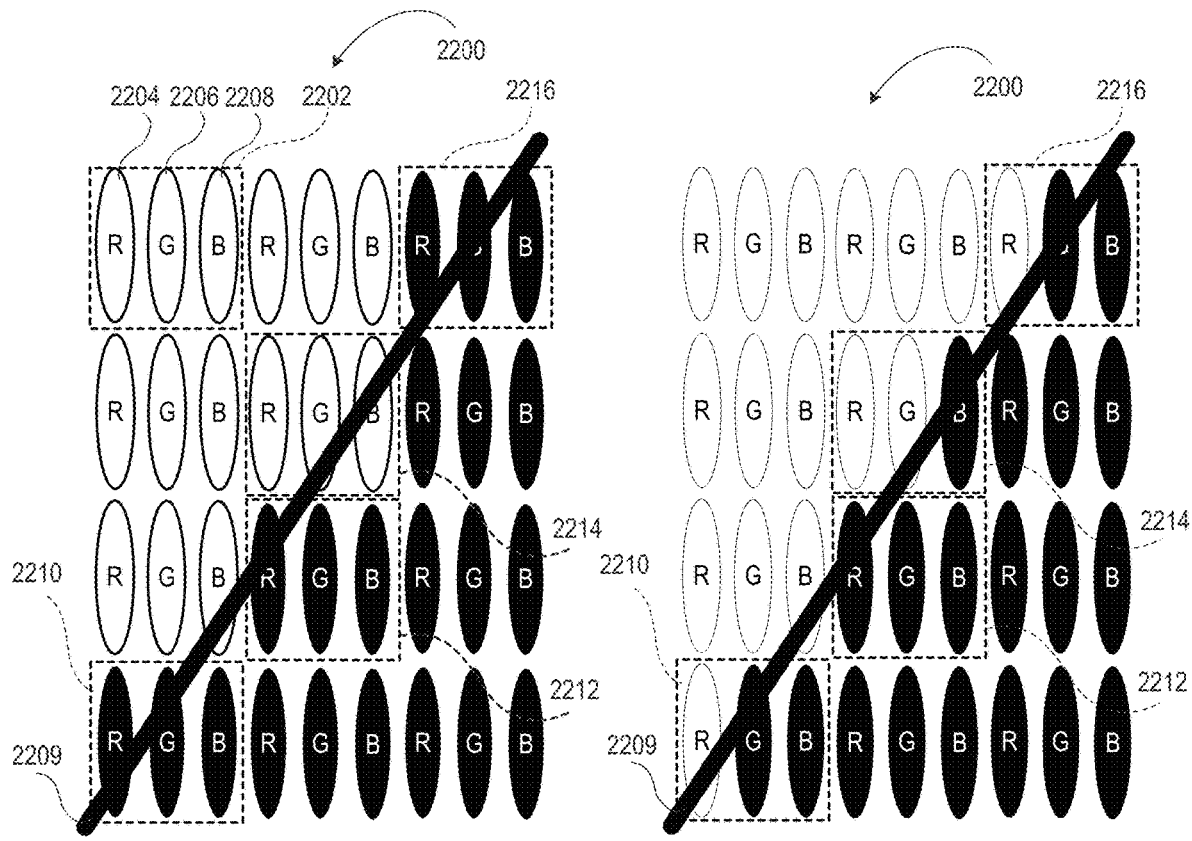
FIGS. 22A and 22B are schematic diagrams of an LCD pixel array defined by respective red (R), green (G) and blue (B) subpixels, and rendering an angular image edge using pixel and subpixel rendering, respectively, in accordance with one embodiment.

To further illustrate embodiments making use of subpixel rendering, with reference to FIGS. 22A and 22B, a (LCD) pixel array 2200 is schematically illustrated to be composed of an array of display pixels 2202 each comprising red (R) 2204, green (G) 2206, and blue (B) 2208 subpixels. As with the examples provided above, to produce a light field display, a light field shaping layer, such as a microlens array, is to be aligned to overlay these pixels such that a corresponding subset of these pixels can be used to predictably produce respective light field rays to be computed and adjusted in providing a corrected image. To do so, the light field ray ultimately produced by each pixel can be calculated knowing a location of the pixel (e.g. x,y coordinate on the screen), a location of a corresponding light field element through which light emanating from the pixel will travel to reach the user's eye(s), and optical characteristics of that light field element, for example. Based on those calculations, the image correction algorithm will compute which pixels to light and how, and output subpixel lighting parameters (e.g. R, G and B values) accordingly. As noted above, to reduce computation load, only those pixels producing rays that will interface with the user's eyes or pupils may be considered, for instance, using a complementary eye tracking engine and hardware, though other embodiments may nonetheless process all pixels to provide greater buffer zones and/or a better user experience.

In the example shown in FIG. 22A, an angular edge 2209 is being rendered that crosses the surfaces of affected pixels 2210, 2212, 2214 and 2216. Using standard pixel rendering, each affected pixel is either turned on or off, which to some extent dictates a relative smoothness of the angular edge 2209.

In the example shown in FIG. 22B, subpixel rendering is instead favoured, whereby the red subpixel in pixel 2210, the red and green subpixels in pixel 2214 and the red subpixel in pixel 2216 are deliberately set to zero (0) to produce a smoother representation of the angular edge 2209 at the expense of colour trueness along that edge, which will not be perceptible to the human eye given the scale at which these modifications are being applied. Accordingly, image correction can benefit from greater subpixel control while delivering sharper images.

In order to implement subpixel rendering in the context of light field image correction, in some embodiments, ray tracing calculations must be executed in respect of each subpixel, as opposed to in respect of each pixel as a whole, based on a location (x,y coordinates on the screen) of each subpixel. Beyond providing for greater rendering accuracy and sharpness, subpixel control and ray tracing computations may accommodate different subpixel configurations, for example, where subpixel mixing or overlap is invoked to increase a perceived resolution of a high resolution screen and/or where non-uniform subpixel arrangements are provided or relied upon in different digital display technologies.

Figure 23:
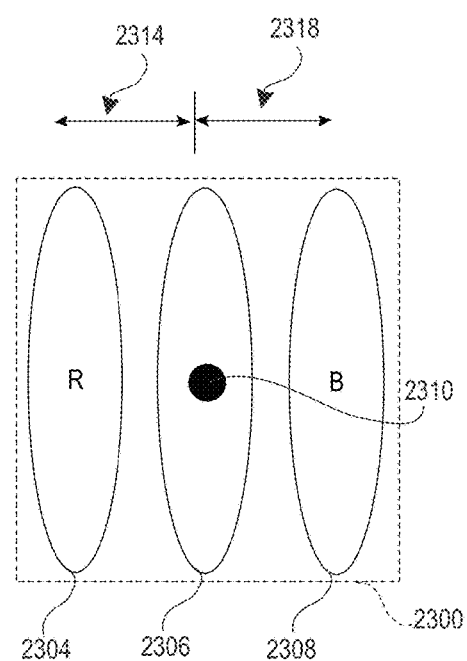
FIG. 23 is a schematic diagram of one of the pixels of FIG. 22A, showing measures for independently accounting for subpixels thereof to apply subpixel rendering to the display of a corrected image through a light field display, in accordance with one embodiment.

In some embodiments, however, in order to avoid or reduce a computation load increase imparted by the distinct consideration of each subpixel, some computation efficiencies may be leveraged by taking into account the regular subpixel distribution from pixel to pixel, or in the context of subpixel sharing and/or overlap, for certain pixel groups, lines, columns, etc. With reference to FIG. 23, a given pixel 2300, much as those illustrated in FIGS. 22A and 22B, is shown to include horizontally distributed red (R) 2304, green (G) 2306, and blue (B) 2308 subpixels. Using standard pixel rendering and ray tracing, light emanating from this pixel can more or less be considered to emanate from a point located at the geometric center 2310 of the pixel 2300. To implement subpixel rendering, ray tracing could otherwise be calculated in triplicate by specifically addressing the geometric location of each subpixel. Knowing the distribution of subpixels within each pixel, however, calculations can be simplified by maintaining pixel-centered computations and applying appropriate offsets given known geometric subpixel offsets (i.e. negative horizontal offset 2314 for the red subpixel 2304, a zero offset for the green 2306 and a positive horizontal offset 2318 for the blue subpixel 2308). In doing so, light field image correction can still benefit from subpixel processing without significantly increased computation load.

While this example contemplates a linear (horizontal) subpixel distribution, other 2D distributions may also be considered without departing from the general scope and nature of the present disclosure. For example, for a given digital display screen and pixel and subpixel distribution, different subpixel mappings can be determined to define respective pixel subcoordinate systems that, when applied to standard pixel-centric ray tracing and image correction algorithms, can allow for subpixel processing and increase image correction resolution and sharpness without undue processing load increases.

In some embodiments, additional efficiencies may be leveraged on the GPU by storing the image data, for example image 1306, in the GPU's texture memory. Texture memory is cached on chip and in some situations is operable to provide higher effective bandwidth by reducing memory requests to off-chip DRAM. Specifically, texture caches are designed for graphics applications where memory access patterns exhibit a great deal of spatial locality, which is the case of the steps 1110-1126 of method 1100. For example, in method 1100, image 1306 may be stored inside the texture memory of the GPU, which then greatly improves the retrieval speed during step 1126 where the color channel associated with the portion of image 1306 at intersection point 1423 is determined.

Figure 38A:
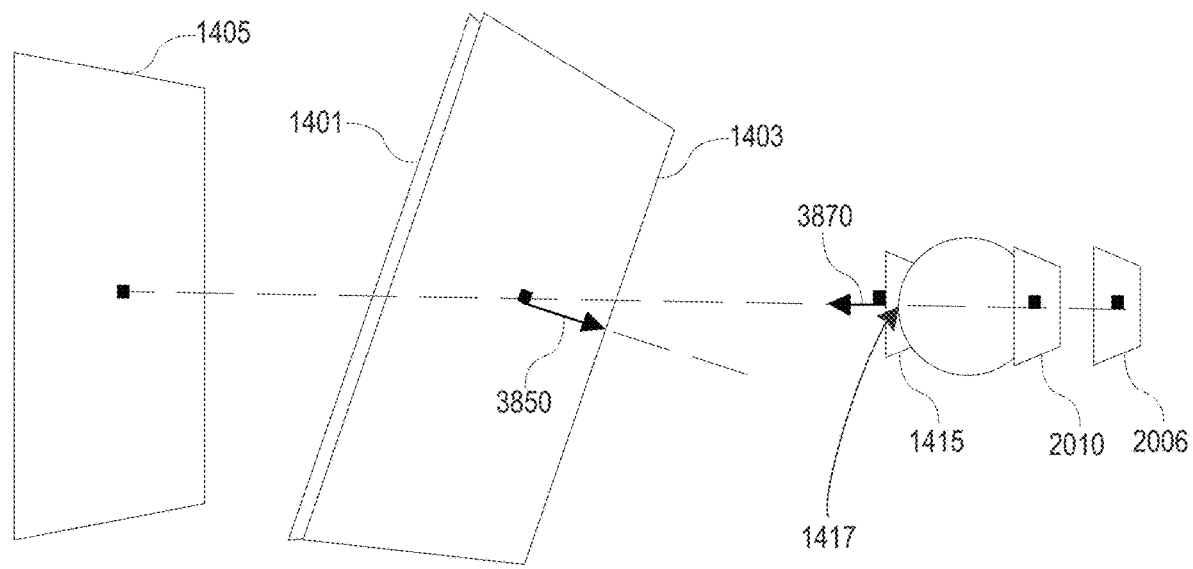
FIGS. 38A and 38B are schematic diagrams illustrating ray-tracing in the context of non-parallel planes, in accordance with one embodiment.
Figure 38B:
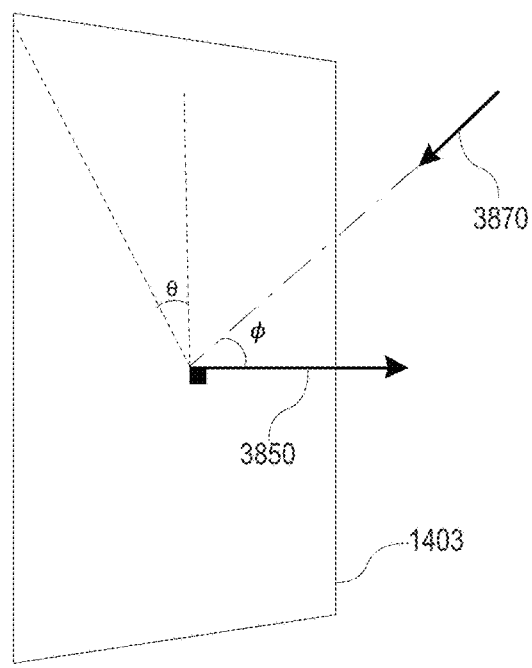

With reference to FIGS. 38A and 38B, and in accordance with one exemplary embodiment, ray-tracing with non-parallel planes will now be discussed. In FIGS. 39A to 39C and FIGS. 20A to 20D, the different planes illustrated (e.g. pixel display 1401, optical layer 1405, pupil plane 1415, virtual image plane 1405, retina plane 2010 and focal plane 2006) were all shown as being parallel to one another to better describe the ray-tracing methodology associated therewith. However, the corresponding ray-tracing methods 1100 of FIG. 11 and 1900 of FIG. 19, as described above, may also be applied to account for changes in the relative orientation between any one of those planes.

In some embodiments, and as illustrated in FIG. 38A, cases may be considered wherein the user is viewing the light field display at an angle. In this specific example, the ray-tracing method can therefore account for a change in orientation of the pupil plane 1415 with respect to the pixel display 1401 and optical layer 1405. In this example, other planes such as virtual image plane 1405 (used in the ray-tracing method of FIG. 11), and retina plane 2010 and focal plane 2006 (used in the ray-tracing method of FIG. 19) may be taken to be parallel to pupil plane 1415. The relative difference in orientation between the two sets of planes is illustrated by using vector 3850 which is the normal vector to the plane of corresponding optical layer 1403, and vector 3870 which is the normal vector to pupil plane 1415. The relative orientation between the two normal vectors is illustrated in FIG. 38B, using polar and azimuthal angles.

The general orientation of pupil plane 1415 may be parametrized, for example, by using the 3D location of pupil center 1417 and a corresponding normal vector 1415. Normal vector 1415 may be taken to be, in some embodiments, equal to the gaze direction as measured by a gaze tracking system or similar, as will be discussed below.

Once the relative position and orientation of pupil plane 1415 is determined, the relative position/orientation of all remaining planes (parallel or non-parallel) may be determined and parametrized accordingly. Planes that are parallel share the same normal vector. From there, the methods of FIGS. 11 and 19 can be applied by finding the intersection point between an arbitrary vector and an arbitrarily oriented plane, as is done for example at steps 1112, 1118, 1124 of the method of FIG. 11, and steps 1912, 1918, 1923, 1925 of the method of FIG. 19.

In the illustrated example of FIG. 38A, the position of virtual image plane 1405 may be computed using the minimum reading distance 1310 (and/or related parameters) but from the position of pupil plane 1415 and along the direction vector 3870.

To extract normal vector 3870 of pupil plane 1415, the eye tracking methods and systems described above may be used or modified to further provide a measure of the eye's gaze direction (e.g. gaze tracking). As discussed above, there are many known eye tracking methods in the art, some of which may also be used for gaze-tracking. For example, this includes Near-IR glint reflection methods and systems or methods purely based on machine vision methods. Hence, in some embodiments, pupil plane 1415 may be re-parametrized using an updated 3D location of pupil center 1417 and an updated normal vector 3870 at each eye tracking cycle. In other embodiments, a hybrid gaze tracking/pupil tracking system or method may be used wherein gaze direction (e.g. normal vector 3870) is provided at a different interval than pupil center location 1417. For example, in some embodiments, for one or more cycles, only the 3D pupil center location 1417 may be measured and an old gaze direction vector may be re-used or manually updated. In some embodiments, an eye model or similar may be constructed to map a change in measured pupil center location 1417 to a change in the gaze direction vector without relying on the full capabilities of the gaze tracking system or method. Such a map may be based on one or more previous gaze tracking measurements. In any case, by measuring/determining the 3D pupil center location 1417 and normal vector 3870, the pupil plane may be parametrized accordingly.

Note that in FIG. 38A, display 1401 and optical layer 1403 are shown parallel for simplicity, but other embodiments may envision optical layer 1403 to be non-parallel to display 1401 as well. This doesn't change the general scope of the present discussion, as long as the relative angle between them is known. For example, such an angle may be pre-determined during manufacturing or measured in real-time using one or more sensors (for example in the case where optical layer 1403 may be mobile). Similarly, other planes like for example retina plane 2010 may also be made to be non-parallel to the pupil plane, depending on the user's eye geometry.

Figure 39A:
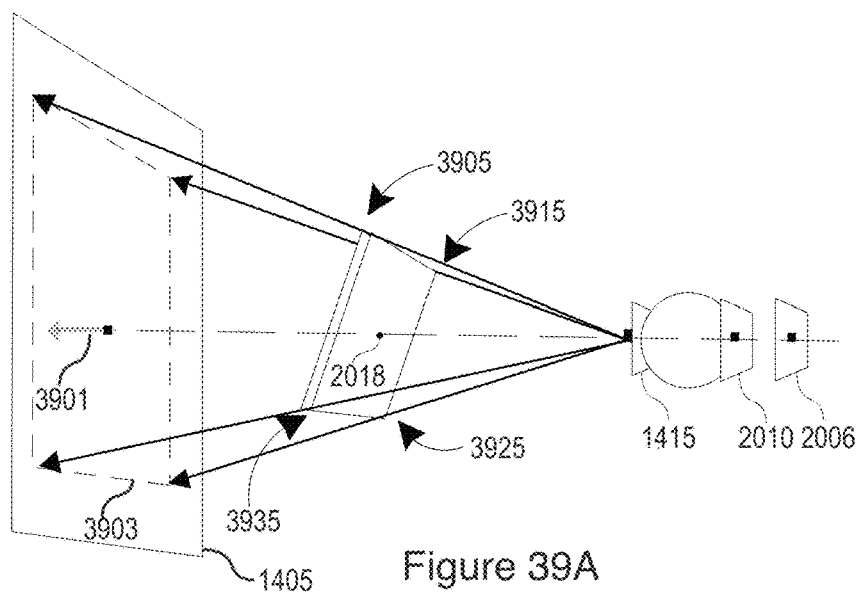
FIGS. 39A to 39C are schematic diagrams illustrating image placement and scaling in the context of non-parallel planes, in accordance with one embodiment.
Figure 39B:
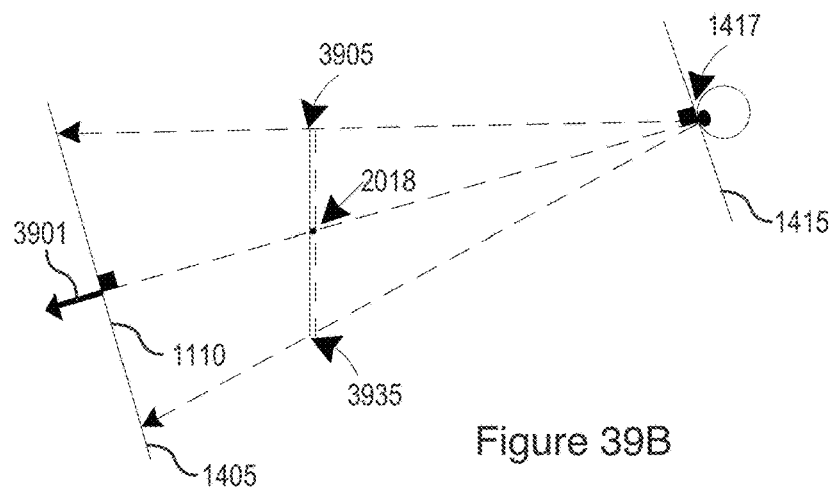
Figure 39C:
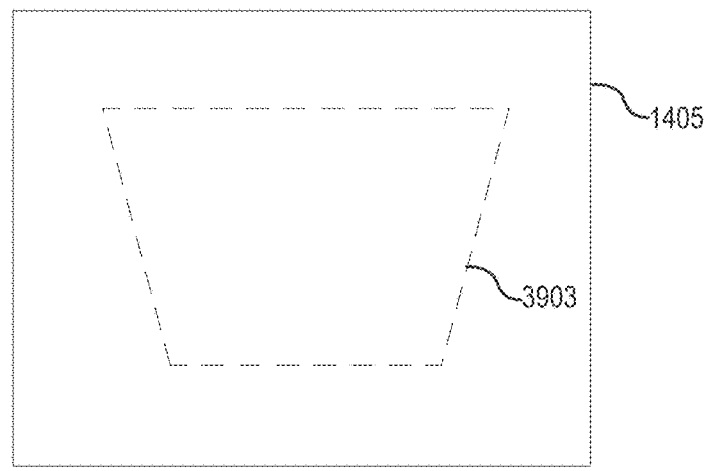
Figure 47:
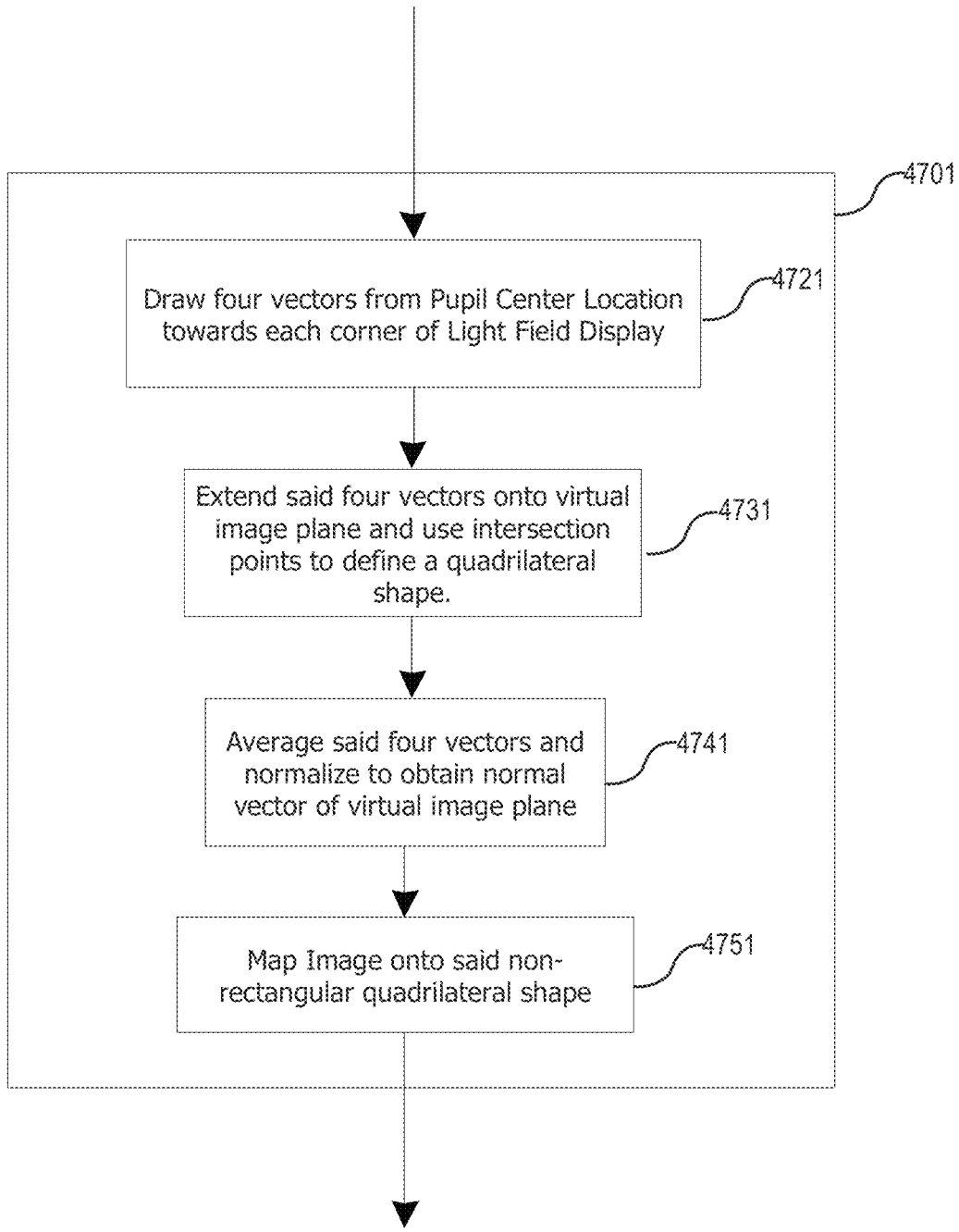
FIG. 47 is a process flow diagram illustrating an exemplary method of ray-tracing in the context of non-parallel planes, in accordance with one embodiment.

With reference to FIG. 47, a method step 4701, which may be used to replace the image scaling step on a virtual image plane, described above for example in steps 1106 and 1108 of methods 1100, and in accordance with one embodiment, will now be described. When dealing with non-parallel planes, in some embodiments, some modifications to steps 1106 and 1108 (or any step which requires to map and scale an image on a virtual plane) may be required. As illustrated in FIG. 47, step 4701 may be decomposed into a number of substeps 4721-4751. At step 4721, the relative orientation of the virtual image plane 1405 with respect to the light field display may be computed by drawing vectors from pupil center 1417 towards the corners of the light field display (for example the corner locations of pixel display 1401). For example, as illustrated in FIGS. 39A and 39B, which mirrors the schematic diagram of FIG. 38A, the user's pupil is located off-axis and will thus be viewing the display at an angle. By assuming that pupil center 1417 is always orientated towards display center location 2018, the position and orientation of virtual image plane 1405 may be derived. For example, by assuming that the user's pupil is always oriented towards display center location 2018, four vectors may be drawn, each from pupil center 1417 towards a distinct corner of pixel display 1401. At step 4731, the corresponding intersection points of these vectors with virtual image plane 1405 will define a convex quadrilateral area 3903 on plane 1405 which is the area onto which the image must be drawn or mapped (in final step 4751) so to fill the display when viewed by user. Moreover, at step 4741, the four vectors may be averaged and normalized, thus giving a normal vector 3901 which indicates the relative orientation of plane 1405. This is illustrated in FIGS. 39A and 39B where we see four vectors originating from pupil center location 1417, each projected towards a corner of the display (points 3905, 3915, 3925 and 3935), which intersect with virtual image plane 1405 to define quadrilateral area 3903. FIG. 39B shows a side view of the schematic diagram of FIG. 39A while FIG. 39C shows convex quadrilateral area 3903 from FIG. 39A from the front.

As mentioned above, non-parallel configurations, as those illustrated in FIG. 39A, may require additional treatment when scaling the image on the virtual image plane 1405 so to fill the entire light field display when viewed by the user. Indeed, non-parallel planes resulting from an off-axis pupil center position 1417 may require that the image be processed or converted to fit onto non-rectangular area 3903. Thus, at step 4751, different texture mapping and interpolation techniques may be used to deform or stretch an image texture onto non-rectangular shape 3903. For example, and without limitation, these may include bilinear interpolation.

With reference to FIGS. 24 to 26D, and in accordance with one embodiment, an exemplary computationally implemented ray-tracing method for rendering multiple images or image portions on multiple adjusted distinct image planes simultaneously via an array of light field shaping elements, or light field shaping layer (LFSL) thereof, will now be described. The previous above-described embodiments were directed to correcting a single image by directly or indirectly modifying the location of the virtual image plane and/or eye focal plane. In contrast, the below-described embodiments are directed to a light field display which is generally operable to display multiple image planes at different locations/depths simultaneously. This enables a user to focus on each plane individually, thus creating a 2.5D effect. Thus, a portion of an image may mask or obscure a portion of another image located behind it depending on the location of the user's pupil (e.g. on an image plane perceived to be located at an increased distance from the display than the one of the first image portion). Other effects may include parallax motion between each image plane when the user moves.

Figure 24:
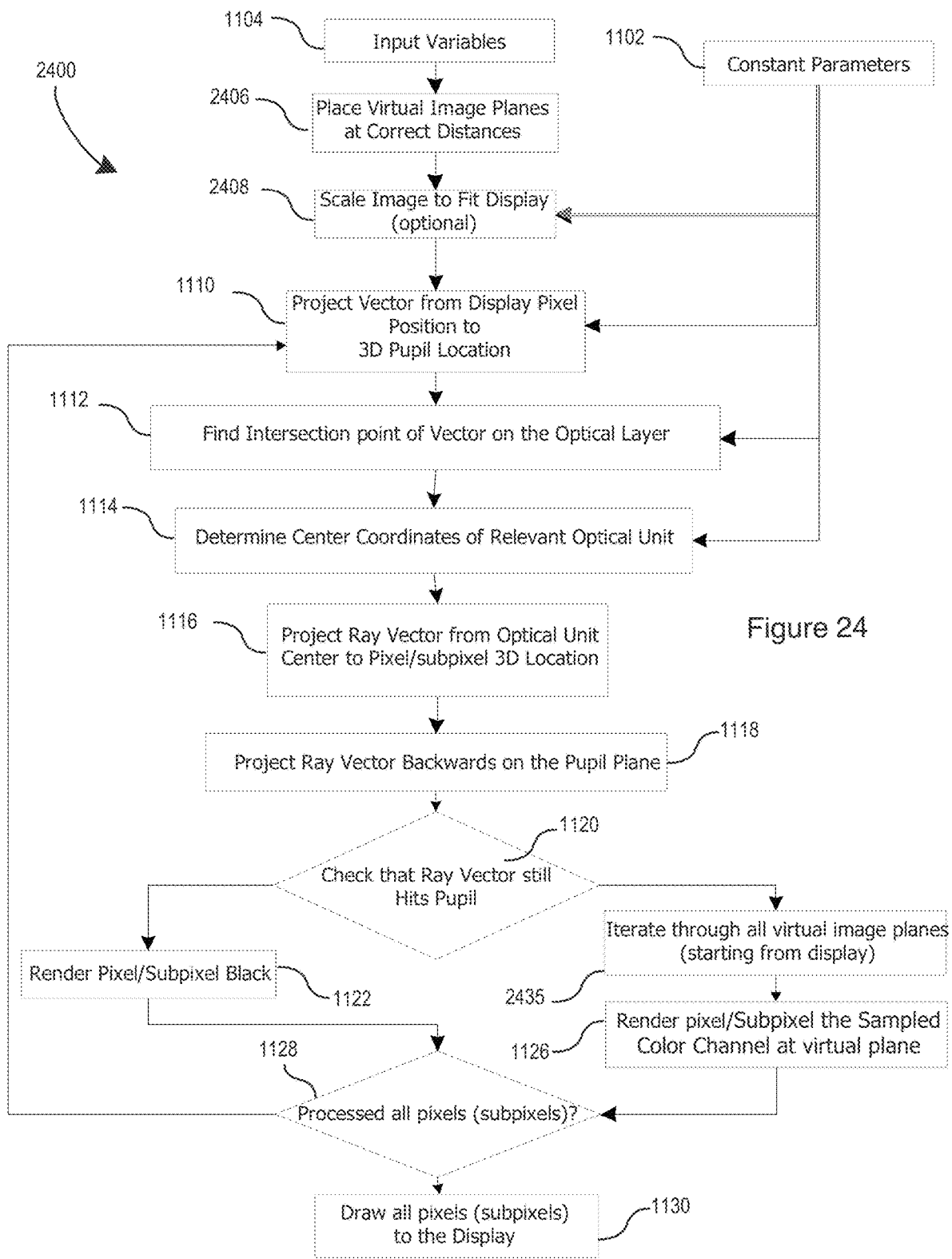
FIG. 24 is a process flow diagram of an illustrative ray-tracing rendering process for rendering a light field originating from multiple distinct virtual image planes, in accordance with one embodiment.

Method 2400 of FIG. 24 substantially mirrors method 1100 of FIG. 11, but generalizes it to include multiple distinct virtual image planes. Thus, new steps 2406, 2408, and 2435 have been added, while steps 1110 to 1122, and 1126 to 1130 are the same as already described above.

For example, to account for multiple distinct image planes, image data 1306 of input variables 1104 may also include depth information. Thus, any image or image portion may have a respective depth indicator. Thus, at step 2406, a set of multiple virtual image planes may be defined. On these planes, images or image portions may be present. Areas around these images may be defined as transparent or see-through, meaning that a user would be able to view through that virtual image plane and see, for example, images or image portions located behind it. At step 2408, any image or image portion on these virtual image planes may be optionally scaled to fit the display.

Figure 26A:
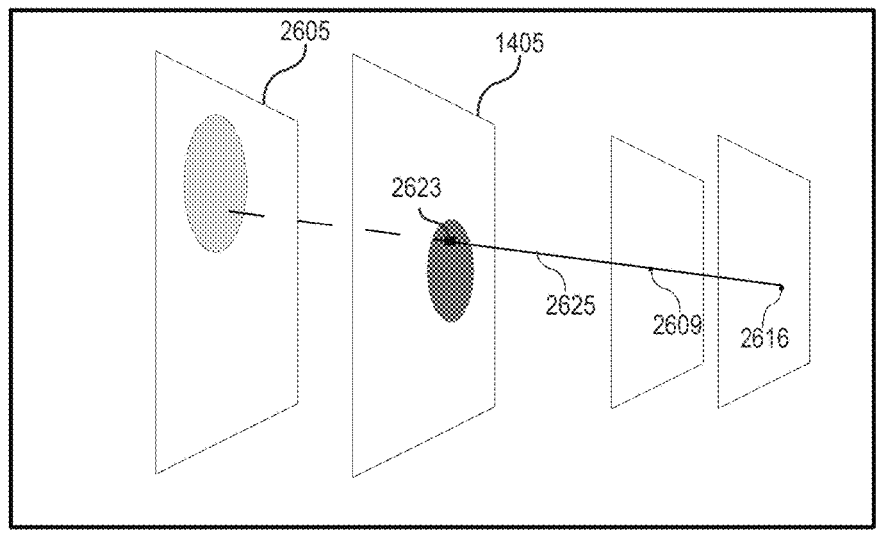
FIGS. 26A to 26D are schematic diagrams illustrating certain process steps of FIG. 25.
Figure 26B:
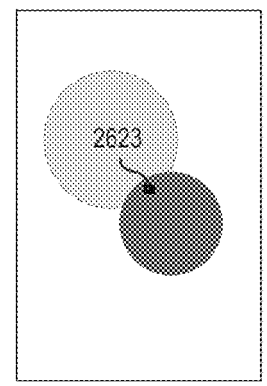

As an example, in the previous example of FIGS. 14A-14C, a single virtual image plane 1405, showing two circles, was shown. In contrast, FIGS. 26A and 26B show an example wherein each circle is located on its own image plane (e.g. original virtual plane 1405 with new virtual image plane 2605). The skilled technician will understand that two planes are shown only as an example and that the method described herein applies equally well to any number of virtual planes. The only effect of having more planes is a larger computational load.

Going back to FIG. 24, steps 1110 to 1122 occur similarly to the ones described in FIG. 11. However, step 1124 has been included and expanded upon in Step 2435, which is described in FIG. 25. In step 2435, an iteration is done over the set of virtual image planes to compute which image portion from which virtual image plane is seen by the user. Thus, at step 2505 a virtual image plane is selected, starting from the plane located closest to the user. Then step 1124 proceeds as described previously for that selected virtual plane. At step 2510 the corresponding color channel of the intersection point identified at step 1124 is sampled. Then at step 2515, a check is made to see if the color channel is transparent. If this is not the case, then the sampled color channel is sent to step 1126 of FIG. 24, which was already described and where the color channel is rendered by the pixel/subpixel. An example of this is illustrated in FIGS. 26A and 26B, wherein a user is located so that a ray vector 2625 computed passing through optical element 2616 and pixel/subpixel 2609 intersects virtual image plane 1405 at location 2623. Since this location is non-transparent, this is the color channel that will be assigned to the pixel/subpixel. However, as this example shows, this masks or hides parts of the image located on virtual image plane 2605. Thus, an example of the image perceived by the user is shown in FIG. 26B.

Figure 25:
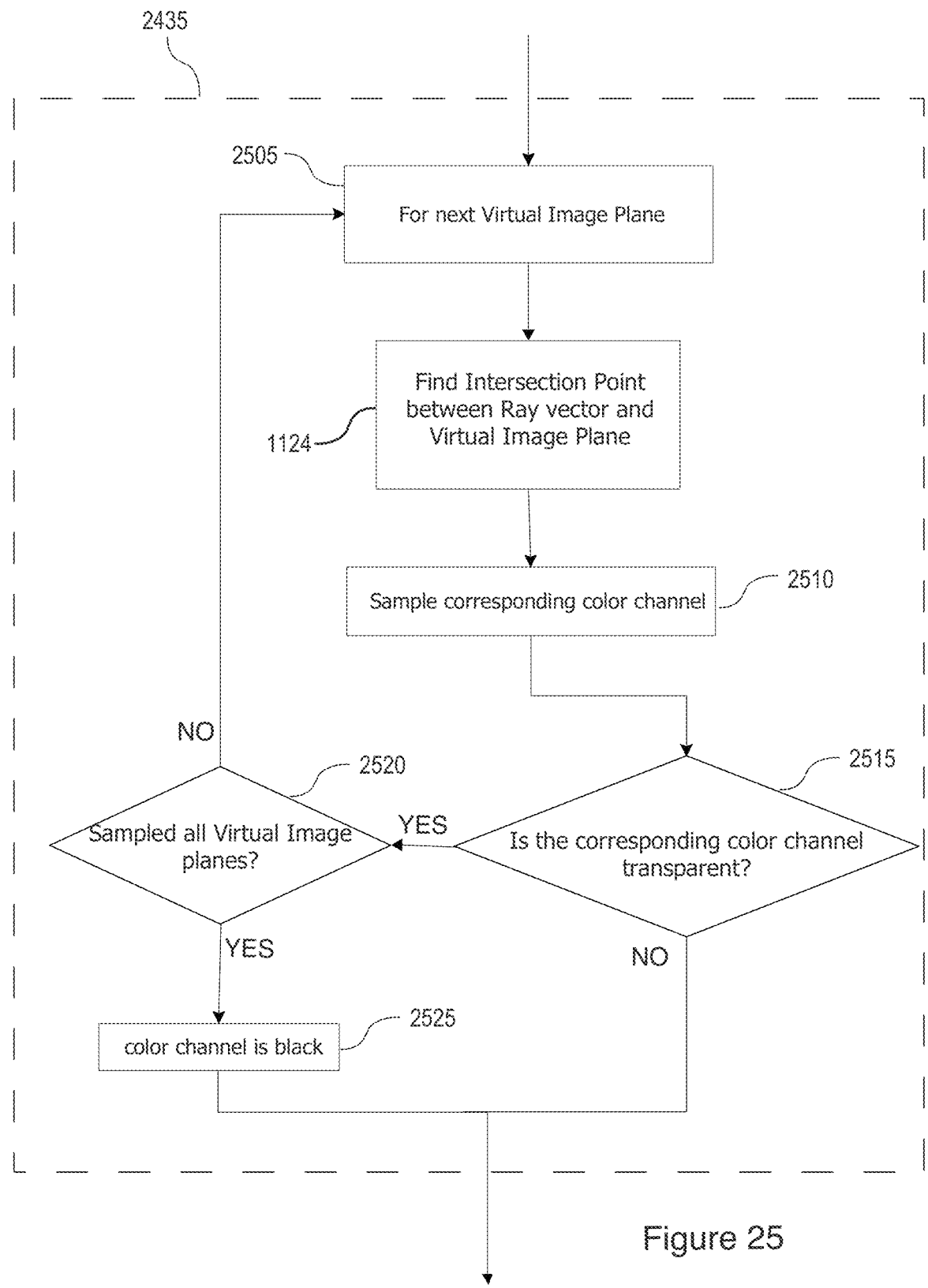
FIG. 25 is a process flow diagram of an exemplary process for iterating over multiple virtual image planes in the ray-tracing rendering process of FIG. 24, in accordance with one embodiment.
Figure 26C:
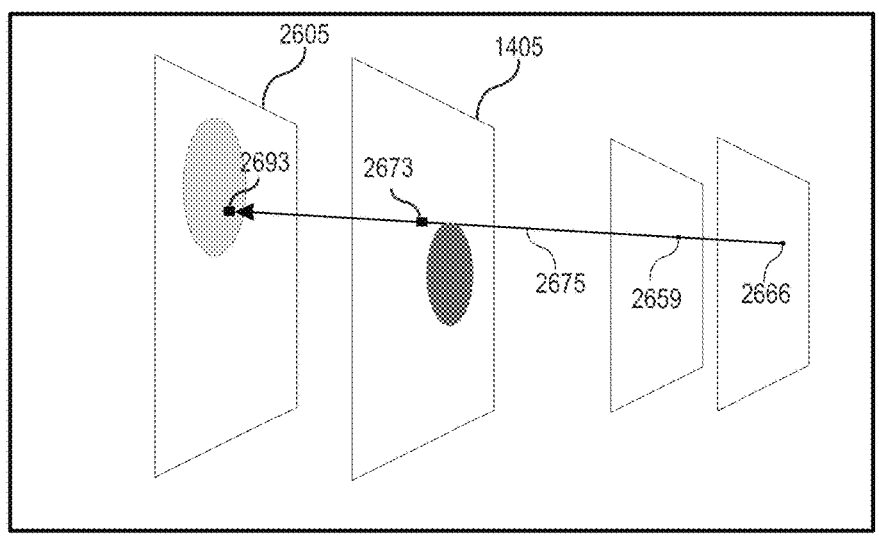
Figure 26D:
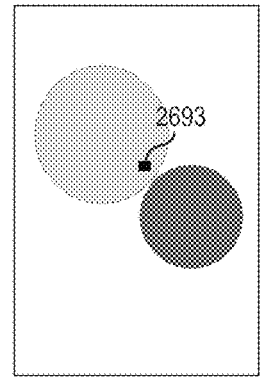

Going back to FIG. 25, at step 2515 if the color channel is transparent, then another check is made at step 2520 to see if all virtual image planes have been iterated upon. If this is the case, then that means that no image or image portion is seen by the user and at step 2525, for example, the color channel is set to black (or any other background colour), before proceeding to step 1126. If however at least one more virtual image plane is present, then the method goes back to step 2505 and selects that next virtual image plane and repeats steps 1124, 2510 and 2515. An example of this is illustrated in FIG. 26C, wherein a user is located so that a distinct ray vector 2675 computed passing through optical element 2666 and pixel/subpixel 2659 first intersects at location 2673 of virtual image plane 1405. This location is defined to be transparent, so the method checks for additional virtual image planes (here plane 2605) and computes the intersection point 2693, which is non-transparent, and thus the corresponding color channel is selected. An example of the image perceived by the user is shown in FIG. 26D.

Going back to FIG. 24, once the pixel/subpixel has been assigned the correct color channel at step 1126, the method proceeds as described previously at steps 1128 and 1130.

Figure 28:
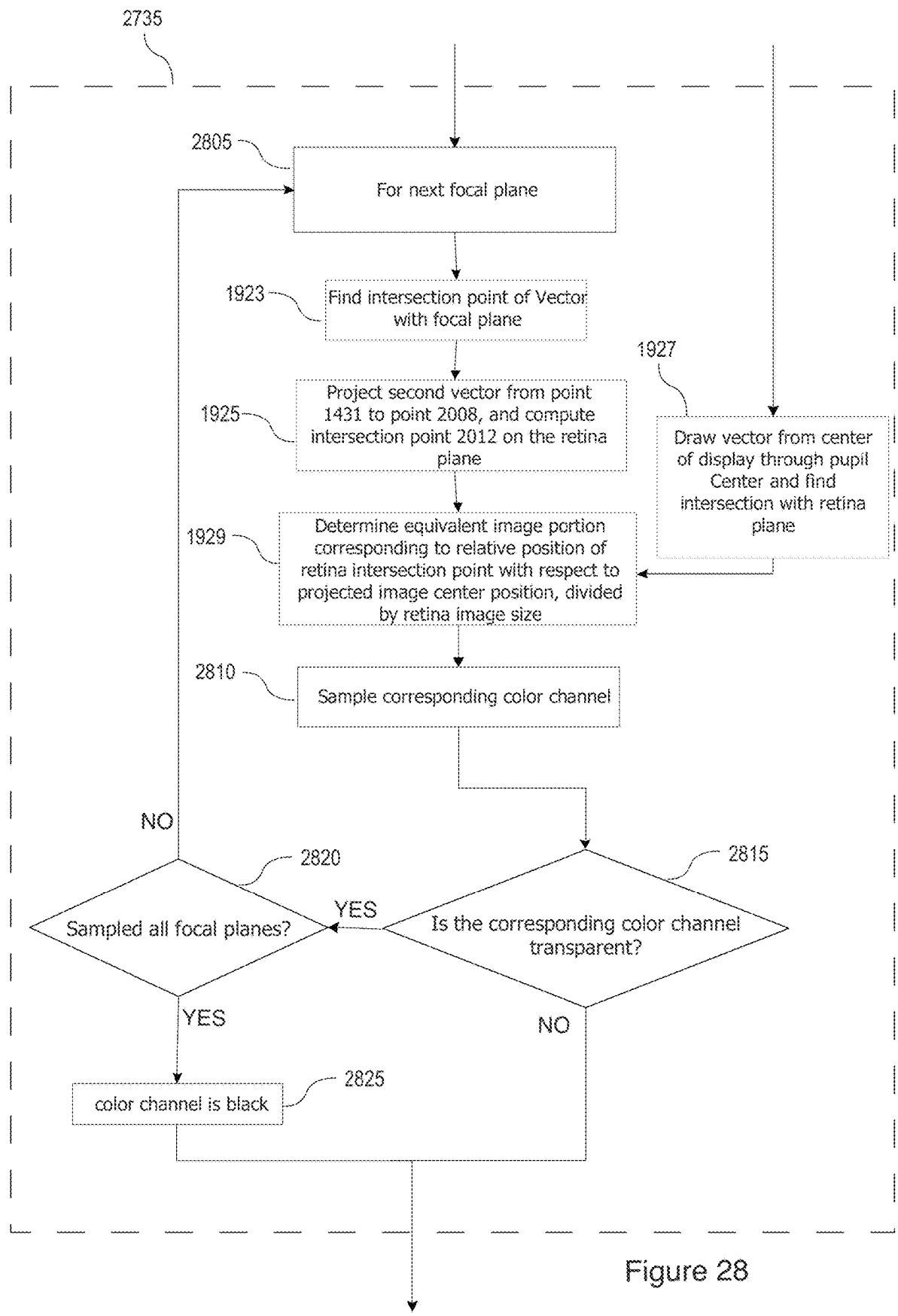
FIG. 28 is a process flow diagram of an exemplary process for iterating over multiple image planes in the ray-tracing rendering process of FIG. 27, in accordance with one embodiment.

Similarly, method 2700 of FIG. 27 substantially mirrors method 1900 of FIG. 19 but also generalizes it to include multiple distinct eye focal planes (each corresponding to a virtual image plane, including infinity, as explained above). Thus, in method 2700, steps 1910 to 1921 and 1931 to 1936 are the same as described for method 1900. The difference comes from new step 2735 which includes and expands upon steps 1921 to 1929, as shown in FIG. 28. There, we see that the method iterates over all designated image planes, each corresponding to a different eye focal plane, starting from the plane corresponding to an image located closest to the user. Thus, a new eye focal plane is selected at step 2805, which is used for steps 1923 to 1929 already described above. Once the corresponding image portion is located at step 1929, at step 2810, the corresponding pixel/subpixel color channel is sampled. Then at step 2815, if the color channel is non-transparent, then the method goes back to step 1931 of FIG. 27, wherein the pixel/subpixel is assigned that color channel. However, if the image portion is transparent, then the method iterates to the eye focal plane corresponding to the next designated image plane. Before this is done, the method checks at step 2820 if all the eye focal planes have been iterated upon. If this is the case, then no image portion will be selected and at step 2825 the color channel is set to black, for example, before exiting to step 1931. If other eye focal planes are still available, then the method goes back to step 2805 to select the next eye focal plane and the method iterates once more.

Figure 29A:
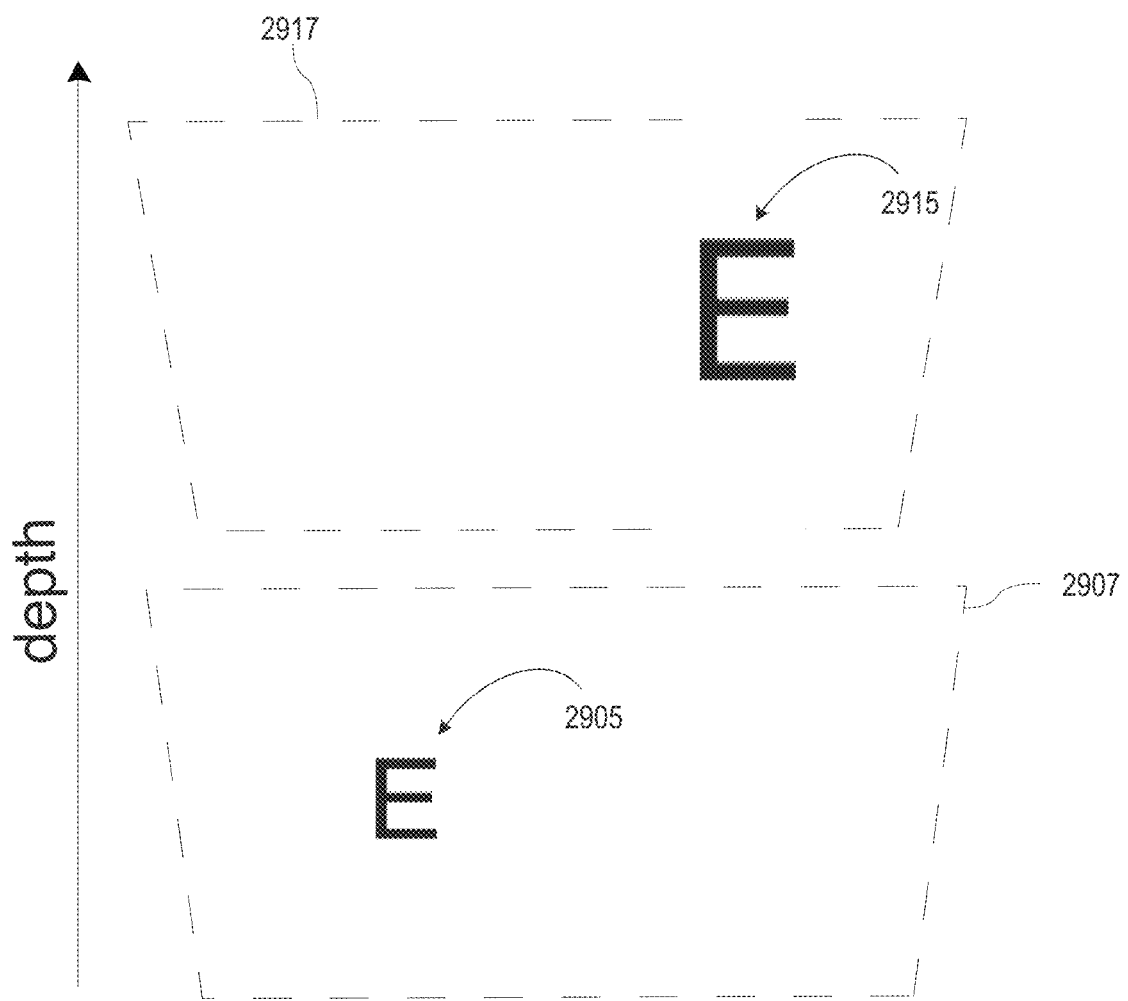
FIGS. 29A and 29B are schematic diagrams illustrating an example of a subjective visual acuity test using the ray-tracing rendering process of FIG. 25 or FIG. 27, in accordance with one embodiment.
Figure 29B:
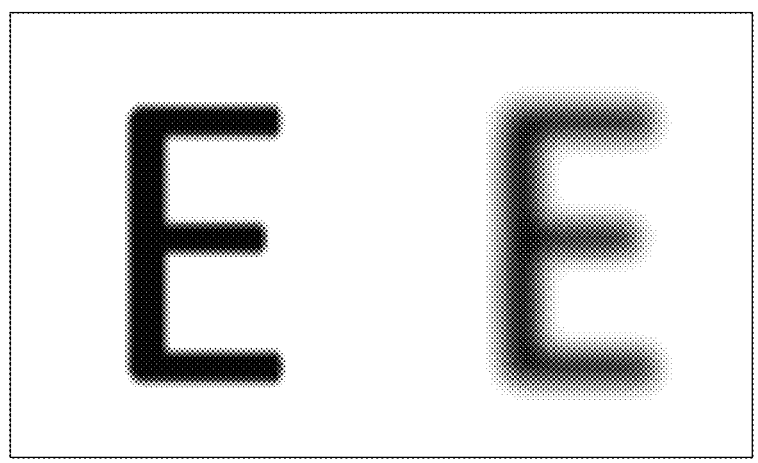

In some embodiments, methods 2400 or 2700 may be used to implement a phoropter/refractor device to do subjective visual acuity evaluations. For example, as illustrated in FIGS. 29A and 29B, different optotypes (e.g. letters, symbols, etc.) may be displayed simultaneously but at different perceived depths, to simulate the effect of adding a refractive optical component (e.g. change in focus/optical power). In FIG. 29A, two images of the same optotype (e.g. letter E) are displayed, each on their own designated image plane (e.g. here illustrated as virtual image planes as an example only). In this example, image 2905 is located on designated image plane 2907 while image 2915 is located on designated image plane 2917, which is located further away. Optionally, as illustrated herein, the size of the image may be increased with increased depth so that all images displayed are perceived to be of a similar relative size by the user. In FIG. 29B, we see an example of the perception of both images as perceived by a user with reduced visual acuity (e.g. myopia), for example, wherein the image closest to the user is seen to be clearer. Thus, a user could be presented with multiple images (e.g. 2 side-by-side, 4, 6 or 9 in a square array, etc.) and indicate which image is clearer and/or and most comfortable to view. An eye prescription may then be derived from this information. Moreover, in general, both spherical and cylindrical power may be induced by the light field display, as will be discussed further below.

Figure 40:
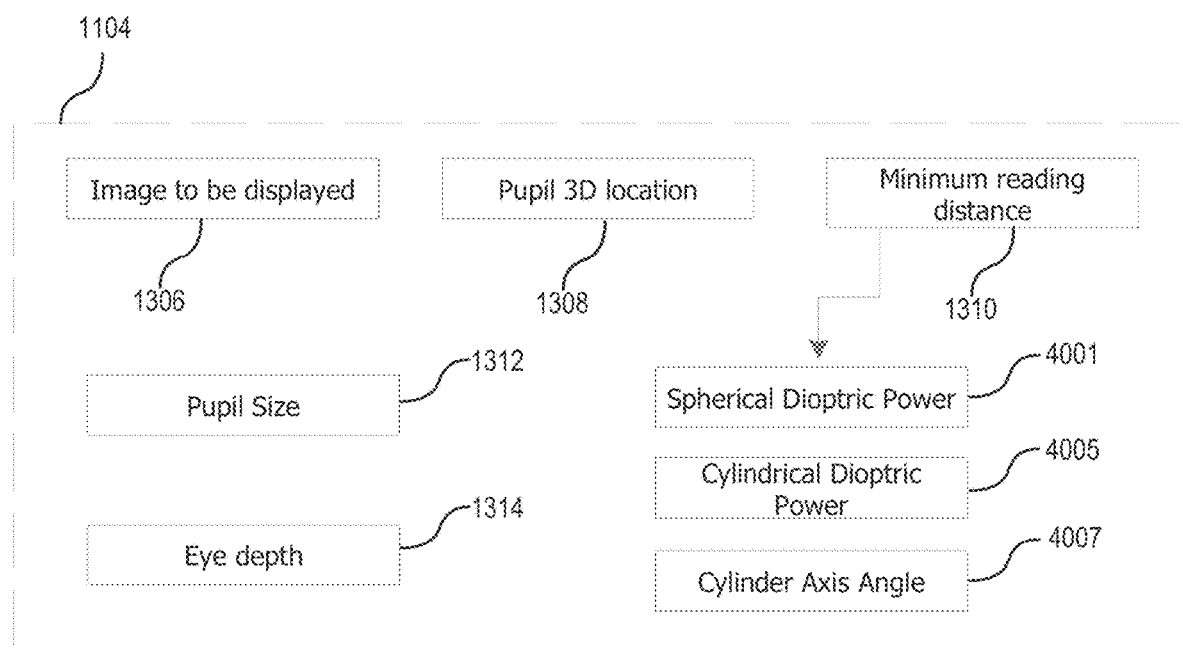
FIG. 40 is a process flow diagram of exemplary input constant parameters for astigmatism compensation, in accordance with one embodiment.

For example, the light field ray-tracing methods of FIGS. 11 and 19 may be readily accommodated to provide changes in cylindrical power, which may be useful in compensating or correcting for astigmatism. As illustrated in FIG. 40, these methods, described in detail below, will use new input variables: cylindrical power 4005 and corresponding cylinder axis angle 4007. In addition, while the minimum reading distance 1310 discussed above inherently parametrized the value of the spherical dioptric power in methods 1100 and 1900, methods 2600 and 2900 below will instead refer, for the methods 4100 and 4300 described below, to the spherical dioptric power 4001 by name (as shown in FIG. 40) for a clearer description and so that the three input variables (spherical dioptric power 4001, cylindrical dioptric power 4003 and cylinder axis angle 4007) mirror the SPHERE, CYL and AXIS parameters used in a typical eye examination.

With reference to FIGS. 41 and 42A-42C and in accordance with one exemplary embodiment, a ray-tracing rendering process for astigmatism compensation, generally referred to using the numeral 4100, will now be described. Method 4100, illustrated in the flow process diagram of FIG. 41, is a modified ray-tracing method similar to the method 1100 of FIG. 11, but further operable to compensate for astigmatism.

Method 4100 mirrors in most part the method 1100, but with step 1106 removed and step 1108 moved after newly introduced steps 4101 and 4105. In this exemplary embodiment, instead of using an initial fixed depth value for virtual image plane 1405 derived from an input minimum reading distance 1310 (which implicitly implied spherical deficiency only), and use that value to place virtual image plane 1405 at the correct location (as in step 1106 of FIG. 11) and scale the image thereon (as in step 1108 in FIG. 11), method 4100 instead proceeds directly with step 1110 through 1120, until an intersection point 4201 (equivalent to intersection point 1431 discussed above) on pupil plane 1415 is computed. Then, from the location of intersection point 4201 relative to an input cylinder axis angle 4007, a combined spherical/cylindrical dioptric power or total dioptric power value may be derived. This total dioptric power may then be converted into a corresponding designated virtual image plane location for this iteration of intersection point 1423. Thus, image scaling on the virtual plane is not done once, but done on a per-pixel basis at each iteration.

Thus, steps 1110 to 1120 of method 4100 proceed as previously described for method 1100, as does step 1122. However, once the location of a new pupil intersection point 1431 is known (for the current pixel iteration) new steps 4101 and 4105 are introduced. At step 4101 a total dioptric power comprising spherical and cylindrical contributions is computed as a function of the intersection point location 1431 on the pupil plane 1415. In some embodiments, astigmatism may be modelled by considering that the eye is a sphero-cylindrical lens having a total refractive power along a given meridian angle θ given by:

$$P(\theta) = S + C \sin^2(\phi - \theta)$$

wherein P is the (total dioptric power), S is the spherical power 4001 (derived from minimum reading distance 1310 for example), C is the cylindrical power 4005, φ the cylinder axis angle 4007 and θ is the angle of the position vector 4208 of point 1431 on the pupil with respect to the x axis in a local pupil frame of reference. This is illustrated schematically in FIG. 42A, wherein we see an exemplary circular pupil entrance 4209 on pupil plane 1415, and the dotted line represents an exemplary orientation of the cylinder axis. In some embodiments, it may also be possible to simulate the presence of two or more cylindrical lenses by summing the corresponding value of $C \sin^2(\phi - \theta)$ computed using each distinct set of cylindrical power 4005 and cylindrical axis angle 4007 values before adding the resulting sum to the spherical power 4001.

In some embodiments, the determination of the cylinder axis angle 4007 with respect to the pupil center location 1417 and intersection point 4201 may require a change of coordinates onto a local pupil frame of reference, for example if the head of the user is tilted or at an angle with respect to the display. When this is not the case, either by approximation or because the user's head is constrained by a head rest or similar (e.g. within the context of an eye testing device), it may be taken that the local pupil frame of reference for which the cylindrical axis parameter is defined is the same as the display frame of reference (used for all vector computations) thus no special treatment is needed. However, in some embodiments, coordinates on pupil plane 1415 may first be converted to a local pupil frame of reference before calculating the θ and φ angles and computing the corresponding total dioptric power. Indeed, in this case, the cylinder axis orientation may not be well-defined relative to the horizontal direction as defined by the display. The required local pupil frame of reference may be acquired from the pupil tracker or similar. For example, in one embodiment, a local pupil frame of reference may be computed by a vector going from a pupil center of one eye to the pupil center of the second eye, the vector going from the pupil center to the screen center, both provided for example by the pupil tracker, and an "up" vector (i.e. oriented from pupil center location 1417 towards the top center of the pupil) may be determined by doing the cross product between the two vectors. This conversion of coordinates into a local pupil frame of reference may also be applied without restriction to the methods of 1100, 1900, 2400, and 2700 or for any method described herein using non-parallel planes.

Figure 42C:
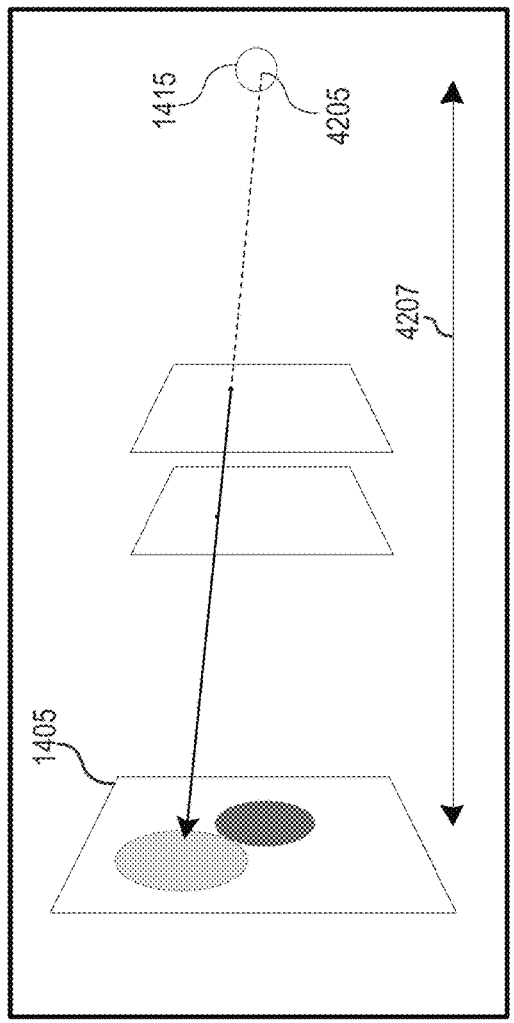
FIGS. 42A to 42C are schematic diagrams illustrating certain process steps of FIG. 41, in accordance with one embodiment.
Figure 42B:
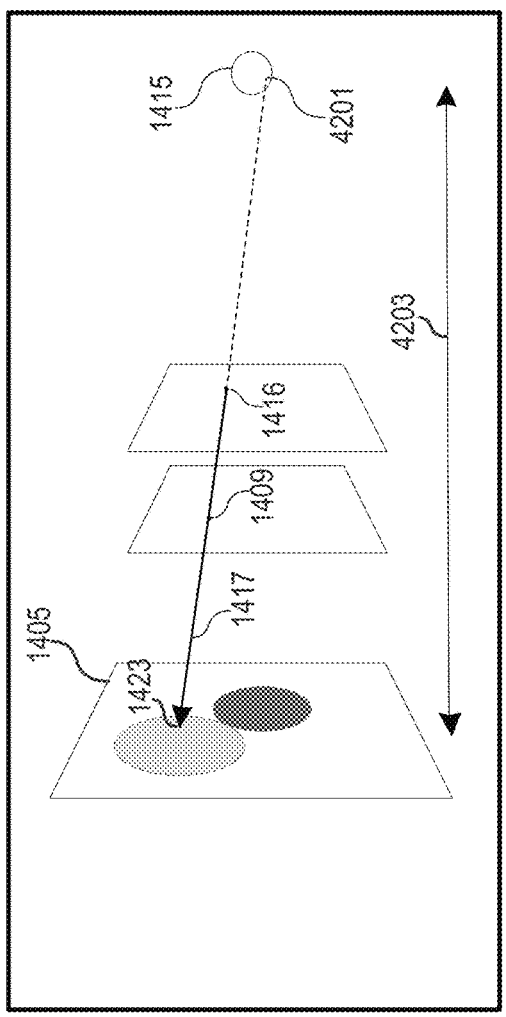
Figure 42A:
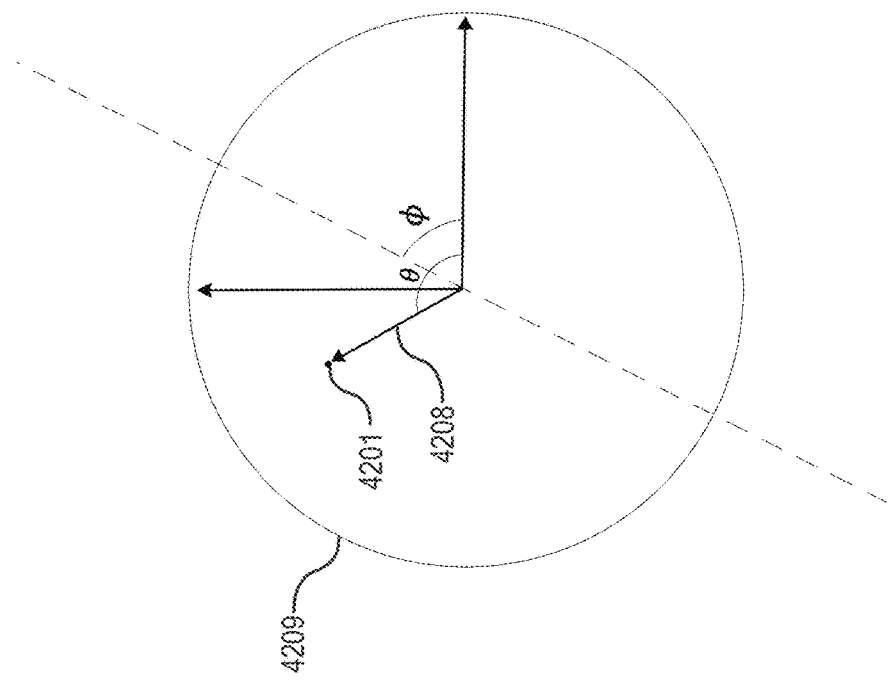

Once the total dioptric power has been computed, it may be converted into a corresponding virtual image plane location/depth for the current pixel chosen at step 1110. Therefore, each ray-tracing iteration, starting from step 1110, will have its "own" corresponding virtual image plane 1405 at a potentially different location, depending on the value of the total dioptric power computed above. This is schematically illustrated in FIGS. 42B and 42C, wherein two different intersection points, point 4201 in FIG. 42B and 4205 in FIG. 42C, each have a corresponding different virtual image plane depth or location (4203 vs 4207 respectively).

The corresponding virtual plane location may be derived in the same way as described above, for example for step 1106 of method 1100. In some embodiments, one may use the thin lens equation to derive this virtual plane location (i.e. find object distance that produces image on retina plane for the eye's focal length):

$$\frac{1}{\text{virt\_dist}} = P - \frac{1}{\text{eye\_depth}}$$

Wherein virt_dist is the virtual image plane location (for example depth 4203 or 4207, etc.), P is the total dioptric power discussed above which includes contributions from the spherical power 4001, cylindrical power 4005 and cylinder axis angle 4007 and wherein eye_depth is the variable eye depth 1314.

Next, step 1108 in method 4100 is applied to scale the image onto the designated virtual image plane similarly as described above for FIG. 11. In some embodiments, pupil plane 1415 may be off-axis and thus scaling the image may require additional treatment, such as described above with regard to FIGS. 39A to 39C.

Next, ray-tracing steps 1124, 1126 and 1128 proceed as described previously for method 1100 to compute the intersection point on the corresponding virtual image plane and the corresponding image pixel values to be applied.

In some embodiments, the astigmatism compensation technique applied to method 1100 to derive method 4100 may also be similarly used on method 1900. FIG. 53 shows a process flow diagram of method 5300, which is an exemplary ray-tracing rendering process for astigmatism compensation similar to method 1900. Thus, just like method 4100 mirrored method 1100, method 5300 mirrors method 1900 of FIG. 19.

In it, steps 1910 to 1920 and step 1922 are the same as in method 1900. However, instead of using a single location for eye focal plane 2006 for all pixels, a new location is computed at each iteration. Therefore, after step 1920, in the case where the ray vector 1425 does hit the pupil, method 5300 uses step 4101 described above for method 4100 to determine the total dioptric power comprising spherical and cylindrical contributions. Thus, the details regarding the determination of the total dioptric power described above are the same for method 5200 as for method 4100.

Once the total dioptric power has been calculated, in step S305, the location of eye focal plane 2006 corresponding to this total dioptric power value is determined. This may be done as described in method 1900 of FIG. 19.

For example, the location of eye focal plane 2006 derived from the total dioptric power computed at step 4101 may be done using the thin lens formula:

$$\text{focal\_dist} = 1 \Big/ \left( P - \frac{1}{\|\text{pupil\_pos} - \text{lens\_pos}\|} \right)$$

wherein focal_dist is the location of eye focal plane 2006 corresponding to P, the total dioptric power computed at step 4101, pupil_pos is the location of the pupil plane 1415 and lens_pos is the location of the of the optical layer 1403. Once the location of eye focal plane 2006 is known, steps 1921, 1923, 1925, 1927, 1929, 1931, 1934 and 1936 follow exactly as described for method 1900.

Figure 44A:
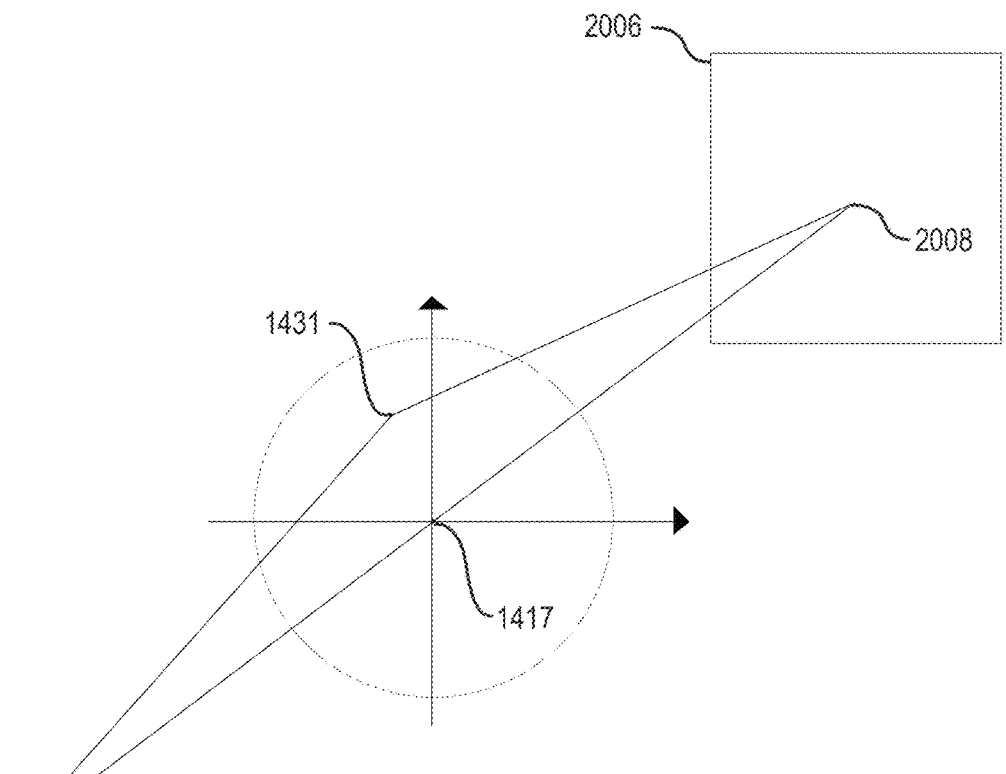
FIGS. 44A and 44B are schematic diagrams illustrating ray-tracing on the focus plane for spherical and cylindrical lens respectively, in accordance with one embodiment.
Figure 44B:
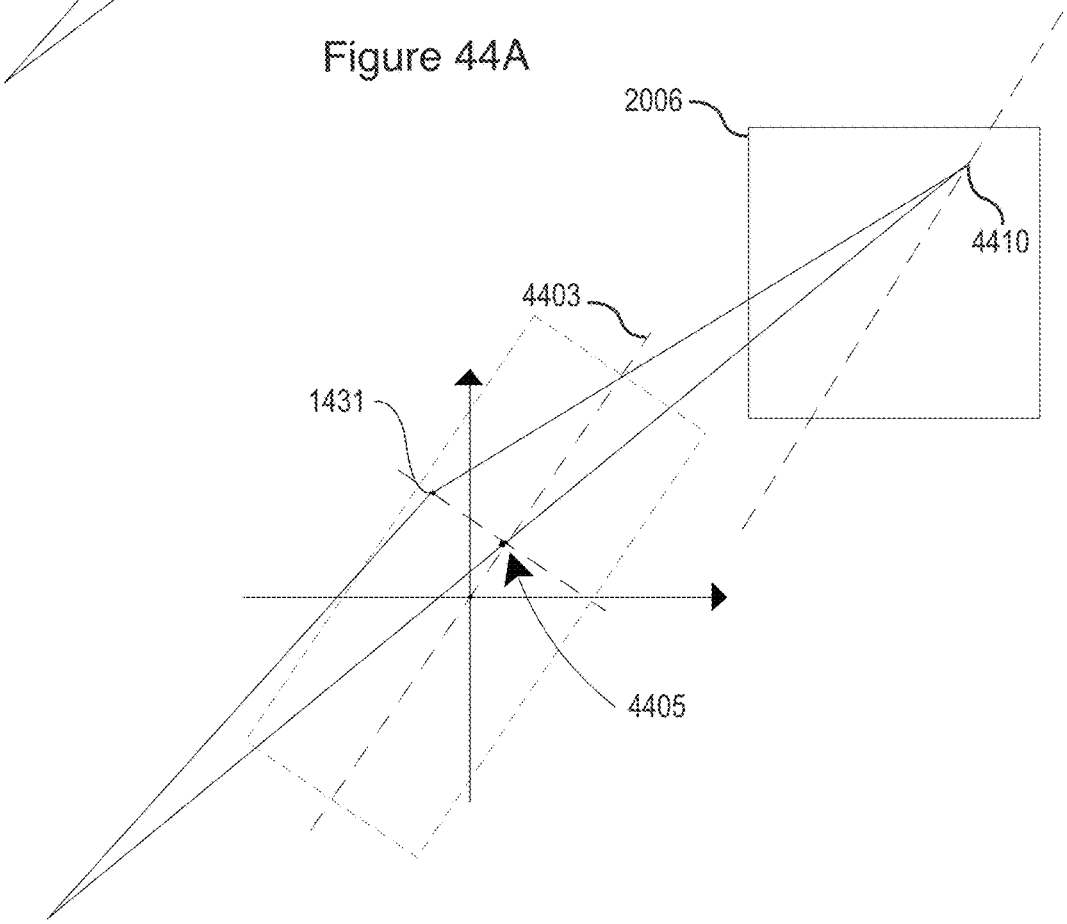

With reference to FIGS. 43 to 44C and in accordance with one exemplary embodiment, another ray-tracing rendering process for astigmatism compensation, generally referred to using the numeral 4300, will now be described.

Figure 46:
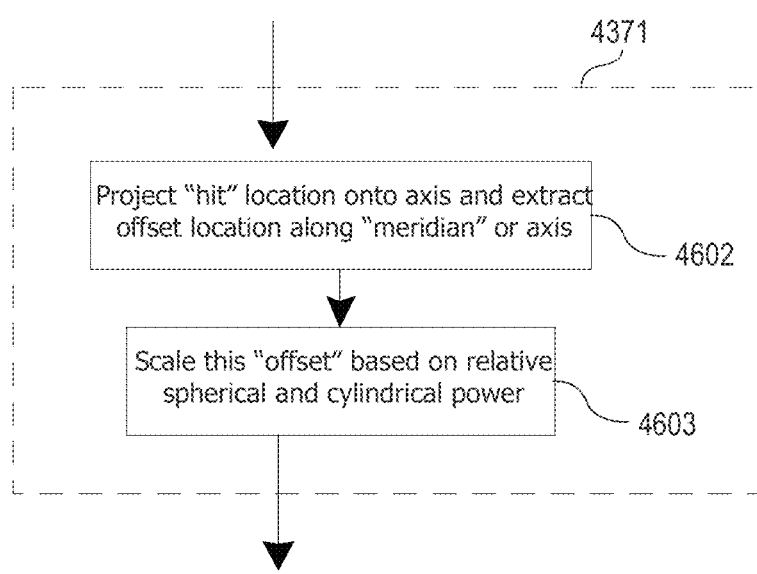
FIG. 46 is a process flow diagram illustrating a process step of FIG. 43, in accordance with one embodiment.

This method also follows closely the method of FIG. 19 (e.g. ray-tracing on the eye focal plane 2006) and is illustrated by the process flow chart of FIG. 43. As seen therein, this method comprises all of the steps of FIG. 19, but with a new step 4371 added between steps 1920 and 1921. This new step is further detailed in FIG. 46. This new step takes into account combined effects of spherical dioptric power 4001, cylindrical dioptric power 4005 and cylinder axis angle 4007 variables to derive a location for intersection point 2008 on focal plane 2006.

Indeed, when considering spherical dioptric power only, intersection point 2008 was computed by drawing a line through pupil center 1417, since for an ideal spherical lens, the ray going through the center will not be deviated by the refractive optics. This is illustrated schematically in FIG. 44A, which is a perspective view of the situation described previously in FIG. 20B. Then, as discussed above, it may be approximated that any other ray originating from the same pixel will converge on the same point on the focal plane 2006 (for example the ray going from intersection point 1431 on the pupil plane to point 2008 on focal plane 2006 in FIG. 20B). However, if instead of modelling the eye as a thin spherical lens but instead as a thin cylindrical lens, then in this case any ray originating from the same source or pixel along a meridian perpendicular to the cylinder axis of the cylindrical lens will converge on the same point 4410 on the focal plane 2006 along the main axis. This is illustrated schematically in FIG. 44B.

Thus, for the same intersection point 1431, the point needed for drawing the straight line will have a different location along the cylinder axis. The two points identified above (1417 for the spherical case and 4405 for the cylindrical case) may be taken as extreme cases (i.e. purely spherical and purely cylindrical). Thus, if we consider a hybrid case of where the eye acts like a sphero-cylindrical lens combining the effects of a spherical lens with a cylindrical lens, that point will lie somewhere in-between those two extremum points (1417 and 4405) on the cylinder axis. This is illustrated schematically in FIGS. 45A to 45C. For example, FIG. 45A shows rays being drawn through extremum points 1417 and 4405 and the region 4501 along the cylinder axis on pupil plane 1415 wherein a corresponding "offset" center pupil location is expected to be found. FIG. 45B shows a schematic diagram similar to the diagram of FIG. 42A where the same exemplary geometry is used, while FIG. 45C shows schematically an exemplary offset pupil center location 4515 and its corresponding coordinates on pupil plane 1415.

Thus, new step 4371 of method 4300 consists of locating offset pupil center location 4515 within this range 4501 along the cylinder axis corresponding to an input value of cylinder axis angle 4007 for the current pixel iteration started at step 1910. Step 4371 may itself be divided into of two steps, as illustrated in the flow diagram of FIG. 46. There we see that initially, at step 4602, that position vector 4201 of the intersection point location 1431 on pupil plane 1415 is projected onto the cylinder axis 4403 to obtain a position vector 4405 of extremum point 4505. For example, the x and y components of point 4405 along cylinder axis 4403 may be determined by computing:

$$E_x = d \cos(\theta - \phi)\cos(\phi)$$

$$E_y = d \cos(\theta - \phi)\sin(\phi)$$

wherein d is the length of the position vector 4201 on the retina, $\theta$ and $\phi$ are the angle of the position vector 4201 and the angle of the cylinder axis 4403, respectively.

Once vector 4505 along the cylinder axis giving the position of extremum point 4405 is known, at step 4603 we may scale the length of that vector as a function of the relative dioptric power of the spherical and cylindrical contributions required or desired. Different scaling functions may be used. For example, the scaling function $F_S$ may be of the type:

$$F_S = C/(C+S)$$

wherein C is the cylindrical dioptric power 4005 and S the spherical dioptric power 4001 we want to induce. This function tends to 0 when S>>C (i.e. eye=purely spherical lens), or to 1 if C>>S (eye=purely cylindrical lens).

Thus, offset pupil center location 4515 may then be computed as:

$$C_x = F_S d \cos(\theta - \phi)\cos(\phi)$$

$$C_y = F_S d \cos(\theta - \phi)\sin(\phi)$$

wherein ($C_x$, $C_y$) are the coordinates of offset pupil center 4515 in pupil plane 1415, $F_S$ is the scaling function defined above, $\theta$ the angle of the position vector 4201 and $\phi$ the angle of cylinder axis 4403, both defined with respect to the x axis in the pupil reference frame, as seen in FIGS. 45B and 45C. As discussed above, in the case where the head is tilted or at an angle with respect to the display, it may be necessary to use a local pupil reference system before and after step 2871.

Once offset pupil center location 4515 has been computed, steps 1921 and 1923 of method 4300 may proceed as described previously but by replacing pupil center location 1417 for offset pupil center location 4515 to compute the location of intersection point 2008 on focal plane 2006. However, step 1927 may proceed without using offset pupil center location 4515, as it is assumed that the pupil center 1417 is aligned with display center location 2018, thus no cylindrical compensation is needed.

All other steps in method 4300 mirror those of method 1900. Furthermore, in the case where cylindrical dioptric power 4005 is zero, method 4300 gives the same output as method 1900, as expected, since the equations shown above will give an offset pupil center location 4515 which is equal to pupil center position 1417. In some embodiments, methods 4100 and 4300 described above may also be adapted for projecting or displaying multiple images or optotypes simultaneously at different values of spherical dioptric power 4001, cylindrical dioptric power 4005 and cylinder axis angle 4007.

For example, a small modification to methods 4100, 5300 and 4300 which would allow for multiple simultaneous optotypes would be to define regions or portions of pixels within pixel display 1401 and assign to them a single optotype having a corresponding assigned set of input parameters (e.g. spherical dioptric power 4001, cylindrical dioptric power 4005 and cylinder axis angle 4007). Therefore, the set of parameters to the used would be known upon each iteration of step 1110 where a new pixel is chosen for ray-tracing. The method would fetch the corresponding set of vision correction parameters assigned to the pixel display portion comprising the chosen pixel and used them when upon reaching step 4101.

Figure 50A:
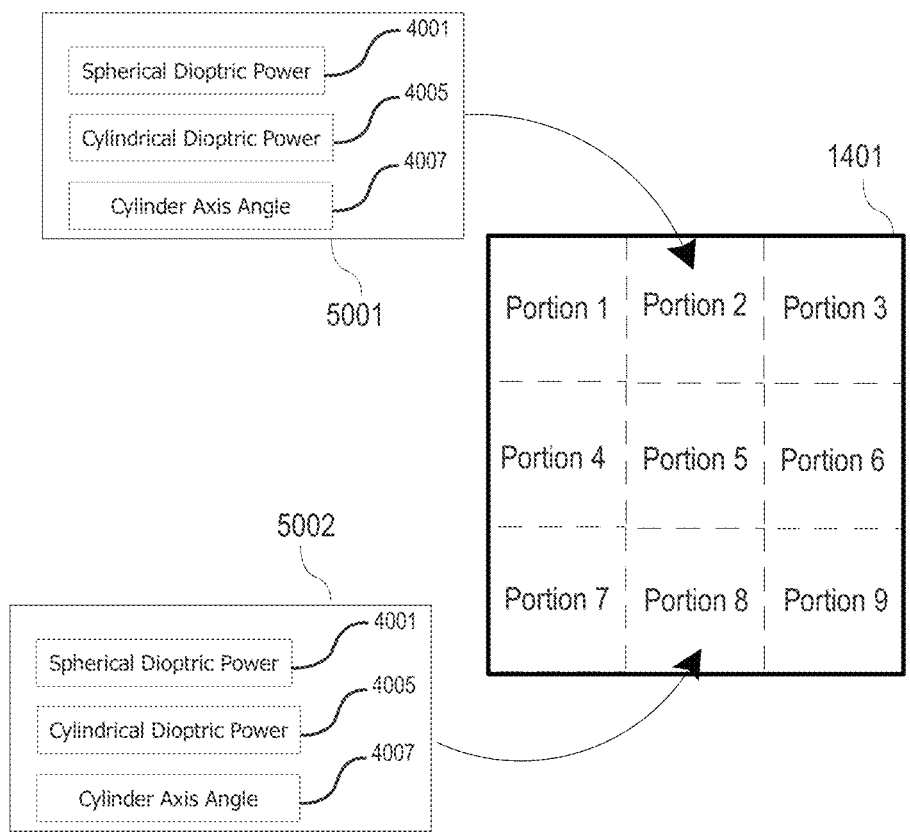
FIGS. 50A and 50B are schematic diagrams illustrating some modifications to the method of FIGS. 41 and 43 that allows for multiple optotypes to be displayed with different vision correction parameters, in accordance with one embodiment.
Figure 50B:
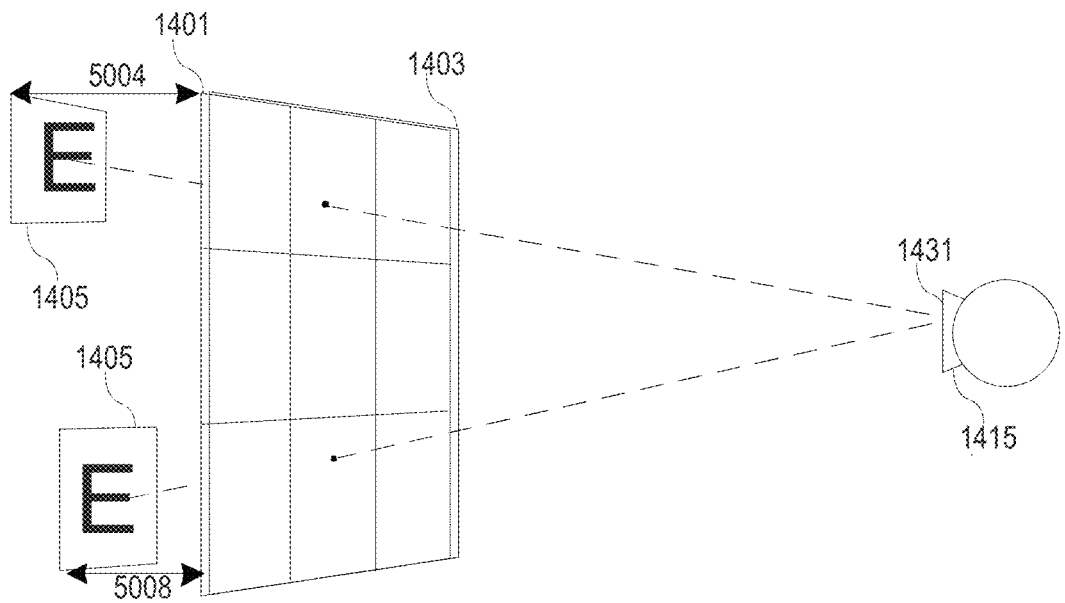

In an example using method 4100 and illustrated schematically in FIGS. 50A and 50B, the pixel display 1401 is divided into 9 cells/regions/portions, every pixel within a given portion being reserved for displaying a single image or optotype with a corresponding set of vision correction parameters. The skilled technician will understand that the division shown in FIGS. 50A and 50B is an example only and that any divisional configuration of pixel display 1401 may be used without limitation. Moreover, in the example of FIG. 50A, portions 2 and 7 are shown each having been assigned a distinct set of vision correction parameters 5001 and 5002. In FIG. 50B is shown two light rays originating from portions 2 and 9 having the same intersection point 1431 on pupil plane 1415, but wherein the distinct sets 5001 and 5002 result in each virtual image plane 1405 at a different distance or depth 5004 and 5008, respectively.

In some embodiments, the image or optotype assigned to a given pixel array portion may be made small enough and/or centered within said portion so to avoid any overlapping/cross-talk/occlusion between the light field generated from this pixel array portion with a light field emitted from a neighboring pixel array portion. For example, in the case of optotypes such as letters, these may be small and surrounded by transparent pixels or the like.

The same technique illustrated in FIG. 50A of assigning pixel display portions to or regions to pixel display 1401 may be used for method 4300 or method 5300 as well. In this case, the set of vision correction parameters corresponding to a given pixel display portion are fetched at step 1910 (in both cases) and used upon reaching step 4371 in method 4300 or step 4101 in method 5300.

Figure 51:
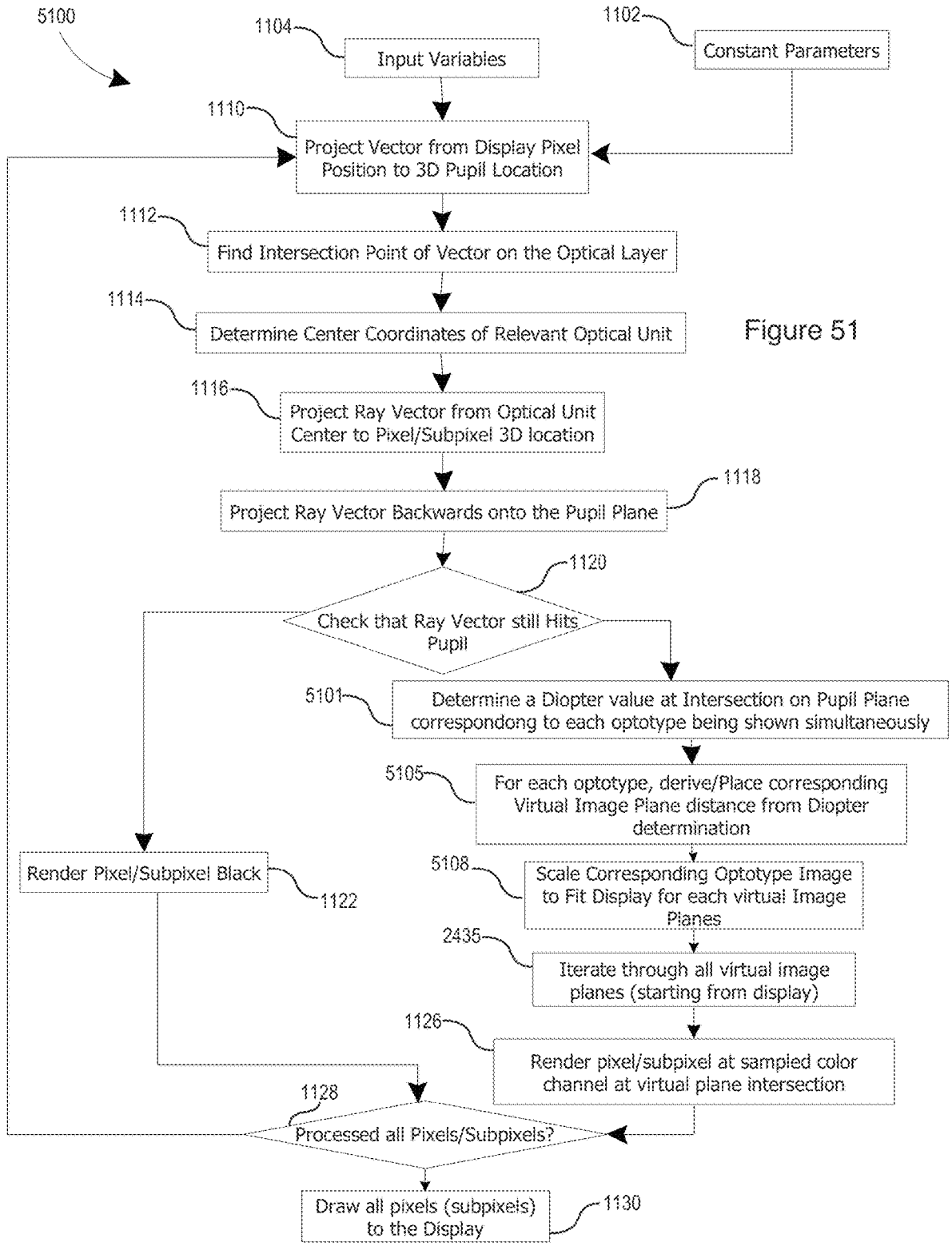
FIG. 51 is a process flow diagram of an illustrative ray-tracing rendering process for rendering a light field originating from multiple distinct virtual image planes in the context of astigmatism compensation, in accordance with one embodiment.
Figure 52:
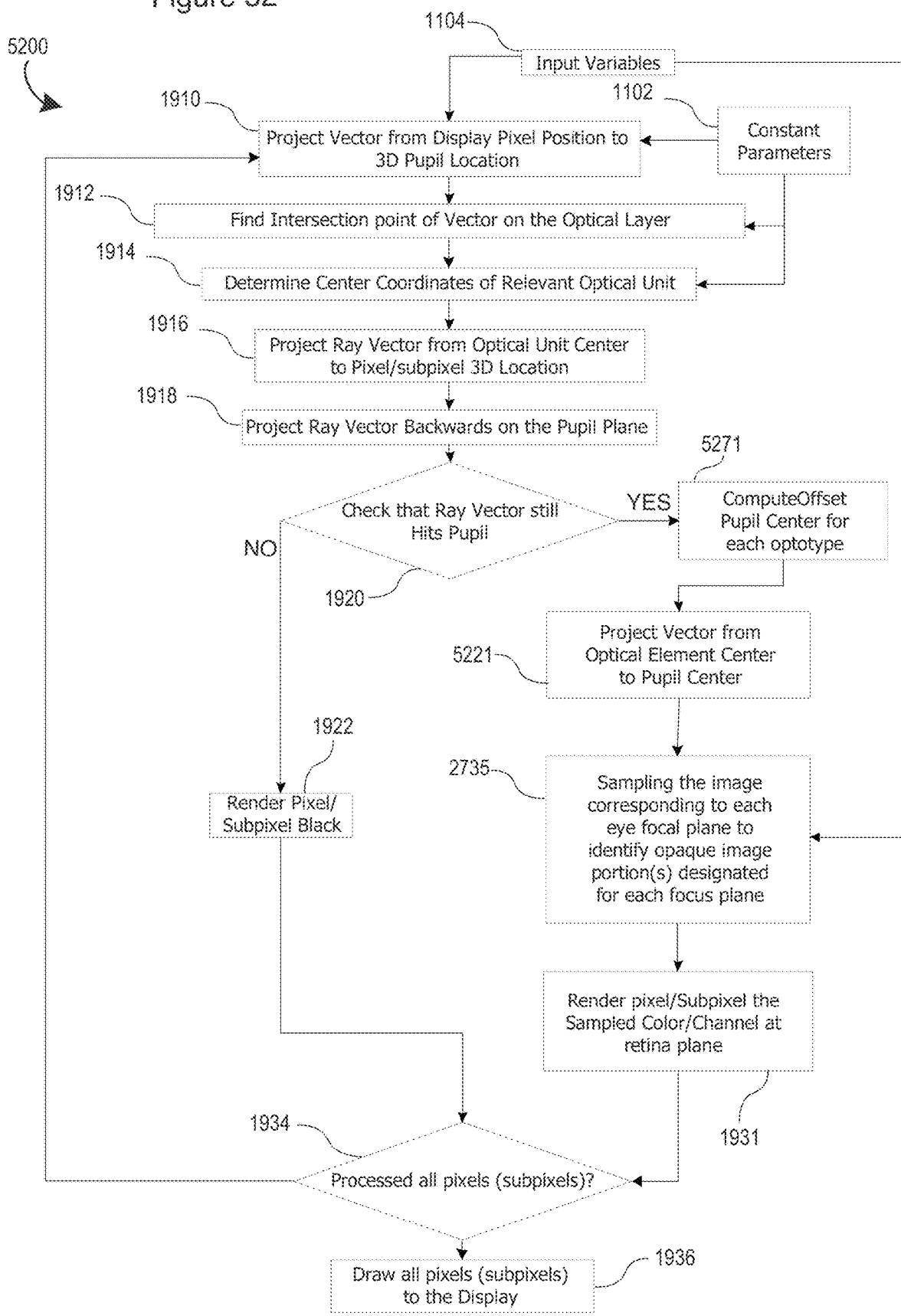
FIG. 52 is a process flow diagram of an illustrative ray-tracing rendering process for rendering a light field originating from multiple distinct eye lens image planes in the context of astigmatism compensation, in accordance with one embodiment.

With reference to FIGS. 51 and 52, and in accordance with one embodiment, other methods of displaying multiple optotypes at distinct image planes, but in the context of astigmatism compensation, will now be discussed. In some embodiments, methods 2400 and 2700 of FIGS. 24 and 27 may be adapted for astigmatism compensation in ways similar to how methods 1100 and 1900 were adapted into methods 4100 and 4300.

FIG. 51 shows a process flow diagram of method 5100, which is a version of method 2400 incorporating astigmatism compensation. As shown in FIG. 51, steps 1102 to 1122 proceed as described previously. Then, once intersection point 1431 is known, step S101 proceeds like in step 4101 described above. However, instead of using a single set of values of spherical dioptric power 4001, cylinder axis 4007 and cylindrical power 4005 to compute a total dioptric power value, at step S101 a set of different total dioptric power values are computed instead, each value corresponding to a different set of spherical dioptric power 4001, cylindrical power 4005, and cylinder axis 4007 corresponding to a different optotype being displayed. Thus, if N different optotypes are being displayed simultaneously, then N values of total dioptric powers are computed here corresponding to N different virtual image planes. Then, at step S105, in a manner similar to step 4105 of method 4100, each virtual image plane may be digitally placed or located at the distance or depth corresponding to different corresponding set of dioptric power values. At step S108 (similarly to step 2408) each optotype image may be scaled onto its corresponding virtual image plane as described above. Step 2435 then proceeds just as described in FIG. 25 by tracing back through each virtual image plane and identifying the closest non-transparent pixel value. Finally steps 1126 and 1128 proceed as described above.

Similarly, FIG. 52 shows a process flow diagram illustrating a similarly adapted version of method 2700 of FIG. 27 modified to account for astigmatism compensation, according to one embodiment. Once more, most of the steps follow method 2700 described above. However, similarly to new step 4371 in method 4300, step S271 is herein inserted after the pupil intersection 1431 has been computed for a given pixel (steps 1918 and 1920). Here a location of an offset pupil center 4505 is computed just as discussed above with regard to step 4371, but instead of computing a single offset pupil center location, multiple locations, each corresponding to different values of dioptric power 4001, cylindrical power 4005, and cylinder axis 4007 of a different optotype, are computed. Then, at step S221, similarly like in step 1921 of method 4300, a vector may be drawn through the offset pupil center location, but herein a different vector is drawn for each one of the offset pupil center locations computed at the previous step. Thus, if N optotypes are shown simultaneously, each image having its own set of parameters, then N offset pupil center location may be derived therefrom, each defining a different intersection point on its respective eye focal plane at step 1923 of step 2735 (i.e. each focal plane at step 2805 will have its own associated vector to find intersection point 2008). From this, the rest of method 5200 follows method 2700 normally.

In some embodiments, assuming that all optotypes use the same spherical dioptric power 4001 but different values of cylindrical dioptric power 4005 and cylinder axis angle 4007, a first ray-tracing iteration using an initial value of spherical dioptric power 4001 may be used, but with cylindrical dioptric power 4005 first set to zero.

As an example, in method 4100, a first iteration using only spherical dioptric power 4001 may be executed until the intersection point 1423 on virtual image plane 1405 is computed and the corresponding pixel image value is identified at step 1126 (but not rendered). Then, the optotype or image associated with this pixel image value is identified and the corresponding cylindrical dioptric power 4005 and cylinder axis angle 4007 values for this optotype is kept in memory. However, the pixel image value is not used yet. Instead, the method starts over from step 4101 (point on pupil), but now uses the values 4005 and 4007 to compute a new value for the total dioptric power. This new value is then converted as described above into a new position of virtual image plane 1405. The ray is traced back to the new position and the corresponding pixel image value is again computed. A check is made that the pixel value corresponds to the same optotype or image identified in the first iteration. If it is the case, then the method may move to the next pixel in pixel array 1401.

In the case where the second iteration finds that the optotype (on the virtual image plane) has changed, then the values 4005 and 4007 for that new optotype is used and a new iteration is made. Another check is made that the same optotype is again intersected.

In the case of transparent pixels, in some embodiments these may be assigned to the optotype or image closest to them. Thus, if at the first iteration a transparent pixel is In some cases, the two-iteration method described above may result in a large jump in dioptric power. In some embodiments, instead of doing two iterations as described above (a first iteration using only spherical dioptric power 4001 and a second adding the contribution from cylindrical dioptric power 4005 and cylinder axis angle 4007), the second iteration may itself be broken up into multiple iterations (i.e. akin to an numerical optimization procedure). For example, after the first iteration using only spherical dioptric power is done, instead of assigning the full value of cylindrical dioptric power 4005 and cylinder axis angle 4007 for the second iteration, only a small increment is made to these parameters. If the second iteration intersects with the same optotype, then a third iteration is made again increasing the 4005 and 4007 by a small value. Again, if at any iteration a different optotype is intersected, then the following iteration will see the cylindrical parameters incremented towards the end values of this new optotype. The iterations are repeating until convergence for this given pixel in pixel array 1401 (i.e. the final desired values of 4005 and 4007 are used and the right optotype is intersected). Then a new series of iterations is started for the next pixel.

Similarly, in some embodiments, the same procedure may be applied to method 4300, but wherein a shift in offset pupil center position 4515 is incremented stepwise or iteratively as a function of the optotype on eye focal plane 2006.

Accordingly, it can be observed that the ray-tracing methods 2400 and 2700 noted above, any modification thereto also discussed above, and related light field display solutions, can be equally applied to image perception adjustment solutions for visual media consumption, as they can for subjective vision testing solutions, or other technologically related fields of endeavour. As alluded to above, the light field display and rendering/ray-tracing methods discussed above may all be used to implement, according to various embodiments, a subjective vision testing device or system such as a phoropter or refractor. Indeed, a light field display may replace, at least in part, the various refractive optical components usually present in such a device. Thus, the vision correction light field ray tracing methods 1100, 1900, 2400, 2700, 4100, 4300, 5100, 5200 or 5300 discussed above may equally be applied to render optotypes at different dioptric power or refractive correction by generating vision correction for hyperopia (far-sightedness) and myopia (nearsightedness), as was described above in the general case of a vision correction display. Light field systems and methods described herein, according to some embodiments, may be applied to create the same capabilities as a traditional instrument and to open a spectrum of new features, all while improving upon many other operating aspects of the device. For example, the digital nature of the light field display enables continuous changes in dioptric power compared to the discrete change caused by switching or changing a lens or similar; displaying two or more different dioptric corrections seamlessly at the same time; and, in some embodiments, the possibility of measuring higher-order aberrations and/or to simulate them for different purposes such as, deciding for free-form lenses, cataract surgery operation protocols, IOL choice, etc.

With reference to FIGS. 30, and 31A to 31C, and in accordance with different embodiments, an exemplary subjective vision testing system, generally referred to using the numeral 3000, will now be described. At the heart of this system is a light field vision testing device such as a light field refractor or phoropter 3001. Generally, the light field phoropter 3001 is a device comprising, at least in part, a light field display 3003 and which is operable to display or generate one or more optotypes to a patient having his/her vision acuity (e.g. refractive error) tested. In some embodiments, the light field phoropter may comprise an eye tracker 3009 (such as a near-IR camera or other as discussed above) that may be used to determine the pupil center position in real-time or near real-time, for accurately locating the patient's pupil, as explained above with regard to the ray-tracing methods 1100, 1900, 2400, 2700, 4100, 4300, 5100, or 5300. Indeed, FIG. 32 shows a plot of the angular resolution (in arcminutes) of an exemplary light field display comprising a 1500 ppi digital pixel display as a function of the dioptric power of the light field image (in diopters). We clearly see that, in this particular example, the light field display is able to generate displacements (line 3205) in diopters that have higher resolution corresponding to 20/20 vision (line 3207) or better (e.g. 20/15—line 3209) and close to (20/10—line 3211)), here within a dioptric power range of 2 to 2.5 diopters. Thus, the light field displays and ray-tracing methods described above, according to different embodiments, may be used to replace, at least in part, traditional optical components. In some embodiments, a head-rest, eyepiece or similar (not shown) may be used to keep the patient's head still and in the same location, thus in such examples, foregoing the general utility of a pupil tracker or similar techniques by substantially fixing a pupil location relative to this headrest. In some embodiments, phoropter 3001 may comprise a network interface 3023 for communicating via network to a remote database or server 3059.

Figure 31A:
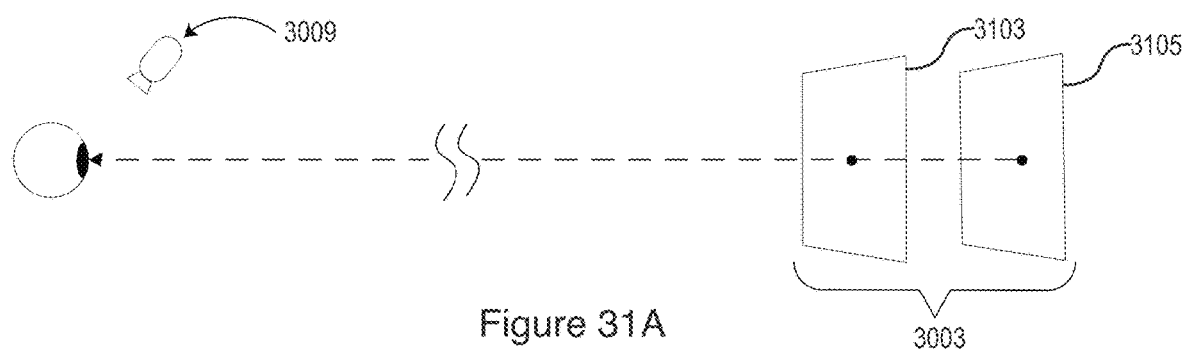
FIGS. 31A to 31C are schematic diagrams of exemplary light field refractors/phoropters, in accordance with different embodiments.
Figure 32:
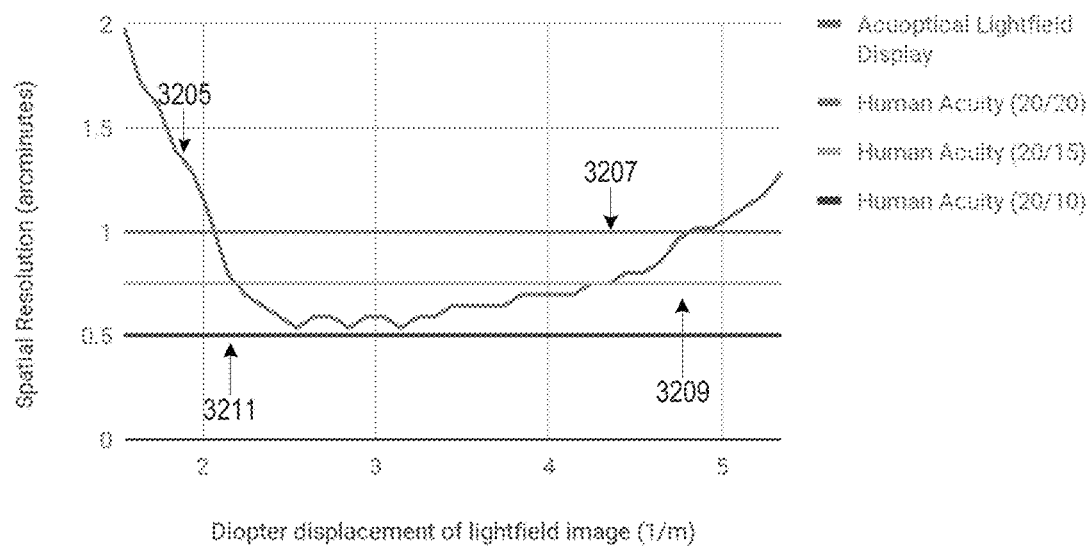
FIG. 32 is a plot of the angular resolution of an exemplary light field display as a function of the dioptric power generated, in accordance with one embodiment.

For example, in one embodiment and as illustrated in FIG. 31A, the light field phoropter 3001 may comprise light field display 3003 (herein comprising a MLA 3103 and a digital pixel display 3105) located relatively far away (e.g. one or more meters) from the patient's eye currently being diagnosed. Note that the pointed line is used to schematically illustrate the direction of the light rays emitted by the display 3105. Also illustrated is the eye-tracker 3009, which may be provided as a physically separate element, for example, installed in at a given location in a room or similar. In some embodiments, the noted eye/pupil tracker may include the projection of IR markers/patterns to help align the patient's eye with the light field display. In some embodiments, a tolerance window (e.g. "eye box") may be considered to limit the need to refresh the ray-tracing iteration. An exemplary value of the size of the eye box, in some embodiments, is around 6 mm, though smaller (e.g. 4 mm) or larger eye boxes may alternatively be set to impact image quality, stability or like operational parameters.

Going back to FIG. 30, light field phoropter 3001 may also comprise, according to different embodiments and as will be further discussed below, one or more refractive optical components 3007, a processing unit 3021, a data storage unit or internal memory 3013, a network interface 3023, one or more cameras 3017 and a power module 3023.

In some embodiments, power module 3023 may comprise, for example, a rechargeable Li-ion battery or similar. In some embodiments, it may comprise an additional external power source, such as, for example, a USB-C external power supply. It may also comprise a visual indicator (screen or display) for communicating the device's power status, for example whether the device is on/off or recharging.

In some embodiments, internal memory 3013 may be any form of electronic storage, including a disk drive, optical drive, read-only memory, random-access memory, or flash memory, to name a few examples. In some embodiments, a library of chart patterns (Snellen charts, prescribed optotypes, forms, patterns, or other) may be located in internal memory 3013 and/or retrievable from remote server 3059.

Figure 33A:
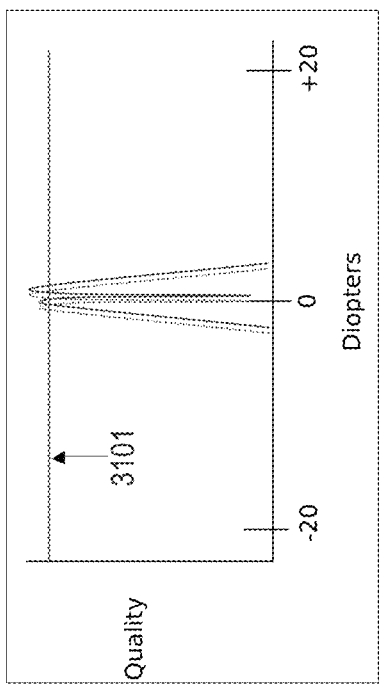
FIGS. 33A to 33D are schematic plots of the image quality generated by a light field refractor/phoropter as a function of the dioptric power generated by using in combination with the light field display (A) no refractive component, (B) one refractive component, (C) and (D) a multiplicity of refractive components.
Figure 33B:
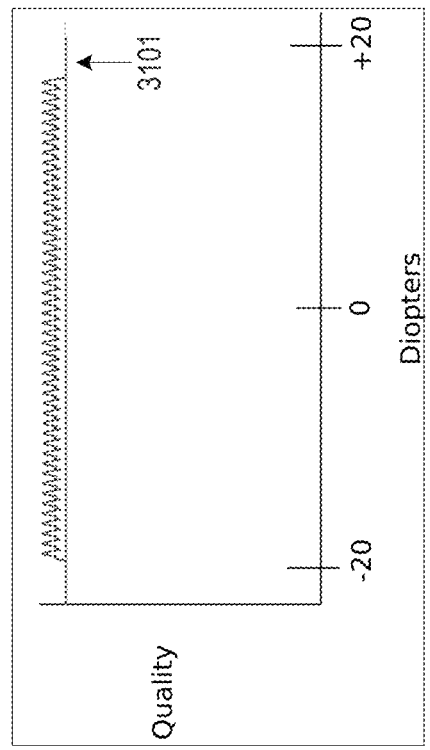

In some embodiments, one or more optical components 3007 can be used in combination with the light field display 3003, for example to shorten the device's dimensions and still offer an acceptable range in dioptric power. The general principle is schematically illustrated in the plots of FIGS. 33A to 33D. In these plots, the image quality (e.g. inverse of the angular resolution, higher is better) at which optotypes are small enough to be useful for vision testing in this plot is above horizontal line 3101 which represents typical 20/20 vision. FIG. 33A shows the plot for the light field display only, where we see the characteristic two peaks corresponding to the smallest resolvable point, one of which was plotted in FIG. 32 (here inverted and shown as a peak instead of a basin), and where each region above the line may cover a few diopters of dioptric power, according to some embodiments. While the dioptric range may, in some embodiments, be more limited than needed when relying only on the light field display, it is possible to shift this interval by adding one or more refractive optical components. This is shown in FIG. 33B where the regions above the line 3101 is shifted to the left (negative diopters) by adding a single lens in the optical path.

Figure 33C:
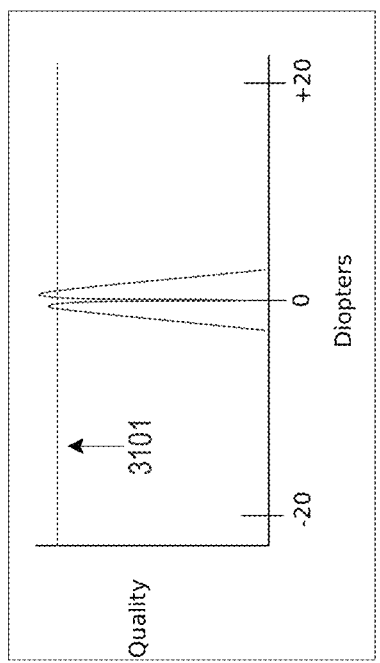
Figure 33D:
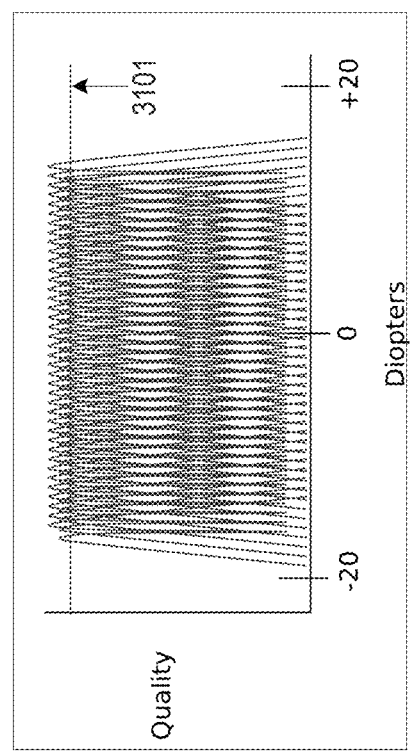

Thus, by using a multiplicity of refractive optical components or by alternating sequentially between different refractive components of increasing or decreasing dioptric power, it is possible to shift the center of the light field diopter range to any required value, as shown in FIG. 33C, and thus the image quality may be kept above line 3101 for any required dioptric power as shown in FIG. 33D. In some embodiments, a range of 30 diopters from +10 to −20 may be covered for example. In the case of one or more reels of lenses, the lens may be switched for a given larger dioptric power increment, and the light field display would be used to provide a finer continuous change to accurately pin-point the required total dioptric power required to compensate for the patient's reduced visual acuity. This would still result in light field phoropter 3001 having a reduced number of refractive optical components compared to the number of components needed in a traditional phoropter, while drastically enhancing the overall fine-tuning ability of the device.

Figure 31B:
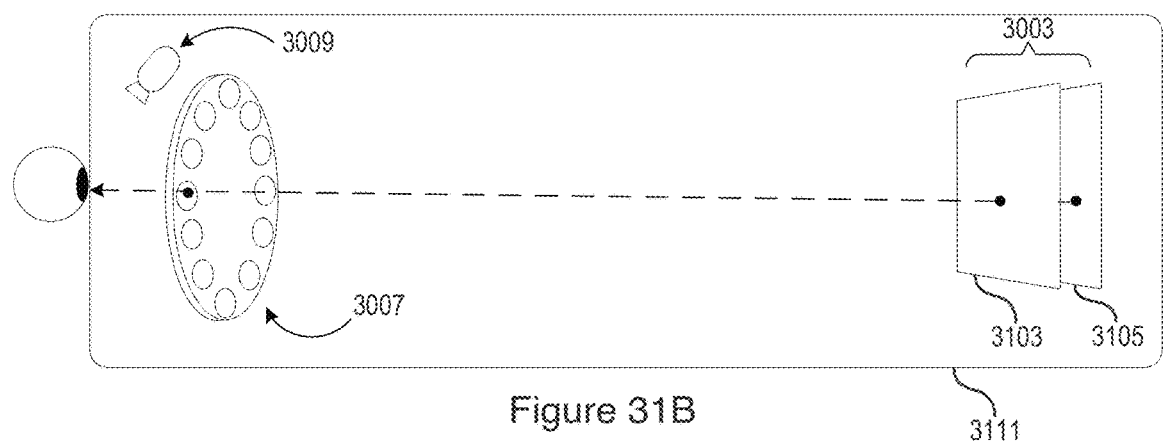

One example, according to one embodiment, of such a light field phoropter 3001 is schematically illustrated in FIG. 31B, wherein the light field display 3003 (herein shown again comprising MLA 3103 and digital pixel display 3105) is combined with a multiplicity of refractive components 3007 (herein illustrate as a reel of lenses as an example only). By changing the refractive component used in combination with the light field display, a larger dioptric range may be covered. This may also provide means to reduce the device's dimension, making it in some embodiments more portable, and encompass all its internal components into a shell, housing or casing 3111. In some embodiments, the light field phoropter may comprise a durable ABS housing and may be shock and harsh-environment resistant. In some embodiments, the light field phoropter 3001 may comprise a telescopic feel for fixed or portable usage; optional mounting brackets, and/or a carrying case. In some embodiments, all components may be internally protected and sealed from the elements.

In some embodiments, the casing may further comprise an eye piece or similar that the patient has to look through, which may limit movement of the patient's eye during diagnostic and/or indirectly provide a pupil location to the light field renderer.

Figure 31C:
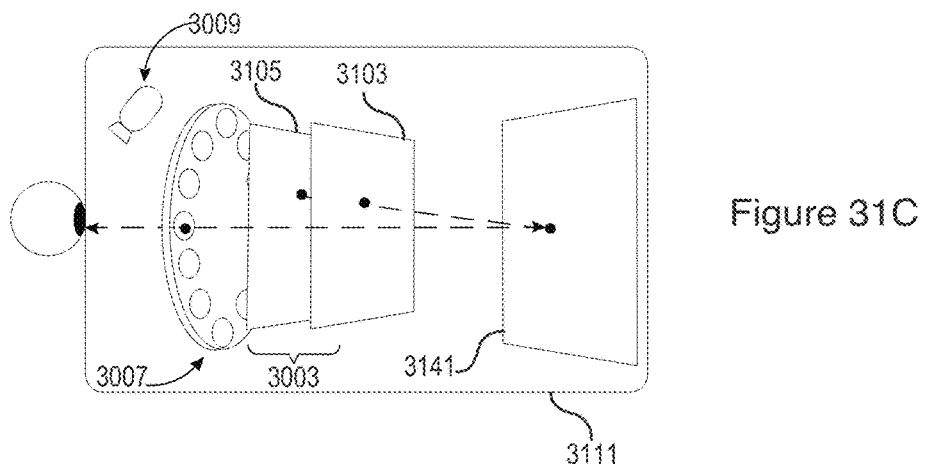

In some embodiments, it may also be possible to further reduce the size of the device by adding, for example, a mirror or any device which may increase the optical path. This is illustrated in FIG. 31C where the length of the device was reduced by adding a mirror 3141. This is shown schematically by the pointed arrow which illustrates the light being emitted from pixel display 3105 travelling through MLA 3103 before being reflected by mirror 3141 back through refractive components 3007 and ultimately hitting the eye.

The skilled technician will understand that different examples of refractive components 3007 may include, without limitation, one or more lenses, sometimes arranged in order of increasing dioptric power in one or more reels of lenses similar to what is typically found in traditional phoropters; an electrically controlled fluid lens; active Fresnel lens; and/or Spatial Light Modulators (SLM). In some embodiments, additional motors and/or actuators may be used to operate refractive components 3007. These may be communicatively linked to processing unit 3021 and power module 3023, and operate seamlessly with light display 3003 to provide the required dioptric power.

Figure 34A:
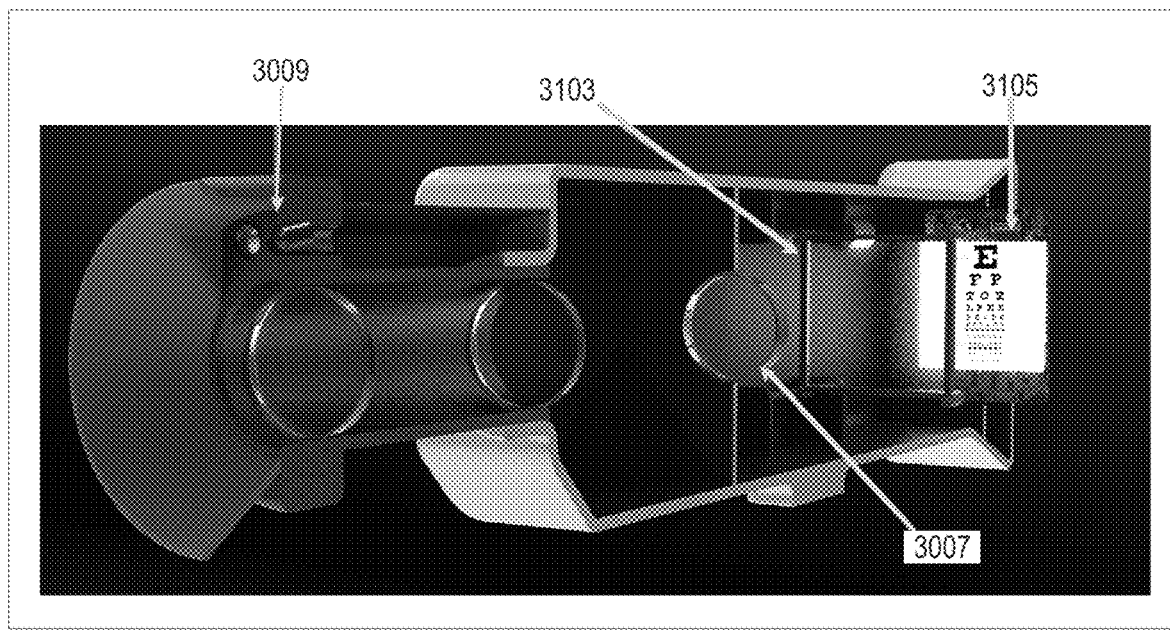
FIGS. 34A and 34B are perspective internal views of exemplary light field refractors/phoropters showing a casing thereof in cross-section, in accordance with one embodiment.
Figure 34B:
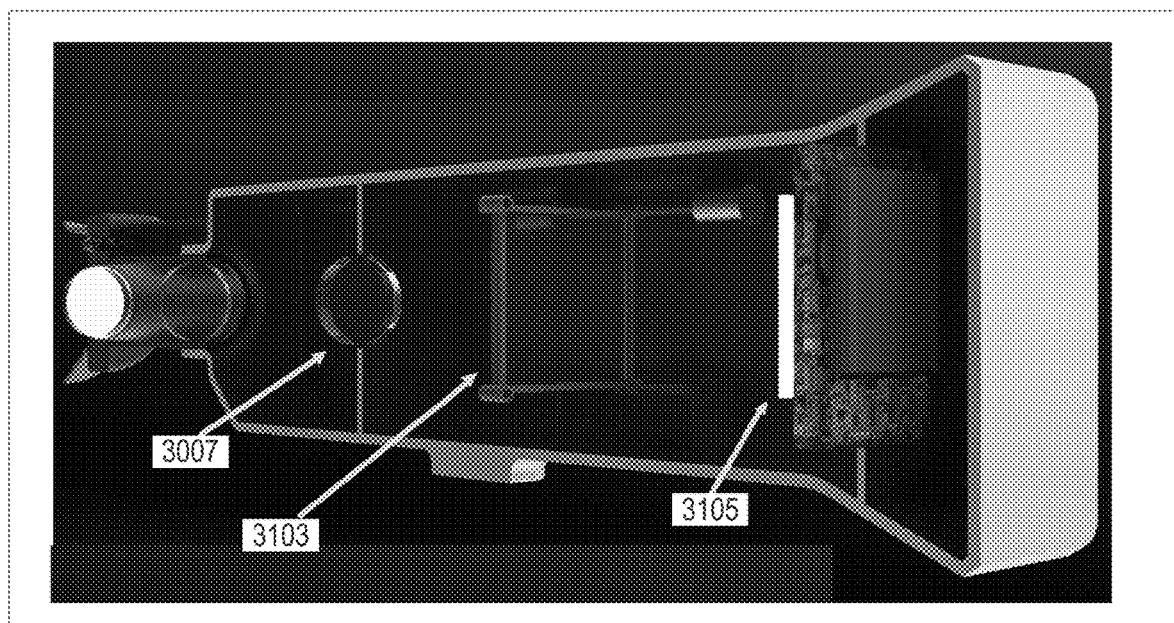

For example, FIGS. 34A and 34B show a perspective view of an exemplary light field phoropter 3001 similar to the one of FIG. 31B, but wherein the refractive component 3007 is an electrically tunable liquid lens. Thus, in this particular embodiment, no mechanical or moving component are used, which may result in the device being more robust. In some embodiments, the electrically tunable lens may have a range of ±13 diopters.

In one illustrative embodiment, a 1000 dpi display is used with a MLA having a 65 mm focal distance and 1000 μm pitch with the user's eye located at a distance of about 26 cm. A similar embodiment uses the same MLA and user distance with a 3000 dpi display.

Other displays having resolutions including 750 dpi, 1000 dpi, 1500 dpi and 3000 dpi were also tested or used, as were MLAs with a focal distance and pitch of 65 mm and 1000 μm, 43 mm and 525 μm, 65 mm and 590 μm, 60 mm and 425 μm, 30 mm and 220 μm, and 60 mm and 425 μm, respectively, and user distances of 26 cm, 45 cm or 65 cm.

Figure 30:
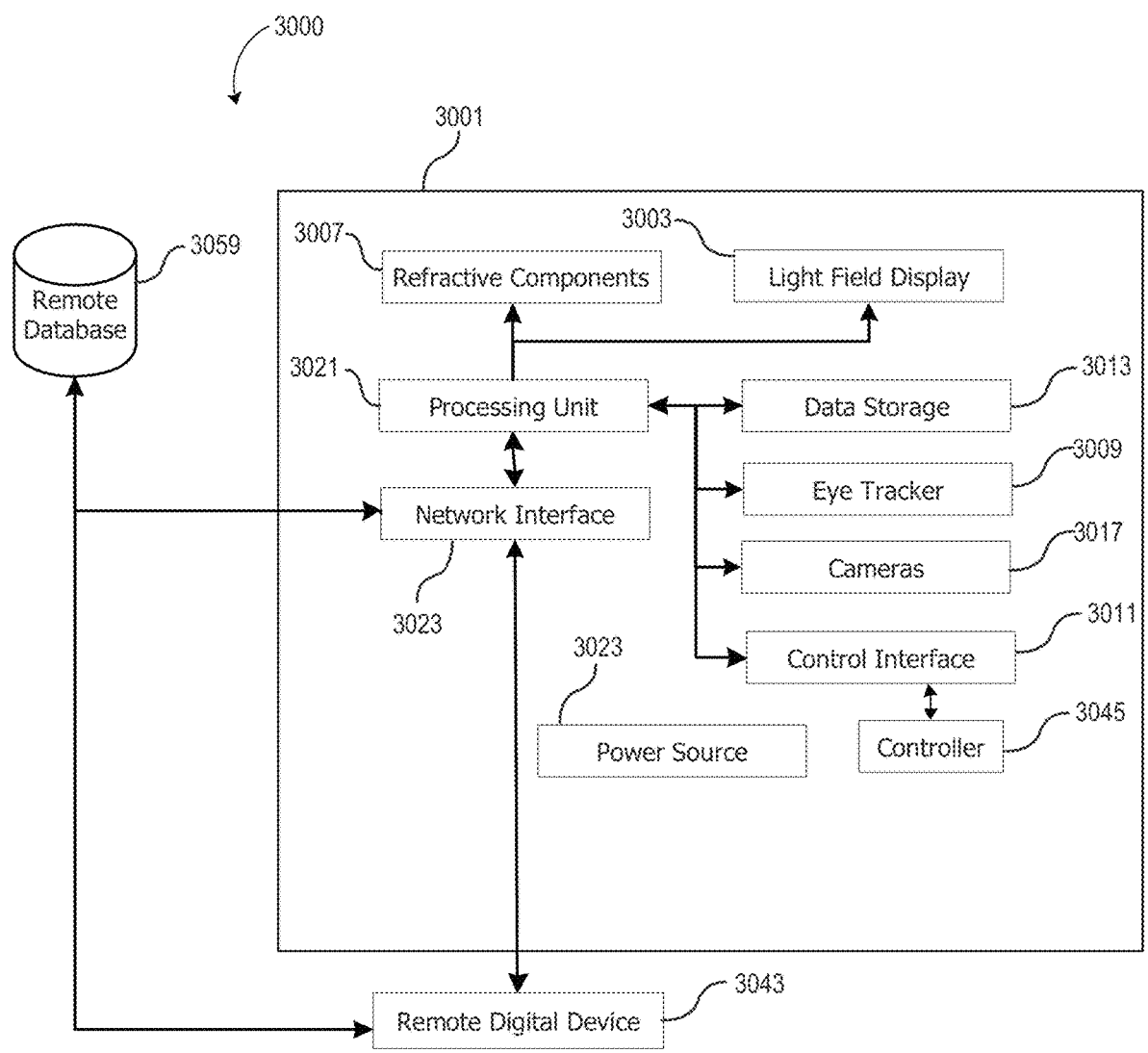
FIG. 30 is a schematic diagram of an exemplary vision testing system, in accordance with one embodiment.

Going back to FIG. 30, in some embodiments, eye-tracker 3009 may be a digital camera, in which case it may be used to further acquire images of the patient's eye to provide further diagnostics, such as pupillary reflexes and responses during testing for example. In other embodiments, one or more additional cameras 3017 may be used to acquire these images instead. In some embodiments, light field phoropter 3001 may comprise built-in stereoscopic tracking cameras.

In some embodiments, feedback and/or control of the vision test being administered may be given via a control interface 3011. In some embodiments, the control interface 3011 may comprise a dedicated handheld controller-like device 3045. This controller 3045 may be connected via a cable or wirelessly, and may be used by the patient directly and/or by an operator like an eye professional. In some embodiments, both the patient and operator may have their own dedicated controller. In some embodiments, the controller may comprise digital buttons, analog thumbstick, dials, touch screens, and/or triggers.

In some embodiments, control interface 3011 may comprise a digital screen or touch screen, either on the phoropter device itself or on an external module. In other embodiments, the control interface may let other remote devices control the light field phoropter via the network interface. For example, remote digital device 3043 may be connected to light field phoropter by a cable (e.g. USB cable, etc.) or wirelessly (e.g. via Bluetooth or similar) and interface with the light field phoropter via a dedicated application, software or website. Such a dedicated application may comprise a graphical user interface (GUI), and may also be communicatively linked to remote database 3059.

In some embodiments, the patient may give feedback verbally and the operator may control the vision test as a function of that verbal feedback. In some embodiments, phoropter 3001 may comprise a microphone to record the patient's verbal communications, either to communicate them to a remote operator via network interface 3023 or to directly interact with the device (e.g. via speech recognition or similar).

In some embodiments, processing unit 3021 may be communicatively connected to data storage 3013, eye tracker 3009, light field display 3003 and refractive components 3007. Processing unit 3021 may be responsible for rendering one or more optotypes via light field display 3003 and, in some embodiments, jointly control refractive components 3007 to achieve a required total dioptric power. It may also be operable to send and receive data to internal memory 3013 or to/from remote database 3059.

In some embodiments, diagnostic data may be automatically transmitted/communicated to remote database 3059 or remote digital device 3043 via network interface 3023 through the use of a wired or wireless network connection. The skilled artisan will understand that different means of connecting electronic devices may be considered herein, such as, but not limited to, Wi-Fi, Bluetooth, NFC, Cellular, 2G, 3G, 4G, 5G or similar. In some embodiments, the connection may be made via a connector cable (e.g. USB including microUSB, USB-C, Lightning connector, etc.). In some embodiments, remote digital device 3043 may be located in a different room, building or city.

Figure 35:
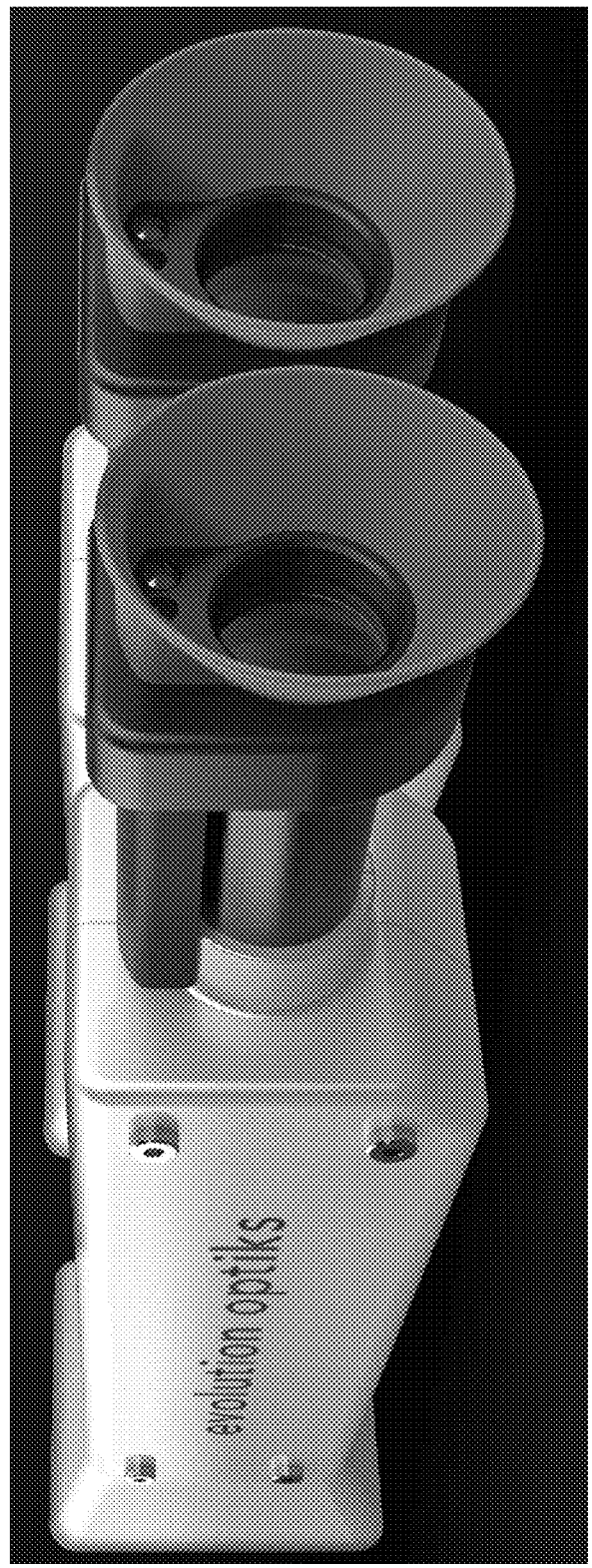
FIG. 35 is a perspective view of an exemplary light field refractor/phoropter combining side-by-side two of the units shown in FIGS. 34A and 34B for evaluating both eyes at the same time, in accordance with one embodiment.

In some embodiments, two light field phoropters 3001 may be combined side-by-side to independently measure the visual acuity of both left and right eye at the same time. An example is shown in FIG. 35, where two units corresponding to the embodiment of FIGS. 34A and 34B (used as an example only) are placed side-by-side or fused into a single device.

In some embodiments, a dedicated application, software or website may provide integration with third party patient data software. In some embodiments, the phoropter's software may be updated on-the-fly via a network connection and/or be integrated with the patient's smartphone app for updates and reminders.

In some embodiments, the dedicated application, software or website may further provide a remote, real-time collaboration platform between the eye professional and patient, and/or between different eye professionals. This may include interaction between different participants via video chat, audio chat, text messages, etc.

In some embodiments, light field phoropter 3001 may be self-operated or operated by an optometrist, ophthalmologist or other certified eye-care professional. For example, in some embodiments, a patient could use phoropter 3001 in the comfort of his/her own home.

Figure 36:
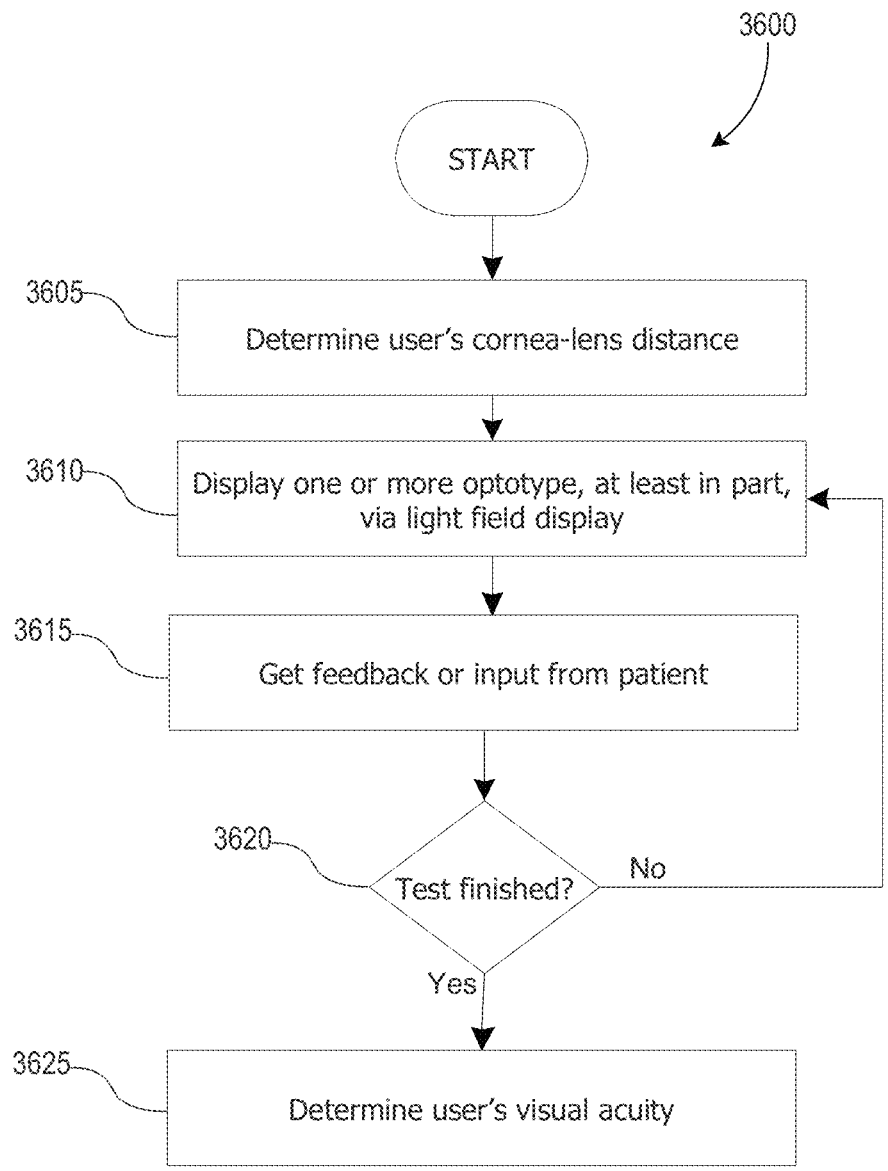
FIG. 36 is a process flow diagram of an exemplary dynamic subjective vision testing method, in accordance with one embodiment.

With reference to FIG. 36 and in accordance with different exemplary embodiments, a dynamic subjective vision testing method using vision testing system 3000, generally referred to using the numeral 3600, will now be described. As mentioned above, the use of a light field display enables phoropter 3001 of vision testing system 3000 to provide more dynamic and/or more modular vision tests than what is generally possible with traditional phoropters. Generally, method 3600 seeks to diagnose a patient's reduced visual acuity and produce therefrom, in some embodiments, an eye prescription or similar.

In some embodiments, eye prescription information may include, for each eye, one or more of: distant spherical, cylindrical and/or axis values, and/or a near (spherical) addition value.

In some embodiments, the eye prescription information may also include the date of the eye exam and the name of the eye professional that performed the eye exam. In some embodiments, the eye prescription information may also comprise a set of vision correction parameter(s) 201 used to operate any vision correction light field displays using the systems and methods described above. In some embodiments, the eye prescription may be tied to a patient profile or similar, which may contain additional patient information such as a name, address or similar. The patient profile may also contain additional medical information about the user. All information or data (i.e. set of vision correction parameter(s) 201, user profile data, etc.) may be kept on remote database 3059. Similarly, in some embodiments, the user's current vision correction parameter(s) may be actively stored and accessed from external database 3059 operated within the context of a server-based vision correction subscription system or the like, and/or unlocked for local access via the client application post user authentication with the server-based system.

Phoropter 3001 being, in some embodiments, portable, a large range of environment may be chosen to deliver the vision test (home, eye practitioner's office, etc.). At the start, the patient's eye may be placed at the required location. This is usually by placing his/her head on a headrest or by placing the objective (eyepiece) on the eye to be diagnosed. As mentioned above, the vision test may be self-administered or partially self-administered by the patient. For example, the operator (e.g. eye professional or other) may have control over the type of test being delivered, and/or be the person who generates or helps generate therefrom an eye prescription, while the patient may enter inputs dynamically during the test (e.g. by choosing or selecting an optotype, etc.).

As discussed above, the light field rendering method 3600 generally requires an accurate location of the patient's pupil center. Thus, at step 3605, such a location is acquired. In some embodiments, such a pupil location may be acquired via eye tracker 3009, either once, at intervals, or continuously. In other embodiments, the location may be derived from the device or system's dimension. For example, in some embodiments, the use an eye-piece or similar provides an indirect means of deriving the pupil location. In some embodiments, the phoropter 3001 may be self-calibrating and not require any additional external configuration or manipulation from the patient or the practitioner before being operable to start a vision test.

At step 3610, one or more optotypes is/are displayed to the patient, at one or more dioptric power (e.g. in sequence, side-by-side, or in a grid pattern/layout). The use of light field display 3003 offers multiple possibilities regarding how the optotypes are presented, and at which dioptric power each may be rendered. The optotypes may be presented sequentially at different dioptric power, via one or more dioptric power increments. In some embodiments, the patient and/or operator may control the speed and size of the dioptric power increments.

Figure 37:
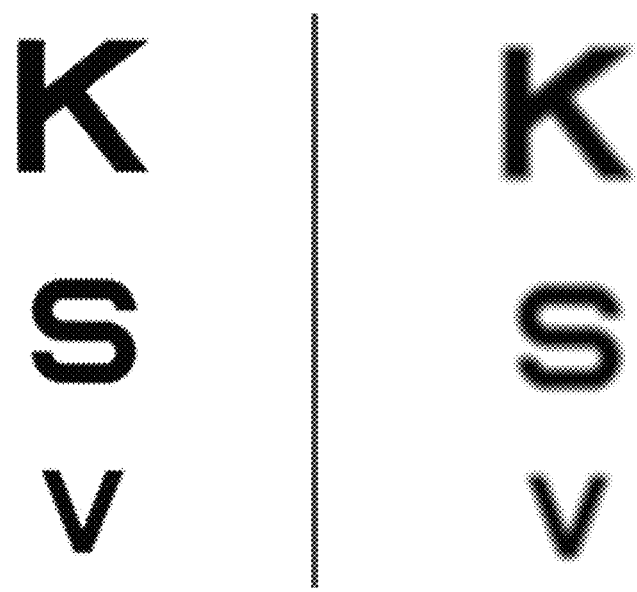
FIG. 37 is a schematic diagram of an exemplary light field image showing two columns of optotypes at different dioptric power for the method of FIG. 36, in accordance with one embodiment.

In some embodiments, optotypes may also be presented, at least in part, simultaneously on the same image but rendered at a different dioptric power (via ray-tracing methods 2400, or 2700, for example). For example, FIG. 37 shows an example of how different optotypes may be displayed to the patient but rendered with different dioptric power simultaneously. These may be arranged in columns or in a table or similar. In FIG. 37, we see two columns of three optotypes (K, S, V), varying in size, as they are perceived by a patient, each column being rendered at different degrees of refractive correction (e.g. dioptric power). In this specific example, the optotypes on the right are being perceived as blurrier than the optotypes on the left.

Thus, at step 3615, the patient would communicate/verbalize this information to the operator or input/select via control interface 3011 the left column as the one being clearer. Thus, in some embodiments, method 3600 may be configured to implement dynamic testing functions that dynamically adjust one or more displayed optotype's dioptric power in real-time in response to a designated input, herein shown by the arrow going back from step 3620 to step 3610. In the case of sequentially presented optotypes, the patient may indicate when the optotypes shown are clearer. In some embodiments, the patient may control the sequence of optotypes shown (going back and forth as needed in dioptric power), and the speed and increment at which these are presented, until he/she identifies the clearest optotype. In some embodiments, the patient may indicate which optotype or which group of optotypes is the clearest by moving an indicator icon or similar within the displayed image.

In some embodiments, the optotypes may be presented via a video feed or similar.

In some embodiments, when using a reel of lenses or similar, discontinuous changes in dioptric power may be unavoidable. For example, the reel of lenses may be used to provide a larger increment in dioptric power, as discussed above. Thus, step 3610 may in this case comprise first displaying larger increments of dioptric power by changing lens as needed, and when the clearest or less blurry optotypes are identified, fine-tuning with continuous or smaller increments in dioptric power using the light field display. In the case of optotypes presented simultaneously, the refractive components 3007 may act on all optotypes at the same time, and the change in dioptric power between them may be controlled only by the light display 3003. In some embodiments, for example when using an electrically tunable fluid lens or similar, the change in dioptric power may be continuous.

In some embodiments, eye images may be recorded during steps 3610 to 3620 and analyzed to provide further diagnostics. For example, eye images may be compared to a bank or database of proprietary eye exam images and analyzed, for example via an artificial intelligence (AI) or Machine-learning (ML) system or similar. This analysis may be done by phoropter 3001 locally or via a remote server or database 3059.

Once the correct dioptric power needed to correct for the patient's reduced visual acuity is defined at step 3625, an eye prescription or vision correction parameter(s) may be derived from the total dioptric power used to display the best perceived optotypes.

In some embodiments, the patient, an optometrist or other eye-care professional may be able to transfer the patient's eye prescription directly and securely to his/her user profile store on said server or database 3059. This may be done via a secure website, for example, so that the new prescription information is automatically uploaded to the secure user profile on remote database 3059. In some embodiments, the eye prescription may be sent remotely to a lens specialist or similar to have prescription glasses prepared.

In some embodiments, the vision testing system 3000 may also or alternatively be used to simulate compensation for higher-order aberrations. Indeed, the light field rendering methods 1100, 1900, 2400, 2700, 4100 and 4300 described above may be used to compensation for higher order aberrations (HOA), and thus be used to validate externally measured or tested HOA via method 3600, in that a measured, estimated or predicted HOA can be dynamically compensated for using the system described herein and thus subjectively visually validated by the viewer in confirming whether the applied HOA correction satisfactory addresses otherwise experienced vision deficiencies.

Figure 48:
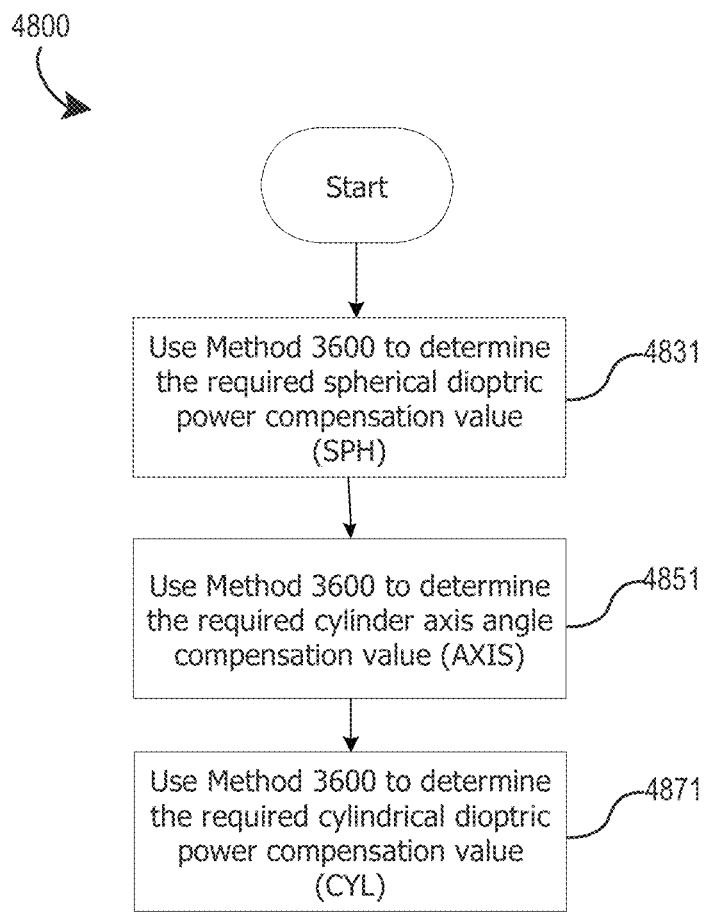
FIG. 48 is a process flow diagram illustrating an exemplary method for providing an eye examination in the context astigmatism or similar conditions, in accordance with one embodiment.

In one embodiment, astigmatism may be tested by repeating the steps of method 3600 sequentially to determine the required spherical dioptric power 4001, the cylinder axis angle 4007 and the cylindrical dioptric power 4005 (e.g. SPH, AXIS and CYL parameters). This is shown in the process flow diagram of FIG. 48. For this example, the light field rendering methods 4100 or 4300 may be used to render light fields images with different combinations of spherical dioptric power 4001, cylindrical dioptric power 4005 and cylinder axis angle 4007, as explained above. Thus, in some embodiments, at step 4831, a first iteration of method 3600 may first be executed to determine the necessary spherical dioptric power 4001 adjustment, followed by a second iteration for determining the cylinder axis angle 4007 and finally a third iteration for determining the necessary cylindrical dioptric power 4005 adjustment.

At step 4831, in one embodiment, a series of optotypes may be shown sequentially or simultaneously, each optotype generated at a different spherical dioptric power 4001 as discussed above. Once the user has identified which optotype is the clearest at a good enough diopter resolution, that value of the corresponding spherical dioptric power 4001 that best compensates for the user's reduced visual acuity is identified (e.g. SPH parameter).

Figure 49:
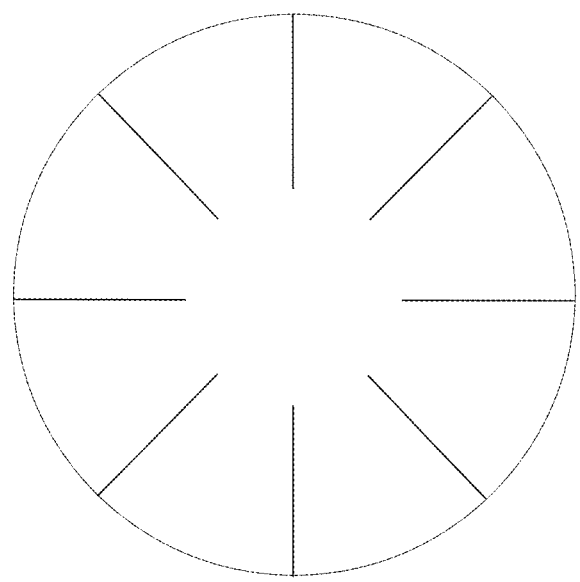
FIG. 49 is a schematic figure of an exemplary diagram or optotype that may be presented to a user to diagnose astigmatism or similar conditions, in accordance with one embodiment.

Then at step 4851, a second iteration of method 3600 may then be executed for determining the cylinder axis angle 4007. In some embodiments, the optotypes displayed or generated by phoropter 3001 may be akin to what would be seen by the user when using a Jackson cross-cylinder device or similar (at step 3610 of method 3600). For example, light field display 3003 may be operable to display images comprising lines or dots located at specific angles for marking the principal meridians as generated by the light field display (an example of which is shown in FIG. 49). In some embodiments, to find an initial starting value for the cylinder axis angle 4007, a series of lines arranged like on a dial of an analog clock may be first displayed without any cylindrical dioptric power being generated. The user may then be asked which line looks different from the others (e.g. not quite straight), which will define the starting value of the cylinder axis angle 4007. Then, a small cylindrical dioptric power 4005 is generated at the required cylinder axis angle 4007 (for example 0.5 D for normal users or 1D for low vision users), and the process is iterated by generating new dial-like images and refining the value of the cylinder axis angle 4007 until a good value is determined (e.g. AXIS parameter).

Finally, at step 4871, once the required cylinder axis angle 4007 is known (i.e. the required meridian), method 3600 may be repeated a final time by varying the cylindrical dioptric power 4005 generated for each image using the spherical dioptric power 4001 and cylinder axis angle 4007 values identified above, until the user communicates which image is the clearest or most comfortable to view, thus giving the final cylindrical dioptric power value 4005 required. At the end of this exemplary process 4800, the best values of SPH, CYL and AXIS required to compensate for the user's astigmatism will have been determined.

In one such embodiment, a HOA correction preview can be rendered, for example, in enabling users to appreciate the impact HOA correction (e.g. HOA compensating eyewear or contact lenses, intraocular lenses (IOL), surgical procedures, etc.), or different levels or precisions thereof, could have on their visual acuity. Alternatively, HOA corrections once validated can be applied on demand to provide enhanced vision correction capabilities to consumer displays.

Higher-order aberrations can be defined in terms of Zernike polynomials, and their associated coefficients. In some embodiments, the light field phoropter may be operable to help validate or confirm measured higher-order aberrations, or again to provide a preview of how certain HOA corrections may lead to different degrees of improved vision. To do so, in some embodiments, the ray-tracing methods 1100, 1900, 2400, or 2700 may be modified to account for the wavefront distortion causing the HOA which are characterized by a given set of values of the Zernike coefficients. Such an approach may include, in some embodiments, extracting or deriving a set of light rays corresponding to a given wavefront geometry. Thus, the light field display may be operable to compensate for the distortion by generating an image corresponding to an "opposite" wavefront aberration. In some embodiments, the corresponding total aberration values may be normalized for a given pupil size of circular shape. Moreover, in some embodiments, the wavefront may be scaled, rotated and transformed to account for the size and shape of the view zones. This may include concentric scaling, translation of pupil center, and rotation of the pupil, for example.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

While the present disclosure describes various exemplary embodiments, the disclosure is not so limited. To the contrary, the disclosure is intended to cover various modifications and equivalent arrangements included within the general scope of the present disclosure.

What is claimed is:

1. A device operable to dynamically adjust user perception of an input image, the device comprising:
    an array of digital display pixels;
    a corresponding array of light field shaping elements (LFSEs) shaping a light field emanating from said pixels; and
    a hardware processor operable on pixel data for the input image to output adjusted image pixel data to be rendered via said LFSEs to dynamically adjust perception of the input image as so rendered to at least partially accommodate a designated visual acuity accommodation defined by a designated variable optical vision parameter that varies across user pupil locations, by digitally:
        for each given pixel, defining a corresponding location on an adjusted image surface as a function of a direction of a given light field emanated by said given pixel given a corresponding LFSE and said designated variable optical vision parameter for a given pupil location intersected by said given light field;
        associating an adjusted image pixel value with said given pixel given said corresponding location on said adjusted image surface; and
        rendering each said given pixel according to said adjusted pixel value associated therewith, thereby perceptively rendering a perceptively adjusted version of the input image that at least partially accommodates said designated visual acuity accommodation.

2. The device of claim 1, wherein said hardware processor is further operable to digitally project a given ray trace between said given pixel and said given pupil location; and identify said designated variable optical vision parameter for said given pupil location.

3. The device of claim 1, wherein said designated visual acuity accommodation comprises a spherical optical power correction, a cylindrical optical power correction and a cylindrical axis correction, and wherein said designated variable optical vision parameter is respectively designated as a function of said designated visual acuity accommodation for each said given pupil location.

4. The device of claim 1, wherein, for at least some said given pixel, said adjusted image surface comprises a respective virtual image plane virtually positioned relative to the digital display pixels at a designated distance from said user pupil and corresponding with a respective said designated variable optical vision parameter identified for said given pupil location, and wherein said hardware processor is further operable to digitally map the input image on said respective virtual image plane and associate said adjusted image pixel value based on said mapping.

5. The device of claim 1, wherein said adjusted image surface comprises a user retinal plane; and wherein said defining said adjusted image location comprises digitally redirecting a given ray trace at said given pupil location according to said designated variable optical vision parameter so to intersect said retinal plane at said adjusted image location, wherein said hardware processor is further operable to digitally map the input image on said user retinal plane and associate said adjusted image pixel value based on said mapping.

6. The device of claim 5, wherein said redirecting comprises:
deriving from said given pupil location and said designated optical vision parameter defined therefor, an offset pupil location through which a corresponding ray trace is estimated to propagate substantially undeviated by an eye to a corresponding eye focal point on a user eye focal plane, wherein said offset pupil location is digitally calculated as a function of a spherical optical power parameter, a cylindrical optical power parameter and a cylindrical optical axis parameter; and
redirecting said given ray trace toward said eye focal point so to intersect said user retinal plane at said adjusted image location.

7. The device of claim 1, wherein said hardware processor is further operable to adjust said designated variable optical vision parameter to accommodate for a distinct visual acuity accommodation until an optimal visual acuity accommodation is identified, wherein said optimal visual acuity accommodation comprises an optimal astigmatism accommodation.

8. The device of claim 1, wherein said hardware processor is further operable to adjust said designated variable optical vision parameter to accommodate for a distinct visual acuity accommodation to provide a preview of a relative visual impact of said distinct visual acuity accommodation.

9. The device of claim 1, wherein said designated visual acuity accommodation comprises an astigmatism accommodation.

10. A computer-implemented method, automatically implemented by one or more digital processors, to dynamically adjust user perception of an input image to be rendered by an array of digital display pixels via a corresponding array of light field shaping elements (LFSE) to at least partially accommodate a designated visual acuity accommodation defined by a designated variable optical vision parameter that varies across user pupil locations, the method comprising, for each given pixel:
defining a corresponding location on an adjusted image surface as a function of a direction of a given light field emanated by said given pixel given a corresponding LFSE and said designated variable optical vision parameter for a given pupil location intersected by said given light field;
associating an adjusted image pixel value with said given pixel given said corresponding location on said adjusted image surface; and
rendering each said given pixel according to said adjusted pixel value associated therewith, thereby perceptively rendering a perceptively adjusted version of the input image that at least partially accommodates said designated visual acuity accommodation.

11. The method of claim 10, further comprising:
digitally projecting a given ray trace between said given pixel and said given pupil location; and
identifying said designated variable optical vision parameter for said given pupil location.

12. The method of claim 10, wherein said designated visual acuity accommodation comprises a spherical optical power correction, a cylindrical optical power correction and a cylindrical axis correction, and wherein said designated variable optical vision parameter is respectively designated as a function of said designated visual acuity accommodation for each said given pupil location.

13. The method of claim 10, wherein, for at least some said given pixel, said adjusted image surface comprises a respective virtual image plane virtually positioned relative to the digital display pixels at a designated distance from said user pupil and corresponding with a respective said designated variable optical vision parameter identified for said given pupil location, and wherein the method further comprises digitally mapping the input image on said respective virtual image plane and associating said adjusted image pixel value based on said mapping.

14. The method of claim 13, wherein the method further comprises digitally mapping the input image on said respective virtual image plane and associating said adjusted image pixel value based on said mapping, wherein a mapping area of at least some said respective virtual image plane is defined by a non-rectangular convex quadrilateral area.

15. The method of claim 10, wherein said adjusted image surface comprises a user retinal plane; and wherein said defining said adjusted image location comprises digitally redirecting a given ray trace at said given pupil location according to said designated variable optical vision parameter so to intersect said retinal plane at said adjusted image location, wherein the method further comprises digitally mapping the input image on said user retinal plane and associating said adjusted image pixel value based on said mapping.

16. The method of claim 15, wherein said redirecting comprises:
deriving from said given pupil location and said designated optical vision parameter defined therefor, an offset pupil location through which a corresponding ray trace is estimated to propagate substantially undeviated to a corresponding eye focal point on a user eye focal plane, wherein said offset pupil location is digitally calculated as a function of a spherical optical power parameter, a cylindrical optical power parameter and a cylindrical optical axis parameter; and
redirecting said given ray trace toward said eye focal point so to intersect said user retinal plane at said adjusted image location.

17. The method of claim 10, further comprising adjusting said designated variable optical vision parameter to accommodate for a distinct visual acuity accommodation until an optimal visual acuity accommodation is identified, wherein said optimal visual acuity accommodation comprises an optimal astigmatism accommodation.

18. The method of claim 10, wherein each said designated visual acuity accommodation is defined by a designated optical vision parameter comprising a spherical power, a cylindrical power and an optical axis parameter.

19. The method of claim 10, further comprising adjusting said designated optical vision parameter to accommodate for a distinct visual acuity accommodation to provide a preview of a relative visual impact of said distinct visual acuity accommodation.

20. The method of claim 10, wherein said designated visual acuity accommodation comprises an astigmatism accommodation.

21. A non-transitory computer-readable medium comprising digital instructions to be implemented by one or more digital processors to automatically adjust perception of an input to be rendered via an array of digital display pixels and a corresponding array of light field shaping elements (LFSE) to at least partially accommodate a designated visual acuity accommodation defined by a designated variable optical vision parameter that varies across user pupil locations, by, for each given pixel, digitally:
- defining a corresponding location on an adjusted image surface as a function of a direction of a given light field emanated by said given pixel given a corresponding LFSE and said designated variable optical vision parameter for a given pupil location intersected by said given light field; and
- associating an adjusted image pixel value with said given pixel given said corresponding location on said adjusted image surface for perceptively rendering a perceptively adjusted version of the input image that at least partially accommodates said designated visual acuity accommodation.

22. The non-transitory computer-readable medium of claim 21, further comprising instructions to digitally project a given ray trace between said given pixel and said given pupil location; and identify said designated variable optical vision parameter for said given pupil location.

23. The non-transitory computer-readable medium of claim 21, wherein, for at least some said given pixel, said adjusted image surface comprises a respective virtual image plane virtually positioned relative to the digital display pixels at a designated distance from said user pupil and corresponding with a respective said designated optical vision parameter identified for said given pupil location, and wherein the instructions further cause the one or more digital processors to digitally map the input on said respective virtual image plane and associating said adjusted image pixel value based on said mapping.

24. The non-transitory computer-readable medium of claim 23, wherein a mapping area of at least some said respective virtual image plane is defined by a non-rectangular convex quadrilateral area.

25. The non-transitory computer-readable medium of claim 21, wherein, for at least some said given pixel, said adjusted image surface comprises a user retinal plane; and wherein said defining said adjusted image location comprises digitally redirecting a given ray trace between said given pixel and said given pupil location at said given pupil location according to said designated variable optical vision parameter so to intersect said retinal plane at said adjusted image location, wherein the non-transitory computer-readable medium further comprises instructions for digitally mapping the input image on said user retinal plane and associating said adjusted image pixel value based on said mapping.

26. The non-transitory computer-readable medium of claim 25, wherein said redirecting comprises:
- defining a corresponding ray trace from said given LFSE estimated to propagate substantially undeviated to a corresponding eye focal point on a user eye focal plane; and
- redirecting said given ray trace toward said eye focal point so to intersect said user retinal plane at said adjusted image location.

27. The non-transitory computer-readable medium of claim 25, wherein said redirecting comprises:
- deriving from said given pupil location and said designated optical vision parameter defined therefor, an offset pupil location through which a corresponding ray trace is estimated to propagate substantially undeviated to a corresponding eye focal point on a user eye focal plane, wherein said offset pupil location is digitally calculated, at least in part, as a function of a cylindrical optical focusing parameter and a cylindrical optical axis parameter; and
- redirecting said given ray trace toward said eye focal point so to intersect said user retinal plane at said adjusted image location.

28. The non-transitory computer-readable medium of claim 21, further comprising digital instructions to adjust said designated variable optical vision parameter to accommodate for a distinct visual acuity accommodation until an optimal visual acuity accommodation is identified.

29. The non-transitory computer-readable medium of claim 21, further comprising digital instructions to adjust said designated variable optical vision parameter to accommodate for a distinct visual acuity accommodation to provide a preview of a relative visual impact of said distinct visual acuity accommodation.

30. The non-transitory computer-readable medium of claim 21, wherein said designated visual acuity accommodation comprises an astigmatism accommodation.

* * * * *